United States Patent [19]

Anthony et al.

[11] Patent Number: 5,652,257
[45] Date of Patent: Jul. 29, 1997

[54] HETEROCYCLE-CONTAINING INHIBITORS OF FARNESYL-PROTEIN TRANSFERASE

[75] Inventors: Neville J. Anthony, Hatfield; S. Jane deSolms, Norristown; Robert P. Gomez, Perkasie; Samuel L. Graham, Schwenksville; John H. Hutchinson, Philadelphia; Gerald E. Stokker, Gwynedd Valley, all of Pa.

[73] Assignee: Merck & Co., Inc., Rahway, N.J.

[21] Appl. No.: 526,244

[22] Filed: Sep. 21, 1995

Related U.S. Application Data

[63] Continuation-in-part of Ser. No. 314,974, Sep. 29, 1994, abandoned.

[51] Int. Cl.$^6$ .................... A61K 31/415; C07D 233/02; C07D 233/04; C07D 233/54; C07D 233/30
[52] U.S. Cl. .................... 514/399; 514/397; 548/311.1; 548/315.4; 548/324.1
[58] Field of Search .................... 548/324.1, 311.1, 548/315.4; 514/399, 397

[56] References Cited

U.S. PATENT DOCUMENTS

| | | | |
|---|---|---|---|
| 5,043,268 | 8/1991 | Stock | 514/399 X |
| 5,141,851 | 8/1992 | Brown et al. | 514/399 X |
| 5,238,922 | 8/1993 | Graham et al. | 514/399 X |
| 5,326,773 | 7/1994 | De Solms et al. | 514/399 X |
| 5,340,828 | 8/1994 | Graham et al. | 514/399 X |
| 5,352,705 | 10/1994 | Deana et al. | 514/399 X |
| 5,420,245 | 5/1995 | Brown et al. | 530/328 |

FOREIGN PATENT DOCUMENTS

| | | | |
|---|---|---|---|
| 0 456 180 A1 | 11/1991 | European Pat. Off. | 514/399 |
| 0 618 221 A2 | 10/1994 | European Pat. Off. | 514/399 |
| 0 675 112 A1 | 10/1995 | European Pat. Off. | 514/399 |
| 7-112930 | 5/1995 | Japan | 514/399 |
| WO91/16340 | 10/1991 | WIPO | 514/399 |
| WO95/11917 | 5/1994 | WIPO | 514/399 |
| WO95/09000 | 4/1995 | WIPO | 514/399 |
| WO95/09001 | 4/1995 | WIPO | 514/399 |
| WO95/12612 | 5/1995 | WIPO | 514/399 |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

James, G.L. et al., "Benzodiazepine Peptidomimetic BZ–5B Interrupts the MAP Kinase Activation Pathway in H–Ras–transformed Rat–1 Cells, but Not in Untransformed Cells," The Journal of Biological Chemistry, vol. 369, No. 44, pp. 27705–27714 (1994).

James, G.L. et al., "Benzodiazepine Peptidomimetics: Potent Inhibitors of Ras Farnesylation in Animal Cells", Science, vol. 260, pp. 1937–1942 (1993).

Kohl, N.E. et al., "Selective Inhibition of ras–Dependent Transformation by a Farnesyltransferase Inhibitor", Science, vol. 260, pp. 1934–1937 (1993).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Pompliano, D.L., "Steady–State Kinetic Mechanism of Ras Farnesyl:Protein Transferase", Biochemistry, vol. 31, pp. 3800–3807 (1992).

James, G., et al., "Polylysine and CVIM Sequences of K–RasB Dictate Specificity of Prenylation and Confer Resistance to Benzodiazepine Peptidomimetic in Vitro", The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8 (1995).

Lorenzino, L.S., et al., "A Peptimomimetic Inhibitor of Farnesyl:Protein Transferase Blcoks the Anchorage–dependent and–independent Growth of Human Tumor Cell Lines," Cancer Research, 55, pp. 5302–5309 (1995).

Primary Examiner—Floyd D. Higel
Attorney, Agent, or Firm—David A. Muthard; Mark R. Daniel

[57] ABSTRACT

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

39 Claims, No Drawings

HETEROCYCLE-CONTAINING INHIBITORS OF FARNESYL-PROTEIN TRANSFERASE

RELATED APPLICATIONS

The present patent application is a continuation-in-part application of application Ser. No. 08/314,974, filed Sep. 29, 1994, now abandoned.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

It has recently been shown that farnesyl-protein transferase inhibitors are inhibitors of proliferation of vascular smooth muscle cells and are therefore useful in the prevention and thereapy of arteriosclerosis and diabetic disturbance of blood vessels (JP H7-112930).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drags inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae:

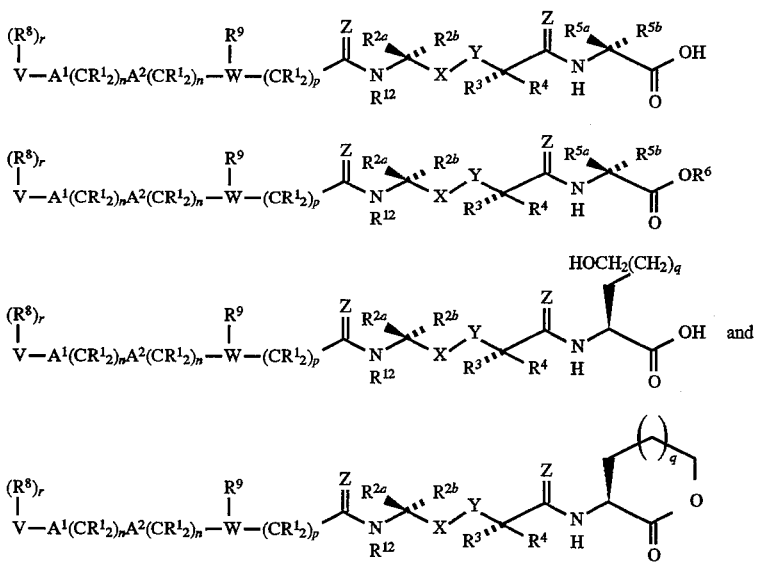

DETAILED DESCRIPTION OF THE INVENTION

The compounds of this invention inhibit the farnesylation of Ras. In a first embodiment of this invention, the Ras farnesyl transferase inhibitors are illustrated by the formula I:

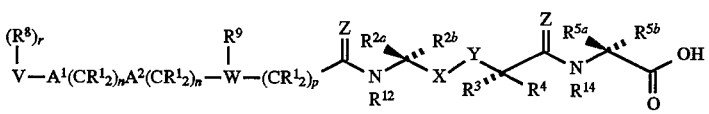

wherein:

$R^1$ is independently selected from:
a) hydrogen,
b) aryl, heterocyclic, cycloalkyl, alkenyl, alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{2a}$ and $R^{2b}$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_s-$;
$R^3$ and $R^4$ are independently selected from:

a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_s-$;
$R^{5a}$ and $R^{5b}$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$, $-SO_2N(R^{10})_2$, $R^{11}SO_2NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{5a}$ and $R^{5b}$ are combined to form $-(CH_2)_s-$ wherein one of the carbon atoms is optionally replaced by a moiety selected from: O, S(O)$_m$, —NC(O)—, and —N(COR$^{10}$)—; or R$^{5a}$ or R$^{5b}$ are combined with R$^{14}$ to form a ring such that

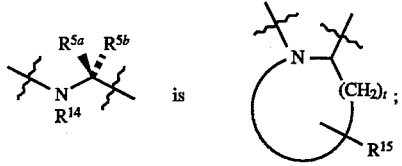

X-Y is a) 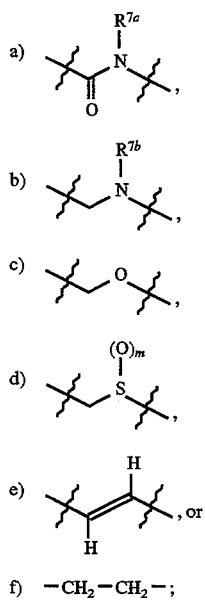

b)

c)

d)

e)

f) —CH$_2$—CH$_2$—;

R$^{7a}$ is selected from
a) hydrogen,
b) unsubstituted or substituted aryl,
c) unsubstituted or substituted heterocyclic,
d) unsubstituted or substituted cycloalkyl, and
e) C$_1$-C$_6$ alkyl substituted with hydrogen or an unsubstituted or substituted group selected from aryl, heterocyclic and cycloalkyl;

R$^{7b}$ is selected from
a) hydrogen,
b) unsubstituted or substituted aryl,
c) unsubstituted or substituted heterocyclic,
d) unsubstituted or substituted cycloalkyl,
e) C$_1$-C$_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and C$_1$-C$_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and C$_1$-C$_6$ alkyl substituted with hydrogen or an unsubstituted or substituted group selected from aryl, heterocyclic and cycloalkyl;

R$^8$ is independently selected from:
a) hydrogen,
b) aryl, heterocyclic, cycloalkyl, alkenyl, alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$-C$_6$ alkyl unsubstituted or substituted by aryl, heterocyclic, cycloalkyl, alkenyl, alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{11}$OC(O)NH—;

R$^9$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$-C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$-C$_6$ alkyl and aryl;

R$^{11}$ is independently selected from C$_1$-C$_6$ alkyl and aryl;

R$^{12}$ is independently selected from hydrogen and C$_1$-C$_6$ alkyl;

R$^{14}$ is independently selected from hydrogen, C$_1$-C$_6$ alkyl and benzyl;

R$^{15}$ is independently selected from hydrogen and C$_1$-C$_6$ alkyl;

A$^1$ and A$^2$ are independently selected from: a bond, —CH=CH—, —C≡C—, O, —N(R$^{10}$)—, —C(O)—, —C(O)NR$^{10}$—, —NR$^{10}$C(O)—, —S(O)$_2$N(R$^{10}$)—, —N(R$^{10}$)S(O)$_2$— or S(O)$_m$;

V is selected from:
a) hydrogen,
b) heterocycle,
c) aryl,
d) C$_1$-C$_{20}$ alkyl wherein from 0 to 4 non-terminal carbon atoms are replaced with a heteroatom selected from O, S, and N, and
e) C$_2$-C$_{20}$ alkenyl;

provided that V is not hydrogen if A$^1$ is S(O)$_m$ and V is not hydrogen if A$^1$ is a bond, n is 0 and A$^2$ is S(O)$_m$ or a bond;

W is a heterocycle;

Z is independently H$_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5; and t is 3, 4 or 5;

or the pharmaceutically acceptable salts thereof.

In a second embodiment of this invention the prodrugs of compounds of formula I are illustrated by the formula II:

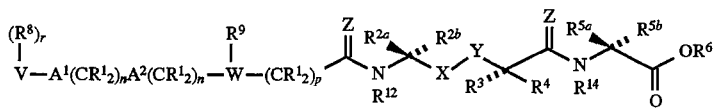

wherein:
R¹ is independently selected from:
a) hydrogen,
b) aryl, heterocyclic, cycloalkyl, alkenyl, alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{2a}$ and $R^{2b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_s-$;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_s-$;

$R^{5a}$ and $R^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$, $-SO_2N(R^{10})_2$, $R^{11}SO_2NR^{10}-$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^{10})-$; or $R^{5a}$ or $R^{5b}$ are combined with $R^{14}$ to form a ring such that

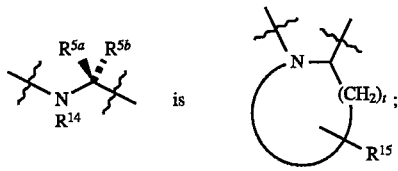

$R^6$ is
a) substituted or unsubstituted $C_1-C_8$ alkyl, wherein the substituent on the alkyl is selected from:
1) aryl,
2) heterocycle,
3) $-N(R^{11})_2$,
4) $-OR^{10}$, or b) 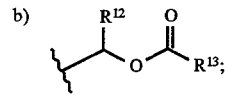

X-Y is a) 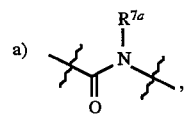

b) 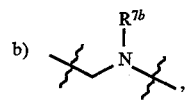

c) 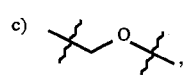

d) 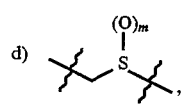

e) 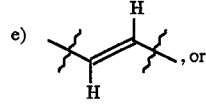, or f) 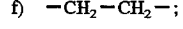 $-CH_2-CH_2-$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1-C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$-$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$-$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$-$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$-$C_6$ alkyl and aryl;

$R^{11}$ is independently selected from $C_1$-$C_6$ alkyl and aryl;

$R^{12}$ is independently selected from hydrogen and $C_1$-$C_6$ alkyl;

$R^{13}$ is independently selected from $C_1$-$C_6$ alkyl;

$R^{14}$ is independently selected from hydrogen, $C_1$-$C_6$ alkyl and benzyl;

$R^{15}$ is independently selected from hydrogen and $C_1$-$C_6$ alkyl;

$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
a) hydrogen,
b) heterocycle,
c) aryl,
d) $C_1$-$C_{20}$ alkyl wherein from 0 to 4 non-terminal carbon atoms are replaced with a heteroatom selected from O, S, and N, and
e) $C_2$-$C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5; and t is 3, 4 or 5;

or the pharmaceutically acceptable salts thereof.

In a third embodiment of this invention, the inhibitors of farnesyl transferase are illustrated by the formula III:

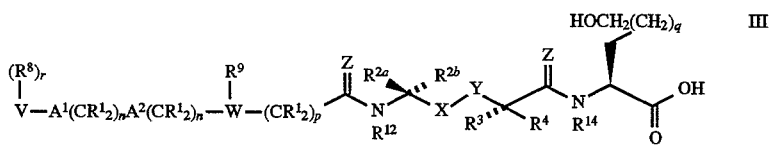

wherein:

$R^1$ is independently selected from:
a) hydrogen,
b) aryl, heterocyclic, cycloalkyl, alkenyl, alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$-$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$-$C_{20}$ alkyl, $C_2$-$C_{20}$ alkenyl, $C_3$-$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$-$C_{20}$ alkyl, and
d) $C_1$-$C_6$ alkyl substituted with an unsubstituted or substituted group selected from aryl, heterocycle and $C_3$-$C_{10}$ cycloalkyl; or $R^{2a}$ and $R^{2b}$ are combined to form —(CH$_2$)$_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted $C_1$-$C_{20}$ alkyl, $C_2$-$C_{20}$ alkenyl, $C_3$-$C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_s-$;

X-Y is a) 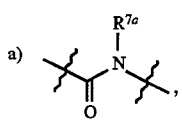

b) 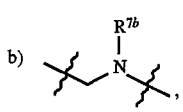

c) 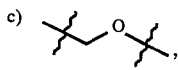

d) 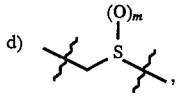

e) 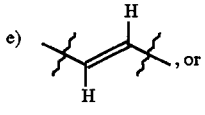, or f) 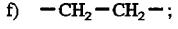 $-CH_2-CH_2-$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1-C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1-C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O-$, $R^{11}S(O)_m-$, $R^{10}C(O)NR^{10}-$, CN, $NO_2$, $R^{10}_2N-C(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by aryl, heterocyclic, cycloalkyl, alkenyl, alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $R^{10}OC(O)-$, $N_3$, $-N(R^{10})_2$, or $R^{11}OC(O)NH-$;

$R^9$ is selected from:
a) hydrogen,
b) alkenyl, alkynyl, perfluoroalkyl, F, Cl, Br, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{10}$ is independently selected from hydrogen, $C_1-C_6$ alkyl and aryl;

$R^{11}$ is independently selected from $C_1-C_6$ alkyl and aryl;

$R^{12}$ is independently selected from hydrogen and $C_1-C_6$ alkyl;

$R^{14}$ is independently selected from hydrogen, $C_1-C_6$ alkyl and benzyl;

$A^1$ and $A^2$ are independently selected from: a bond, $-CH=CH-$, $-C\equiv C-$, $-C(O)-$, $-C(O)NR^{10}-$, O, $-N(R^{10})-$, $-NR^{10}C(O)-$, $-S(O)_2N(R^{10})-$, $-N(R^{10})S(O)_2-$ or $S(O)_m$;

V is selected from:
a) hydrogen,
b) heterocycle,
c) aryl,
d) $C_1-C_{20}$ alkyl wherein from 0 to 4 non-terminal carbon atoms are replaced with a heteroatom selected from O, S, and N, and
e) $C_2-C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen; and s is 4 or 5;

or the pharmaceutically acceptable salts thereof.

In a fourth embodiment of this invention the prodrugs of compounds of formula III are illustrated by the formula IV:

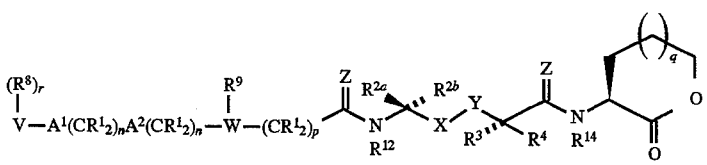

wherein:

R[1] is independently selected from:
a) hydrogen,
b) aryl, heterocyclic, cycloalkyl, alkenyl, alkynyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$,
c) $C_1$–$C_6$ alkyl unsubstituted or substituted by aryl, heterocyclic, cycloalkyl, alkenyl, alkynyl, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)NR^{10}—$;

$R^{2a}$ and $R^{2b}$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form $—(CH_2)_s—$;

$R^3$ and $R^4$ are independently selected from:
a) a side chain of a naturally occurring amino acid,
b) an oxidized form of a side chain of a naturally occurring amino acid which is:
 i) methionine sulfoxide, or
 ii) methionine sulfone, and
c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^{10})_2$, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form $—(CH_2)_s—$;

X-Y is a) 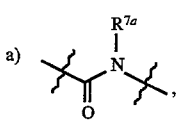

b) 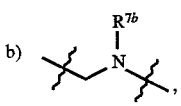

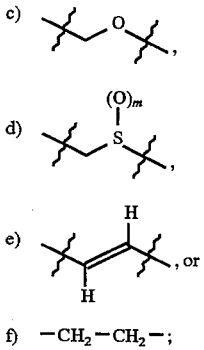

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O—$, $R^{11}S(O)_m—$, $R^{10}C(O)NR^{10}—$, CN, $NO_2$, $R^{10}_2N—C(NR^{10})—$, $R^{10}C(O)—$, $R^{10}OC(O)—$, $N_3$, $—N(R^{10})_2$, or $R^{11}OC(O)NR^{10}—$, and
c) $C_1$–$C_6$ alkyl unsubstituted or substituted by aryl, heterocyclic, cycloalkyl, alkenyl, alkynyl, perfluoroalkyl, F, Cl, Br, $R^{10}O—$, $R^{11}S(O)_m—$, $R^{10}C(O)NH—$, CN, $H_2N—C(NH)—$, $R^{10}C(O)—$, $R^{10}OC(O)—$, $N_3$, $—N(R^{10})_2$, or $R^{11}OC(O)NH—$;

$R^9$ is selected from:
a) hydrogen,
b) alkenyl, alkynyl, perfluoroalkyl, F, Cl, Br, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—C$(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen, $C_1$–$C_6$ alkyl and benzyl;

$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
a) hydrogen,
b) heterocycle,
c) aryl,
d) $C_1$–$C_{20}$ alkyl wherein from 0 to 4 non-terminal carbon atoms are replaced with a heteroatom selected from O, S, and N, and
e) $C_2$–$C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen; and s is 4 or 5;

or the pharmaceutically acceptable salts thereof.

In a more preferred embodiment of this invention, the Ras farnesyl transferase inhibitors are illustrated by the formula I:

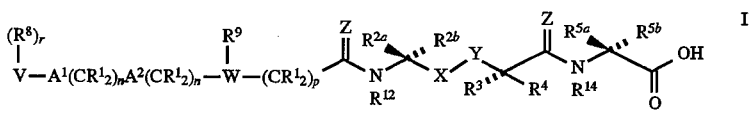

wherein:

$R^1$ is independently selected from:
a) hydrogen,
b) aryl, heterocyclic, cycloalkyl, $R^{10}O$—, —$N(R^{10})_2$ or alkenyl,
c) $C_1$–$C_6$ alkyl unsubstituted or substituted by aryl, heterocyclic, cycloalkyl, alkenyl, $R^{10}O$—, or —$N(R^{10})_2$;

$R^{2a}$ is selected from:
a) a side chain of a naturally occurring amino acid, wherein the amino acid is selected from alanine, leucine, isoleucine and valine;
b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
i) methionine sulfoxide, or
ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$—, —$SO_2N(R^{10})_2$, $R^{11}SO_2NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and
b) $C_1$–$C_3$ alkyl; or $R^{5a}$ or $R^{5b}$ are combined with $R^{14}$ to form a ring such that

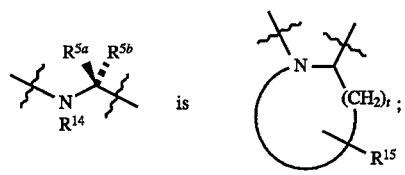

X-Y is

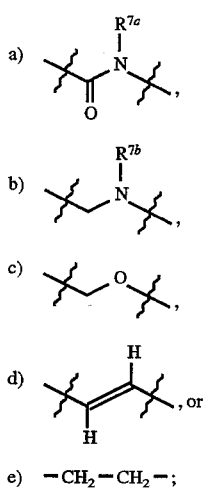

a) [structure with R^{7a}]

b) [structure with R^{7b}]

c) [structure with O]

d) [structure with H, H], or e) $-CH_2-CH_2-$;

$R^{7a}$ is selected from
 a) hydrogen,
 b) unsubstituted or substituted aryl,
 c) unsubstituted or substituted heterocyclic,
 d) unsubstituted or substituted cycloalkyl, and
 e) $C_1-C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
 a) hydrogen,
 b) unsubstituted or substituted aryl,
 c) unsubstituted or substituted heterocyclic,
 d) unsubstituted or substituted cycloalkyl,
 e) $C_1-C_6$ alkyl substituted with hydrogen or an unsubstituted or substituted group selected from aryl, heterocyclic and cycloalkyl,
 f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
 g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
 a) hydrogen,
 b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
 c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^9$ is selected from:
 a) hydrogen,
 b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
 c) $C_1-C_6$ alkyl unsubstituted or substituted by $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $-N(R^{10})_2$, or $R^{11}OC(O)NR^{10}-$;

$R^{10}$ is independently selected from hydrogen, $C_1-C_6$ alkyl and aryl;

$R^{11}$ is independently selected from $C_1-C_6$ alkyl and aryl;

$R^{12}$ is independently selected from hydrogen and $C_1-C_6$ alkyl;

$R^{14}$ is independently selected from hydrogen and $C_1-C_6$ alkyl;

$R^{15}$ is independently selected from hydrogen and $C_1-C_6$ alkyl;

$A^1$ and $A^2$ are independently selected from: a bond, $-CH=CH-$, $-C\equiv C-$, $-C(O)-$, $-C(O)NR^{10}-$, O, $-N(R^{10})-$, $-NR^{10}C(O)-$, $-S(O)_2N(R^{10})-$, $-N(R^{10})S(O)_2-$ or $S(O)_m$;

V is selected from:
 a) heterocycle selected from pyrrolidinyl, imidazolyl, pyridinyl, thiazolyl, pyridonyl, 2-oxopiperidinyl, indolyl, quinolinyl, isoquinolinyl, and thienyl,
 b) aryl,
 c) $C_1-C_{20}$ alkyl wherein from 0 to 4 non-terminal carbon atoms are replaced with a heteroatom selected from O, S, and N, and
 d) $C_2-C_{20}$ alkenyl;
 provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 2;

s is 4 or 5; and t is 3, 4 or 5;

or the pharmaceutically acceptable salts thereof.

In a second more preferred embodiment of this invention, the prodrugs of the preferred compounds of formula I are illustrated by the formula II:

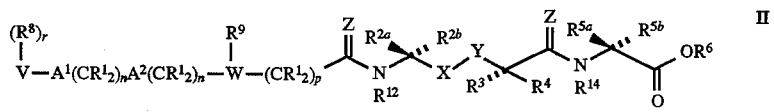

wherein:

R¹ is independently selected from:
a) hydrogen,
b) aryl, heterocyclic, cycloalkyl, $R^{10}O—$, $—N(R^{10})_2$ or alkenyl,
c) $C_1-C_6$ alkyl unsubstituted or substituted by aryl, heterocyclic, cycloalkyl, alkenyl, $R^{10}O—$, or $—N(R^{10})_2$;

$R^{2a}$ is selected from:
a) a side chain of a naturally occurring amino acid, wherein the amino acid is selected from alanine, leucine, isoleucine and valine;
b) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1-C_{20}$ alkyl, and
c) $C_1-C_6$ alkyl substituted with an unsubstituted or substituted group selected from aryl, heterocycle and $C_3-C_{10}$ cycloalkyl; and $R^{2b}$ is selected from hydrogen and $C_1-C_6$ alkyl; or $R^{2a}$ and $R^{2b}$ are combined to form $—(CH_2)_s—$;

R³ and R⁴ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1-C_{20}$ alkyl, and
d) $C_1-C_6$ alkyl substituted with an unsubstituted or substituted group selected from aryl, heterocycle and $C_3-C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
i) methionine sulfoxide, or
ii) methionine sulfone, and
c) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$, $—SO_2N(R^{10})_2$, $R^{11}SO_2NR^{10}—$ and $C_1-C_{20}$ alkyl, and
d) $C_1-C_6$ alkyl substituted with an unsubstituted or substituted group selected from aryl, heterocycle and $C_3-C_{10}$ cycloalkyl;

$R^{5a}$ is selected from:
a) hydrogen, and
b) $C_1-C_3$ alkyl; or $R^{5a}$ or $R^{5b}$ are combined with $R^{14}$ to form a ring such that

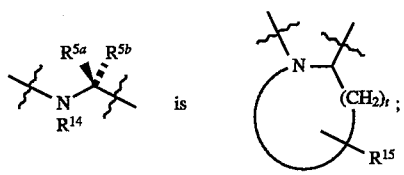 is 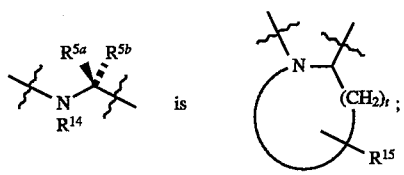

R⁶ is
a) substituted or unsubstituted $C_1-C_8$ alkyl, wherein the substituent on the alkyl is selected from:
1) aryl,
2) heterocycle,
3) $—N(R^{11})_2$,
4) $—OR^{10}$, or b) 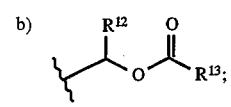

X-Y is

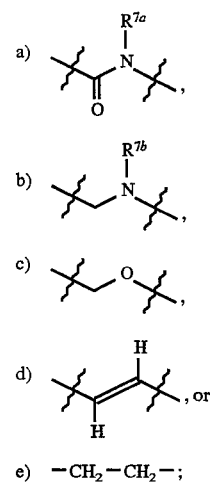

e) $—CH_2—CH_2—$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1-C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1-C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{13}$ is 1,1-dimethylethyl;

$R^{14}$ is independently selected from hydrogen and $C_1$–$C_6$ alkyl;

$R^{15}$ is independently selected from hydrogen and $C_1$–$C_6$ alkyl;

$A^1$ and $A^2$ are independently selected from: a bond, —CH=CH—, —C≡C—, —C(O)—, —C(O)$NR^{10}$—, O, —$N(R^{10})$—, —$NR^{10}C(O)$—, —$S(O)_2N(R^{10})$—, —$N(R^{10})S(O)_2$— or $S(O)_m$;

V is selected from:
  a) heterocycle selected from pyrrolidinyl, imidazolyl, pyridinyl, thiazolyl, pyridonyl, 2-oxopiperidinyl, indolyl, quinolinyl, isoquinolinyl, and thienyl,
  b) aryl,
  c) $C_1$–$C_{20}$ alkyl wherein from 0 to 4 non-terminal carbon atoms are replaced with a heteroatom selected from O, S, and N, and
  d) $C_2$–$C_{20}$ alkenyl;
  provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 2;

s is 4 or 5; and t is 3, 4 or 5;

or the pharmaceutically acceptable salts thereof.

In a third more preferred embodiment of this invention, the inhibitors of farnesyl transferase are illustrated by the formula III:

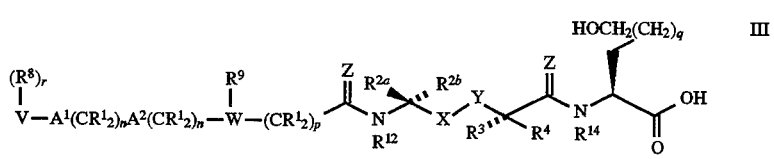

wherein:

$R^1$ is independently selected from:
  a) hydrogen,
  b) aryl, heterocyclic, cycloalkyl, $R^{10}O$—, —$N(R^{10})_2$ or alkenyl,
  c) $C_1$–$C_6$ alkyl unsubstituted or substituted by aryl, heterocyclic, cycloalkyl, alkenyl, $R^{10}O$—, or —$N(R^{10})_2$;

$R^{2a}$ is selected from:
  a) a side chain of a naturally occurring amino acid, wherein the amino acid is selected from alanine, leucine, isoleucine and valine;
  b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

X-Y is

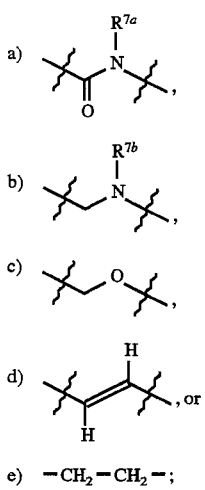

e) $-CH_2-CH_2-$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1-C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1-C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-R^{10}OC(O)-$, $-N(R^{10})_2$, $R^{11}OC(O)NR^{10}-$;

$R^9$ is selected from:
a) hydrogen,
b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
c) $C_1-C_6$ alkyl unsubstituted or substituted by $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $-N(R^{10})_2$, or $R^{11}OC(O)NR^{10}-$;

$R^{10}$ is independently selected from hydrogen, $C_1-C_6$ alkyl and aryl;

$R^{11}$ is independently selected from $C_1-C_6$ alkyl and aryl;

$R^{12}$ is independently selected from hydrogen and $C_1-C_6$ alkyl;

$R^{14}$ is independently selected from hydrogen and $C_1-C_6$ alkyl;

$A^1$ and $A^2$ are independently selected from: a bond, $-CH=CH-$, $-C\equiv C-$, $-C(O)-$, $-C(O)NR^{10}-$, O, $-N(R^{10})-$, $-NR^{10}C(O)-$, $-S(O)_2N(R^{10})-$, $-N(R^{10})S(O)_2-$ or $S(O)_m$;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl,
b) aryl,
c) $C_1-C_{20}$ alkyl wherein from 0 to 4 non-terminal carbon atoms are replaced with a heteroatom selected from O, S, and N, and
d) $C_2-C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

q is 0, 1 or 2;

r is 0 to 2; and s is 4 or 5;

or the pharmaceutically acceptable salts thereof.

In a fourth more preferred embodiment of this invention, the prodrugs of the preferred compounds of formula III are illustrated by the formula IV:

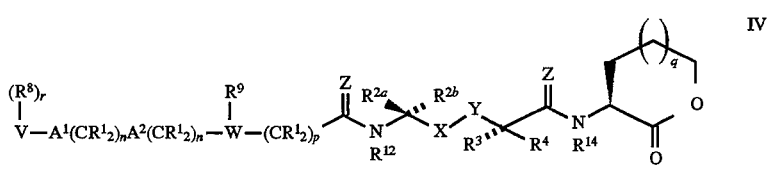

wherein:

R$^1$ is independently selected from:
  a) hydrogen,
  b) aryl, heterocyclic, cycloalkyl, R$^{10}$O—, —N(R$^{10}$)$_2$ or alkenyl,
  c) C$_1$–C$_6$ alkyl unsubstituted or substituted by aryl, heterocyclic, cycloalkyl, alkenyl, R$^{10}$O—, or —N(R$^{10}$)$_2$;

R$^{2a}$ is selected from:
  a) a side chain of a naturally occurring amino acid, wherein the amino acid is selected from alanine, leucine, isoleucine and valine;
  b) substituted or unsubstituted C$_1$–C$_{10}$ alkyl, C$_2$–C$_{10}$ alkenyl, C$_3$–C$_{10}$ cycloalkyl, aryl or heterocyclic group, wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
  c) C$_1$–C$_6$ alkyl substituted with an unsubstituted or substituted group selected from aryl, heterocycle and C$_3$–C$_{10}$ cycloalkyl; and R$^{2b}$ is selected from hydrogen and C$_1$–C$_6$ alkyl; or R$^{2a}$ and R$^{2b}$ are combined to form —(CH$_2$)$_s$—;

R$^3$ and R$^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted C$_1$–C$_{10}$ alkyl, C$_2$–C$_{10}$ alkenyl, C$_3$–C$_{10}$ cycloalkyl, aryl or heterocyclic group, wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
  d) C$_1$–C$_6$ alkyl substituted with an unsubstituted or substituted group selected from aryl, heterocycle and C$_3$–C$_{10}$ cycloalkyl;

X-Y is

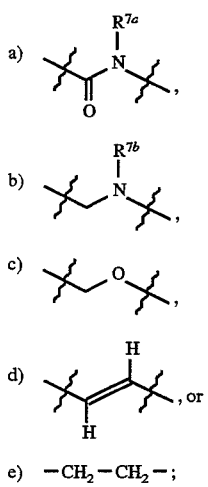

e) —CH$_2$—CH$_2$—;

R$^{7a}$ is selected from
  a) hydrogen,
  b) unsubstituted or substituted aryl,
  c) unsubstituted or substituted heterocyclic,
  d) unsubstituted or substituted cycloalkyl, and
  e) C$_1$–C$_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^{7b}$ is selected from
  a) hydrogen,
  b) unsubstituted or substituted aryl,
  c) unsubstituted or substituted heterocyclic,
  d) unsubstituted or substituted cycloalkyl,
  e) C$_1$–C$_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^8$ is selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^9$ is selected from:
  a) hydrogen,
  b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, —N(R$^{10}$)$_2$, R$^{11}$OC(O)NR$^{10}$—;

R$^{10}$ is independently selected from hydrogen, C$_1$–C$_6$ alkyl and aryl;

R$^{11}$ is independently selected from C$_1$–C$_6$ alkyl and aryl;

R$^{12}$ is independently selected from hydrogen and C$_1$–C$_6$ alkyl;

R$^{14}$ is independently selected from hydrogen and C$_1$–C$_6$ alkyl;

A$^1$ and A$^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
  a) heterocycle selected from pyrrolidinyl, imidazolyl, pyridinyl, thiazolyl, pyridonyl, 2-oxopiperidinyl, indolyl, quinolinyl, isoquinolinyl, and thienyl,
  b) aryl,
  c) C$_1$–C$_{20}$ alkyl wherein from 0 to 4 non-terminal carbon atoms are replaced with a heteroatom selected from O, S, and N, and
  d) C$_2$–C$_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

q is 0, 1 or 2;

r is 0 to 2; and s is 4 or 5;

or the pharmaceutically acceptable salts thereof.

The preferred compounds of this invention are as follows:

N-[2(S)-(1-(Phenylmethyl)-1H-imidazol-4-ylacetyl)amino-3(S)-methylpentyl]-N-1-naphthylmethyl-glycyl-methionine N-[2(S)-(1-(Phenylmethyl)-1H-imidazol-4-ylacetyl)amino-3(S)-methylpentyl]-N-1-naphthylmethyl-glycyl-methionine methyl ester N-[2(S)-(1-(Phenylmethyl)-1H-imidazol-5-ylacetyl)amino-3(S)-methylpentyl]-N-1-naphthylmethyl-glycyl-methionine N-[2(S)-(1-(Phenylmethyl)-1H-imidazol-5-ylacetyl)-amino-3(S)-methylpentyl]-N-1-naphthylmethyl-glycyl-methionine methyl ester N-[2(S)-(1-(4-Nitrophenylmethyl)-1H-imidazol-4-ylacetyl)amino-3(S)-methylpentyl]-N-1-naphthylmethyl-glycyl-methionine N-[(2S)-(1-(4-Nitrophenylmethyl)-1H-imidazol-4-ylacetyl)amino-3(S)-methylpentyl]-N-1-naphthylmethyl-glycyl-methionine methyl ester N-[2(S)-(1-(4-Nitrophenylmethyl)-1H-imidazol-5-ylacetyl)amino-3(S)-methylpentyl]-N-1-naphthylmethyl-glycyl-methionine N-[2(S)-(1-(4-Nitrophenyl-methyl)-1H-imidazol-5-ylacetyl)amino-3(S)-methylpentyl]-N-1-naphthylmethyl-glycyl-methionine methyl ester N-[2(S)-(1-(2-Naphthylmethyl)-1H-imidazol-5-ylacetyl) amino-3(S)-methylpentyl]-N-1-naphthylmethyl-glycyl-methionine N-[2(S)-(1-(2-Naphthylmethyl)-1H-imidazol-5-ylacetyl) amino-3(S)-methylpentyl]-N-1-naphthylmethyl-glycyl-methionine methyl ester N-[2(S)-(1-(1-Naphthylmethyl)-1H-imidazol-5-ylacetyl) amino-3(S)-methylpentyl]-N-1-naphthylmethyl-glycyl-methionine N-[2(S)-(1-(1-Naphthylmethyl)-1H-imidazol-5-ylacetyl) amino-3(S)-methylpentyl]-N-1-naphthylmethyl-glycyl-methionine methyl ester N-[2(S)-(1-Farnesyl-1H-imidazol-5-ylacetyl)amino-3(S)-methylpentyl]-N-1-naphthylmethyl-glycyl-methionine N-[2(S)-(1-Farnesyl-1H-imidazol-5-ylacetyl)amino-3(S)-methylpentyl]-N-1-naphthylmethyl-glycyl-methionine methyl ester N-[2(S)-(1-Geranyl-1H-imidazol-5-ylacetyl)amino-3(S)-methylpentyl]-N-1-naphthylmethyl-glycyl-methionine N-[2(S)-(1-Geranyl-1H-imidazol-5-ylacetyl)amino-3(S)-methylpentyl]-N-1-naphthylmethyl-glycyl-methionine methyl ester N-[2(S)-(1-(4-Pyridylmethyl)-1H-imidazol-4-ylacetyl) amino-3(S)-methylpentyl]-N-1-naphthylmethyl-glycyl-methionine N-[2(S)-(1-(4-Pyridylmethyl)-1H-imidazol-4-ylacetyl) amino-3(S)-methylpentyl]-N-1-naphthylmethyl-glycyl-methionine methyl ester N-[2(S)-(1-(4-Pyridylmethyl)-1H-imidazol-5-ylacetyl) amino-(3S)-methylpentyl]-N-1-naphthylmethyl-glycyl-methionine N-[2(S)-(1-(4-Pyridylmethyl)-1H-imidazol-5-ylacetyl) amino-3(S)-methylpentyl]-N-1-naphthylmethyl-glycyl-methionine methyl ester N-[2(S)-(1-(4-Cyanophenylmethyl)-1H-imidazol-5-ylacetyl)amino-3(S)-methylpentyl]-N-1-naphthylmethyl-glycyl-methionine N-[2(S)-(1-(4-Cyanophenylmethyl)-1H-imidazol-5-ylacetyl)amino-3(S)-methylpentyl]-N-1-naphthylmethyl-glycyl-methionine methyl ester N-[2(S)-(1-(4-Methoxyphenylmethyl)-1H-imidazol-5-ylacetyl)amino-3(S)-methylpentyl]-N-1-naphthylmethyl-glycyl-methionine N-[2(S)-(1-(4-Methoxyphenylmethyl)-1H-imidazol-5-ylacetyl)amino-3(S)-methylpentyl]-N-1-naphthylmethyl-glycyl-methionine methyl ester N-[2(S)-(1-(4-Quinolinylmethyl)-1H-imidazol-5-ylacetyl) amino-3(S)-methylpentyl]-N-1-naphthylmethyl-glycyl-methionine N-[2(S)-(1-(4-Quinolinylmethyl)-1H-imidazol-5-ylacetyl) amino-3(S)-methylpentyl]-N-1-naphthylmethyl-glycyl-methionine methyl ester N-[2(S)-(1-(2-Naphthylmethyl)-1H-imidazol-5-ylacetyl) amino-3(S)-methylpentyl]-N-1-phenylmethyl-glycyl-methionine N-[2(S)-(1-(2-Naphthylmethyl)-1H-imidazol-5-ylacetyl) amino-3(S)-methylpentyl]-N-1-phenylmethyl-glycyl-methionine methyl ester N-[2(S)-(1-(2-Naphthylmethyl)-1H-imidazol-5-ylethyl) amino-3(S)-methylpentyl]-N-1-naphthylmethyl-glycyl-methionine N-[2(S)-(1-(2-Naphthylmethyl)-1H-imidazol-5-ylethyl) amino-3(S)-methylpentyl]-N-1-naphthylmethyl-glycyl-methionine methyl ester 2(S)-[N-2(S)-(1-(2-Naphthylmethyl)-1H-imidazol-5-ylacetyl)amino-3(S)-methyl]pentyloxy-3-phenylpropionyl-methionine sulfone methyl ester 2(S)-[N-2(S)-(1-(2-Naphthylmethyl)-1H-imidazol-5-ylacetyl)amino-3(S)-methyl]pentyloxy-3-phenylpropionyl-methionine sulfone 2(S)-[N-2(S)-(1-(2-Naphthylmethyl)-1H-imidazol-5-ylethyl)amino-3(S)-methyl]pentyloxy-3-phenylpropionyl-methionine methyl ester 2(S)-[N-2(S)-(1-(2-Naphthylmethyl)-1H-imidazol-5-ylethyl)amino-3(S)-methyl]pentyloxy-3-phenylpropionyl-methionine N-[2(S)-(1-Methyl-1H-imidazol-4-ylacetyl)-amino-3(S)-methylpentyl]-N-(1-naphthylmethyl)-glycyl-methionine methyl ester N-[2(S)-(1-Methyl-1H-imidazol-4-ylacetyl)-amino-3(S)-methylpentyl]-N-(1-naphthylmethyl)-glycyl-methionine N-[2(S)-N-(2-Naphthylmethyl)-1H-imidazol-5-ylacetyl] amino-(3S)-methylpentyl]-N-(cyclopropylmethyl)-glycylmethionine methyl ester N-[(2S)-N-(2-Naphthylmethyl)-1H-imidazol-5-ylacetyl] amino-(3S)-methylpentyl]-N-(cyclopropylmethyl)-glycylmethionine N-[2(S)-[(5(R,S)-Methylpyroglutamyl)amino]-3(S)-methylpentyl]-N-(1-naphthylmethyl)-glycylmethionine methyl ester N-[2(S)-[(5(R,S)-Methylpyroglutamyl)amino]-3(S)-methylpentyl]-N-(1-naphthylmethyl)-glycylmethionine N-[2(S)-((N-Methylpyroglutamyl)amino)-3(S)-methylpentyl]-N-(1-naphthylmethyl)-glycyl-methionine N-[2(S)-((N-Methylpyroglutamyl)-amino)-3(S)-methylpentyl]-N-(1-naphthylmethyl)-glycyl-methionine methyl ester N-[2(S)-(N-Formylprolylamino)-3(S)-methylpentyl]-N-(1-naphthylmethyl)-glycyl-methionine methyl ester N-[2(S)-(N-Formylprolylamino)-3(S)-methylpentyl]-N-(1-naphthylmethyl)-glycyl-methionine N-[2(S)-(N'-(4-Nitrobenzyl)pyroglutamyl)-amino)-3(S)-methylpentyl]-N-(1-naphthylmethyl)-glycyl-methionine methyl ester N-[2(S)-(N'-(4-Nitrobenzyl)pyroglutamyl)-amino)-3(S)-methylpentyl]-N-(1-naphthylmethyl)-glycyl-methionine N-[2(S)-((N'-Benzylpyroglutamyl)amino)-3(S)-methylpentyl]-N-(1-naphthylmethyl)-glycyl-methionine methyl ester N-[2(S)-(N'-Benzylpyroglutamyl)amino)-3(S)-methylpentyl]-N-(1-naphthylmethyl)-glycyl-methionine N-[2(S)-1-(4-Fluorophenylmethyl)-1H-imidazol-5-ylacetyl)amino-3(S)-methylpentyl]-N-1-naphthylmethyl-glycyl-methionine methyl ester N-[2(S)-1-(4-Fluorophenylmethyl)-1H-imidazol-5-ylacetyl)amino-3(S)-methylpentyl]-N-1-naphthylmethyl-glycyl-methionine N-[2(S)-([1-(4-cyanobenzyl)-1H-imidazol-5-yl]acetylamino)-3(S)-methylpentyl]-N-(1-naphthylmethyl)glycyl-methionine isopropyl ester N-[2(S)-([1-(4-cyanobenzyl)-1H-imidazol-5-yl]acetylamino)-3(S)-methylpentyl]-N-(1-naphthylmethyl)glycyl-methionine sulfone methyl ester N-[2(S)-([1-(4-cyanobenzyl)-1H-imidazol-5-yl]acetylamino)-3(S)-methylpentyl]-N-(1-naphthylmethyl)glycyl-methionine sulfone N-[2(S)-([1-(4-cyanobenzyl)-1H-imidazol-5-yl]acetylamino)-3(S)-methylpentyl]-N-(1-naphthylmethyl)glycyl-(3-acetylamino)alanine methyl ester N-[2(S)-([1-(4-cyanobenzyl)-1H-imidazol-5-yl]acetylamino)-3(S)-methylpentyl]-N-(1-naphthylmethyl)glycyl-(3-acetylamino)alanine N-[2(S)-([1-(4-cyanobenzyl)-1H-imidazol-5-yl]acetylamino)-3(S)-methylpentyl]-N-(1-naphthylmethyl)glycyl-2(RS) amino-3-(2 thienyl)propionic acid methyl ester N-[2(S)-([1-(4-cyanobenzyl)-1H-imidazol-5-yl]acetylamino)-3(S)-methylpentyl]-N-(1-naphthylmethyl)glycyl-2(RS)-amino-3-(2 thienyl)propionic acid N-[2(S)-([1-(4-cyanobenzyl)-1H-imidazol-5-yl]acetylamino)-3(S)-methylpentyl]-N-(1-naphthylmethyl)glycyl-2(S) amino-4-sulfamylbutanoic acid methyl ester N-[2(S)-([1-(4-cyanobenzyl)-1H-imidazol-5-yl]acetylamino)-3(S)-methylpentyl]-N-(1-naphthylmethyl)glycyl-2(S) amino-4-sulfamylbutanoic acid N-[2(S)-([1-(4-cyanobenzyl)-1H-imidazol-5-yl]acetylamino)-3(S)-methylpentyl]-N-(1-naphthylmethyl)glycyl-N-methyl methionine methyl ester N-[2(S)-([1-(4-cyanobenzyl)-1H-imidazol-5-yl]acetylamino)-3(S)-methylpentyl]-N-(1-naphthylmethyl)glycyl-N-methyl methionine N-[2(S)-([1-(4-cyanobenzyl)-1H-imidazol-5-yl]acetylamino)-3(S)-methylpentyl]-N-(1-naphthylmethyl)glycyl-homoserine lactone N-[2(S)-([1-(4-cyanobenzyl)-1H-imidazol-5-yl]acetylamino)-3(S)-methylpentyl]-N-(1-naphthylmethyl)glycyl-homoserine N-[2(S)-([1-(4-cyanobenzyl)-1H-imidazol-5-yl]acetylamino)-3(S)-methylpentyl]-N-(1-naphthylmethyl)glycyl-proline methyl ester N-[2(S)-([1-(4-cyanobenzyl)-1H-imidazol-5-yl]acetylamino)-3(S)-methylpentyl]-N-(1-naphthylmethyl)glycyl-proline N-[2(S)-([1-(4-cyanobenzyl)-1H-imidazol-5-yl]acetylamino)-3(S)-methylpentyl]-N-(1-naphthylmethyl)glycyl-D-proline methyl ester N-[2(S)-([1-(4-cyanobenzyl)-1H-imidazol-5-yl]acetylamino)-3(S)-methylpentyl]-N-(1-naphthylmethyl)glycyl-D-proline N-[2(S)-([1-(4-cyanobenzyl)-1H-imidazol-5-yl]acetylamino)-3(S)-methylpentyl]-N-(1-naphthylmethyl)glycyl-L-pipecolinic acid N-[2(S)-([1-(4-carbomethoxybenzyl)-1H-imidazol-5-yl]acetylamino)-3(S)-methylpentyl]-N-(1-naphthylmethyl)glycyl-methionine methyl ester N-[2(S)-([1-(4-carbomethoxybenzyl)-1H-imidazol-5-yl]acetylamino)-3(S)-methylpentyl]-N-(1-naphthylmethyl)glycyl-methionine 1-(2-naphthylmethyl)-1H-imidazol-5-ylacetyl-isoleucinyl-phenylalaninyl-methionine methyl ester 1-(2-naphthylmethyl)-1H-imidazol-5-ylacetyl-isoleucinyl-phenylalaninyl-methionine or the pharmaceutically acceptable salts thereof.

Representative compounds of the invention are:

N-[2(S)-(1-(4-Nitrophenylmethyl)-1H-imidazol-5-ylacetyl)amino-3(S)-methylpentyl]-N-1-naphthylmethyl-glycyl-methionine

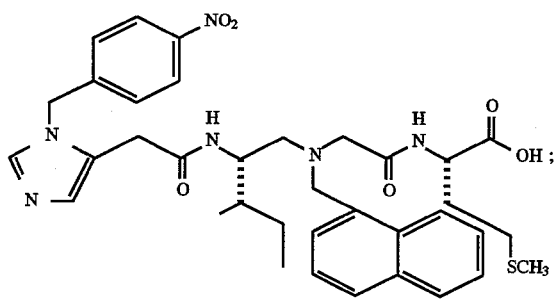

N-[2(S)-(1-(4-Nitrophenyl-methyl)-1H-imidazol-5-ylacetyl)amino-3(S)-methylpentyl]-N-1-naphthylmethyl-glycyl-methionine methyl ester

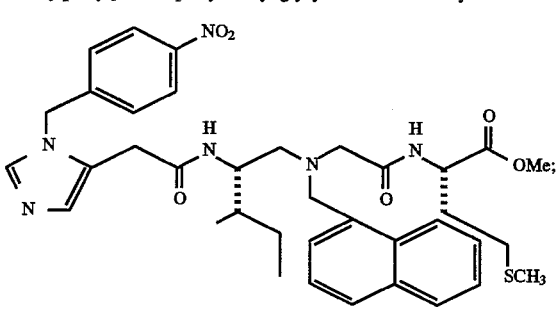

N-[2(S)-(1-(4-Cyanophenylmethyl)-1H-imidazol-5-ylacetyl)amino-3(S)-methylpentyl]-N-1-naphthylmethyl-glycyl-methionine

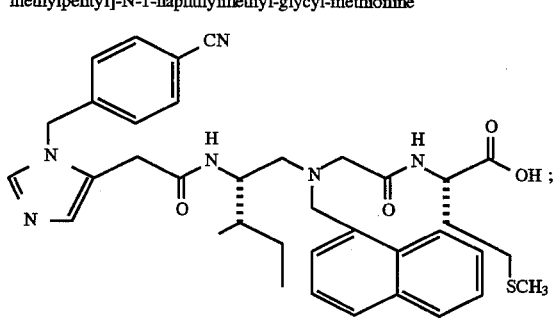

N-[2(S)-(1-(4-Cyanophenyl-methyl)-1H-imidazol-5-ylacetyl)amino-3(S)-methylpentyl]-N-1-naphthylmethyl-glycyl-methionine methyl ester

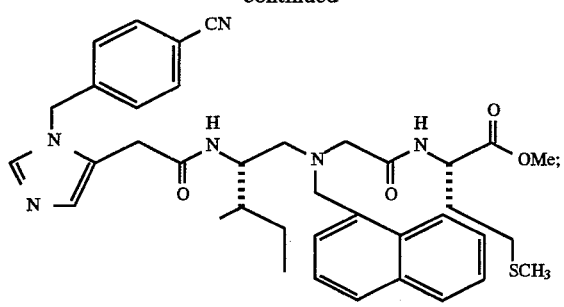

N-[2(S)-(1-(4-Cyanophenyl-methyl)-1H-imidazol-5-ylacetyl)amino-3(S)-methylpentyl]-N-1-naphthylmethyl-glycyl-methionine isopropyl ester

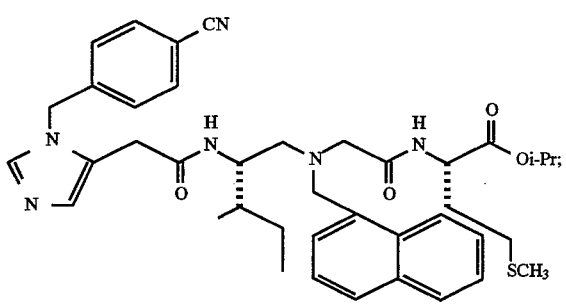

N-[2(S)-(1-(4-Methoxyphenylmethyl)-1H-imidazol-5-ylacetyl)amino-3(S)-methylpentyl]-N-1-naphthylmethyl-glycyl-methionine

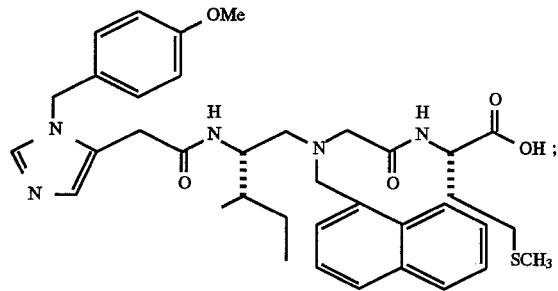

N-[2(S)-(1-(4-Methoxyphenyl-methyl)-1H-imidazol-5-ylacetyl)amino-3(S)-methylpentyl]-N-1-naphthylmethyl-glycyl-methionine methyl ester

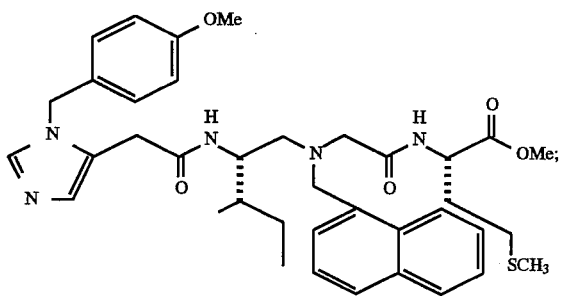

N-[2(S)-(1-(2-Naphthylmethyl)-1H-imidazol-5-ylacetyl)amino-3(S)-methylpentyl]-N-1-naphthylmethyl-glycyl-methionine

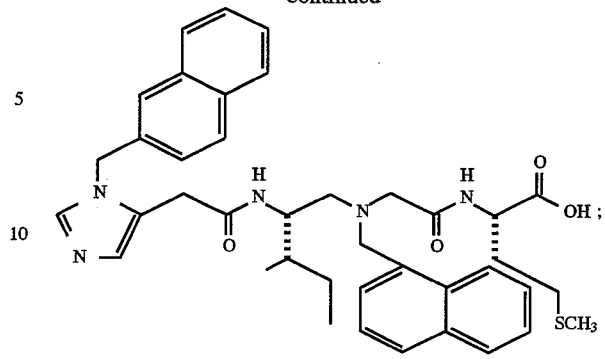

N-[2(S)-(1-(2-Naphthylphenyl-methyl)-1H-imidazol-5-ylacetyl)amino-3(S)-methylpentyl]-N-1-naphthylmethyl-glycyl-methionine methyl ester

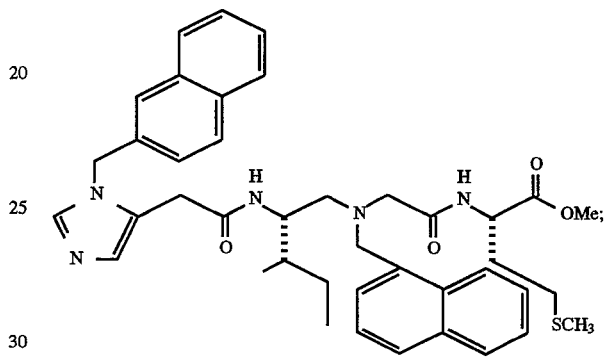

N-[2(S)-(1-(4-Cyanophenyl-methyl)-1H-imidazol-5-ylacetyl)amino-3(S)-methylpentyl]-N-1-naphthylmethyl-glycyl-methionine sulfone methyl ester

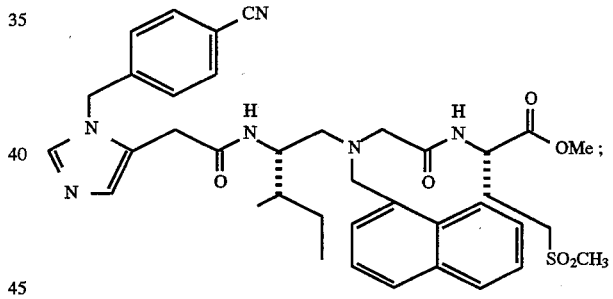

N-[2(S)-(1-(4-Cyanophenyl-methyl)-1H-imidazol-5-ylacetyl)amino-3(S)-methylpentyl]-N-1-naphthylmethyl-glycyl-methionine sulfone

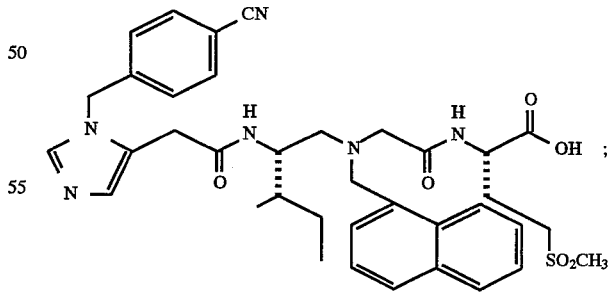

N-[2(S)-(1-(4-Cyanophenyl-methyl)-1H-imidazol-5-ylacetyl)amino-3(S)-methylpentyl]-N-1-naphthylmethyl-glycyl-2-(acetylamino)alanine methyl ester -continued

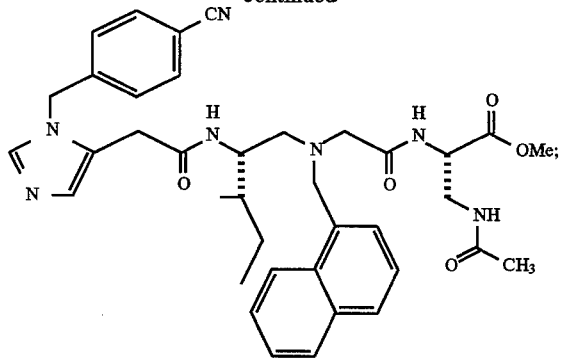

N-[2(S)-(1-(4-Cyanophenyl-methyl)-1H-imidazol-5-ylacetyl)amino-3(S)-methylpentyl]-N-1-naphthylmethyl-glycyl-2-(acetylamino)alanine methyl ester

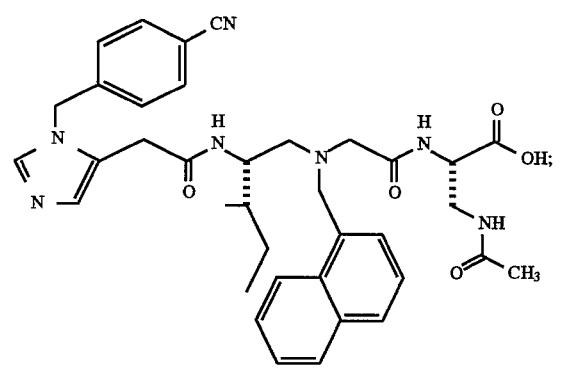

N-[2(S)-(1-(4-Cyanophenylmethyl)-1H-imidazol-5-ylacetyl)amino-3(S)-methylpentyl]-N-1-naphthylmethyl-glycyl-N-methyl-methionine

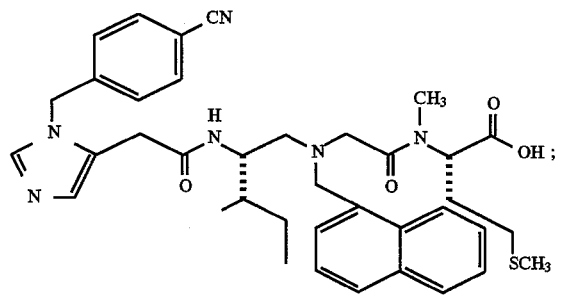

N-[2(S)-(1-(4-Cyanophenyl-methyl)-1H-imidazol-5-ylacetyl)amino-3(S)-methylpentyl]-N-1-naphthylmethyl-glycyl-N-methyl-methionine methyl ester

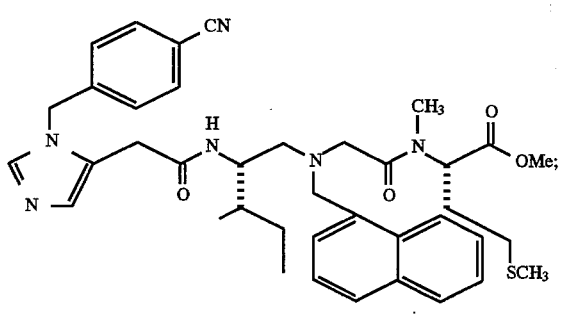

or the pharmaceutically acceptable salts thereof.

In the present invention, the amino acids which are disclosed are identified both by conventional 3 letter and single letter abbreviations as indicated below:

| Alanine | Ala | A |
|---|---|---|
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $NH_2$, $N(C_1-C_6\ alkyl)_2$, $CF_3$, $NO_2$, $(C_1-C_6\ alkyl)O-$, $-OH$, $(C_1-C_6\ alkyl)S(O)_m-$, $(C_1-C_6\ alkyl)C(O)NH-$, $H_2N-C(NH)-$, $(C_1-C_6\ alkyl)C(O)-$, $(C_1-C_6\ alkyl)OC(O)-$, $N_3$, CN, $(C_1-C_6\ alkyl)OC(O)NH-$ and $C_1-C_{20}$ alkyl.

The following structure:

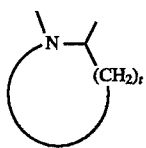

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

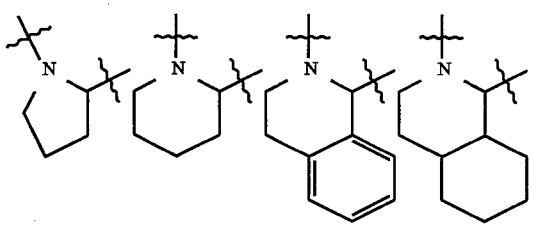

When $R^{2a}$ and $R^{2b}$ and $R^3$ and $R^4$ are combined to form $-(CH_2)_s-$, cyclic moieties are formed. Examples of such cyclic moieties include, but are not limited to:

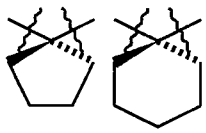

When $R^{5a}$ and $R^{5b}$ are combined to form $-(CH_2)_s-$, cyclic moieties as described hereinabove for $R^{2a}$ and $R^{2b}$ and $R^3$ and $R^4$ are formed. In addition, such cyclic moieties may optionally include a heteroatom(s). Examples of such heteroatom-containing cyclic moieties include, but are not limited to:

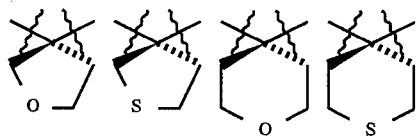

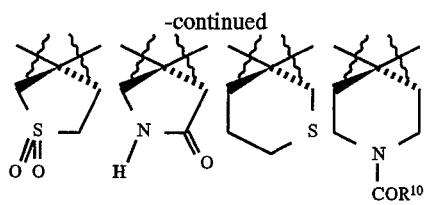

Preferably, $R^1$ is selected from: hydrogen, and $C_1-C_6$ alkyl.

Preferably, $R^{2a}$ and $R^{2b}$ are independently selected from: a side chain of a naturally occurring amino acid and $C_1-C_6$ alkyl unsubstituted or substituted with an aryl group.

Preferably, $R^3$ and $R^4$ are independently selected from: a side chain of a naturally occurring amino acid and $C_1-C_6$ alkyl unsubstituted or substituted with a group selected from aryl, heterocycle and $C_3-C_{10}$ cycloalkyl.

Preferably, $R^{5a}$ and $R^{5b}$ are independently selected from: a side chain of a naturally occurring amino acid, methionine sulfoxide, methionine sulfone and unsubstituted or substituted $C_1-C_6$ alkyl.

Preferably, X-Y is selected from:

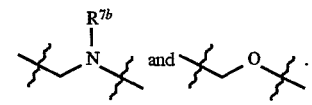

Preferably, $R^{7b}$ $C_1-C_6$ alkyl substituted with hydrogen or an unsubstituted or substituted aryl group.

Preferably, $R^8$ is selected from: hydrogen, perfluoroalkyl, F, Cl, Br, $R^{10}O-$, $R^{11}S(O)_m-$, CN, $NO_2$, $R^{10}C(O)-$, $R^{10}OC(O)-$, $-N(R^{10})_2$, $R^{11}OC(O)NR^{10}-$ and $C_1-C_6$ alkyl.

Preferably, $R^9$ is hydrogen.

Preferably, $R^{10}$ is selected from H, $C_1-C_6$ alkyl and benzyl.

Preferably, $A^1$ and $A^2$ are a bond.

Preferably, V is selected from hydrogen, heterocycle and aryl.

Preferably, n, p and r are independently 0, 1, or 2.

Preferably t is 3.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, $-N(R^{10})_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by lreductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes.

REACTION SCHEME A

Reaction A. Coupling of residues to form an amide bond

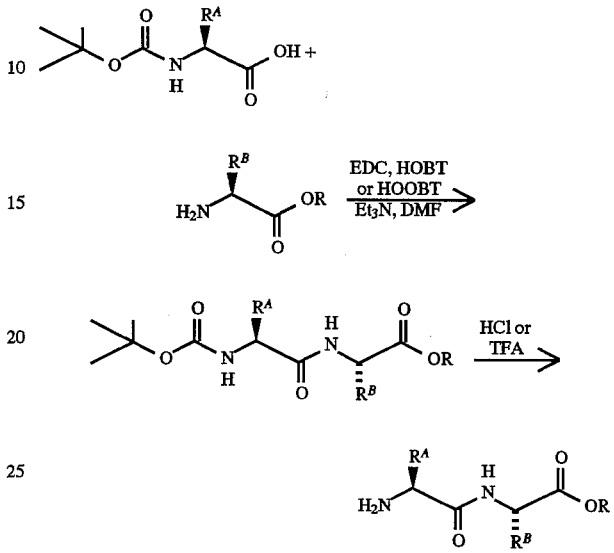

REACTION SCHEME B

Reaction B.

Preparation of reduced peptide subunits by reductive alkylation

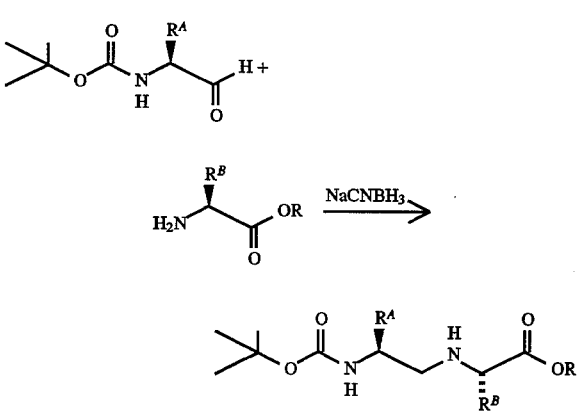

REACTION SCHEME C

Reaction C. Alkylation/reductive alkylation of reduced peptide subunits

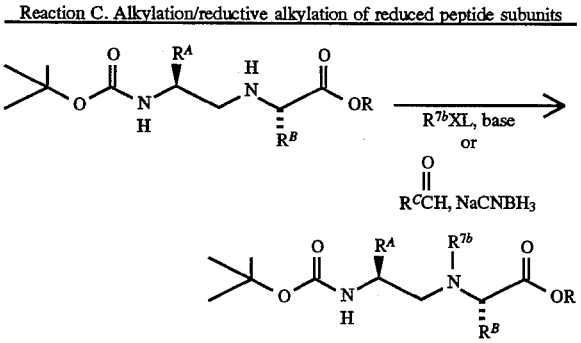

REACTION SCHEME D
Reaction D. Coupling of residues to form an amide bond

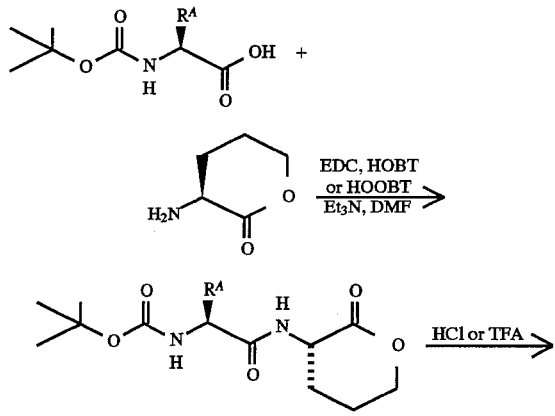

REACTION SCHEME E
Reaction E. Preparation of reduced dipeptides from peptides

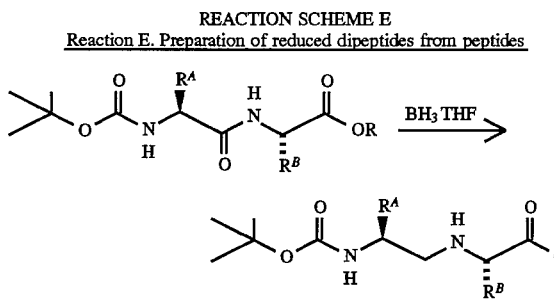

where $R^A$ and $R^B$ are $R^{2a}$, $R^{2b}$, $R^3$, $R^4$, $R^{5a}$ or $R^{5b}$ as previously defined; $X^L$ is a leaving group, e.g., Br⁻, I⁻ or MsO⁻; and $R^C$ is defined such that $R^{7b}$ is generated by the reductive alkylation process.

Reaction Schemes A–E illustrate bond-forming and peptide modifying reactions incorporating acyclic peptide units. It is well understood that such reactions are equally useful when the —NHC($R^A$)— moiety of the reagents and compounds illustrated is replaced with the following moiety:

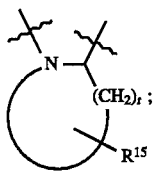

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme F, Step B, Part 1), and stereospecific boron triflouride or zinc chloride activated organo-magnesio, organo-lithio, or organo-zinc copper(I) cyanide $S_N2'$ displacement reaction (Scheme F, Step G). Through the use of optically pure N-Boc amino acids as starting material and these two key reactions, the stereo-chemistry of the final products is well defined. In Step H of Scheme F, $R^x$ is incorporated using coupling reaction A and $R^1$COOH; the alkylation reaction C using $R^x$CHO and a reducing agent; or alkylation reaction C using $R^x$CH$_2$X$^L$.

The alkane analogs are prepared in a similar manner by including an additional catalytic hydrogenation step as outlined in Reaction Scheme G.

REACTION SCHEME F

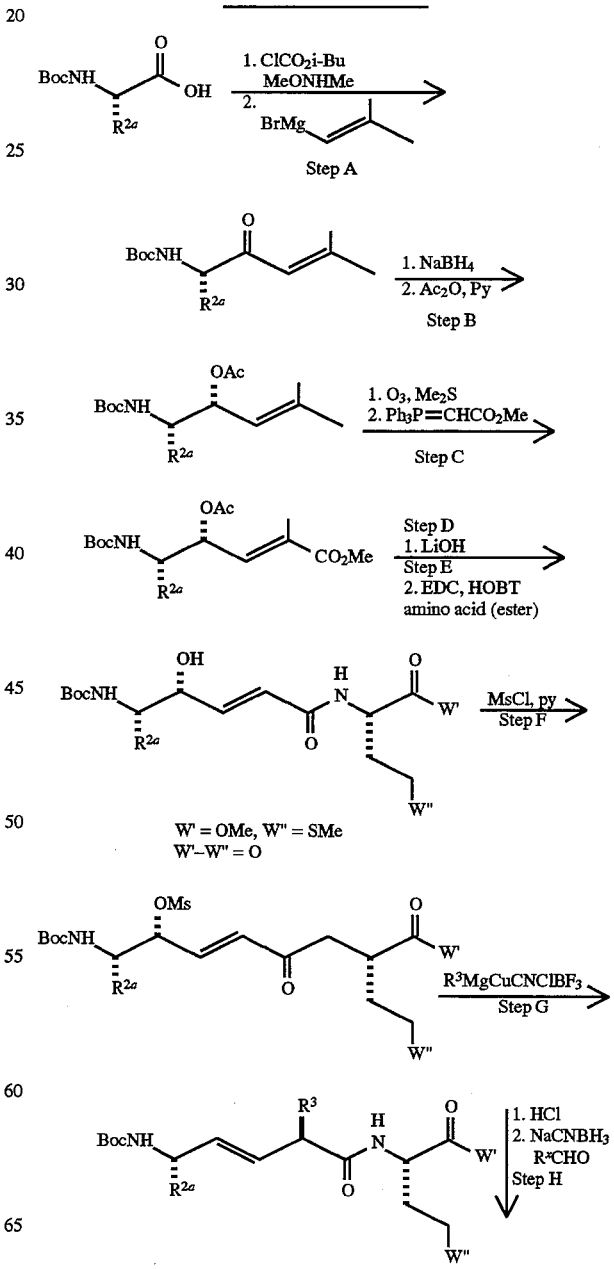

41
-continued
REACTION SCHEME F

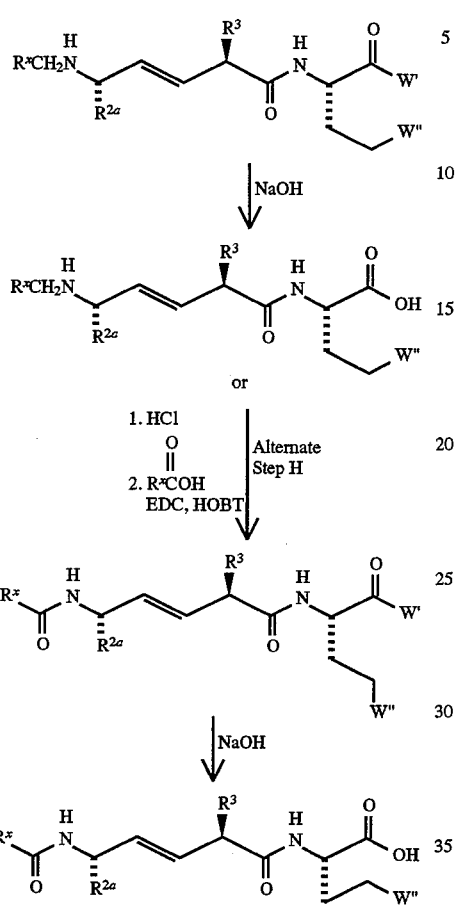

REACTION SCHEME G

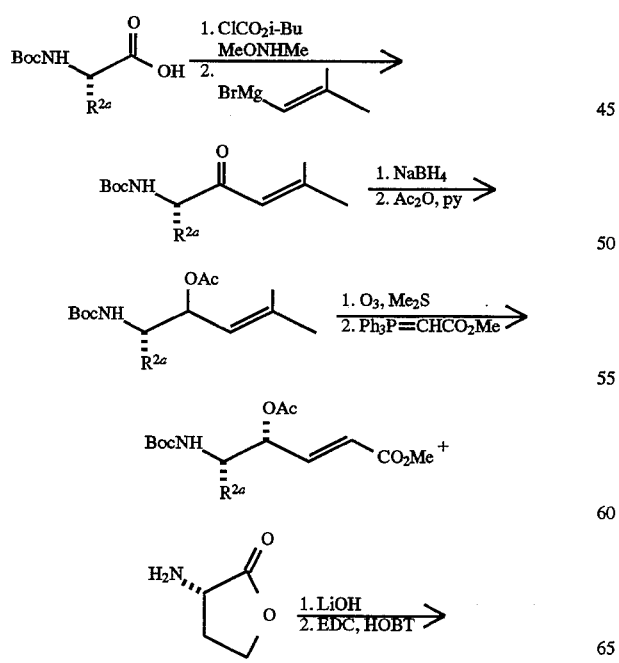

42
-continued
REACTION SCHEME G

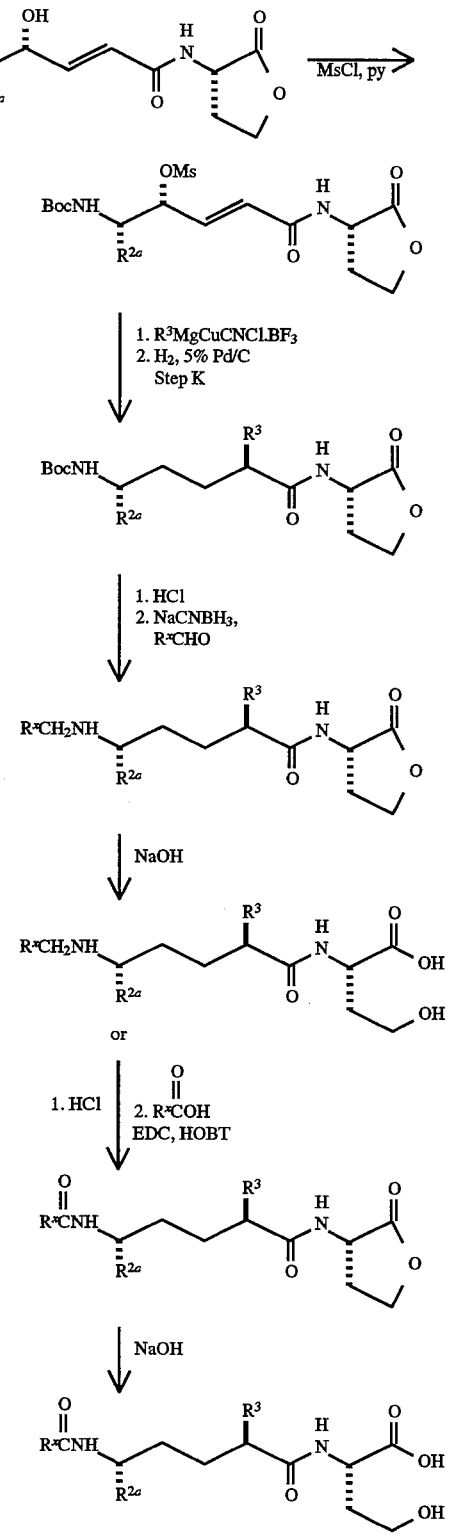

The oxa isostere compounds of this invention are prepared according to the route outlined in Scheme H. An aminoalcohol H-1 is acylated with alpha-chloroacetyl chloride in the presence of trialkylamines to yield amide H-2. Subsequent reaction of H-2 with a deprotonation reagent (e.g., sodium hydride or potassium t-butoxide) in an ethereal solvent such as THF provides morpholinone H-3. The N-Boc derivative H-4 is then obtained by the treatment of H-3 with BOC anhydride and DMAP (4-dimethylaminopyridine) in methylene chloride. Alkylation of H-4 with $R^3X^L$, where $X^L$ is a leaving group such as $Br^-$, $I^-$ or $Cl^-$ in THF/DME (1,2-dimethoxyethane) in the presence of a suitable base, preferably NaHMDS [sodium bis(trimethylsilyl)amide], affords H-5, which is retreated with NaHMDS followed by either protonation or the addition of an alkyl halide $R^4X$ to give H-6a or H-6b, respectively. Alternatively, H-6a can be prepared from H-4 via an aldol condensation approach. Namely, deprotonation of H-4 with NaHMDS followed by the addition of a carbonyl compound $R^yR^zCO$ gives the adduct H-7 (wherein $R^y$ and $R^z$ are selected such that $R^3$ is eventually provided. Dehydration of H-7 can be effected by mesylation and subsequent elimination catalyzed by DBU (1,8-diazabicyclo[5.4.0] undec-7-ene) or the direct treatment of H-7 with phosphorus oxychloride in pyridine to give olefin H-8. Then, catalytic hydrogenation of H-8 yields H-6a. Direct hydrolysis of H-6 with lithium hydrogen peroxide in aqueous THF will produce acid H-9b. Sometimes, it is more efficient to carry out this conversion via a 2-step sequence, namely, hydrolysis of H-6 in hydrochloric acid to afford H-9a, which is then derivatized with BOC-ON or BOC anhydride to give H-9b. The peptide coupling of acid H-9b with either an alpha-aminolactone (e.g., homoserine lactone, etc.) or the ester of an amino acid is carried out under the conditions exemplified in the previously described references to yield derivative H-10. Treatment of H-10 with gaseous hydrogen chloride gives H-11, which undergoes reductive alkylation in the presence of an aldehyde $R^xCHO$ (H-12) and a reducing agent (e.g., sodium cyanoborohydride); or acylation in the presence of $R^xCOOH$ (H-13) and a peptide coupling reagent affording the products H-14a and b. Hydrolysis of compounds H-14 to the corresponding hydroxy acids and acids, respectively, is accomplished by standard methods such as treatment with NaOH in alcoholic or aqueous milieux followed by careful acidifcation with dilute HCl.

SCHEME H

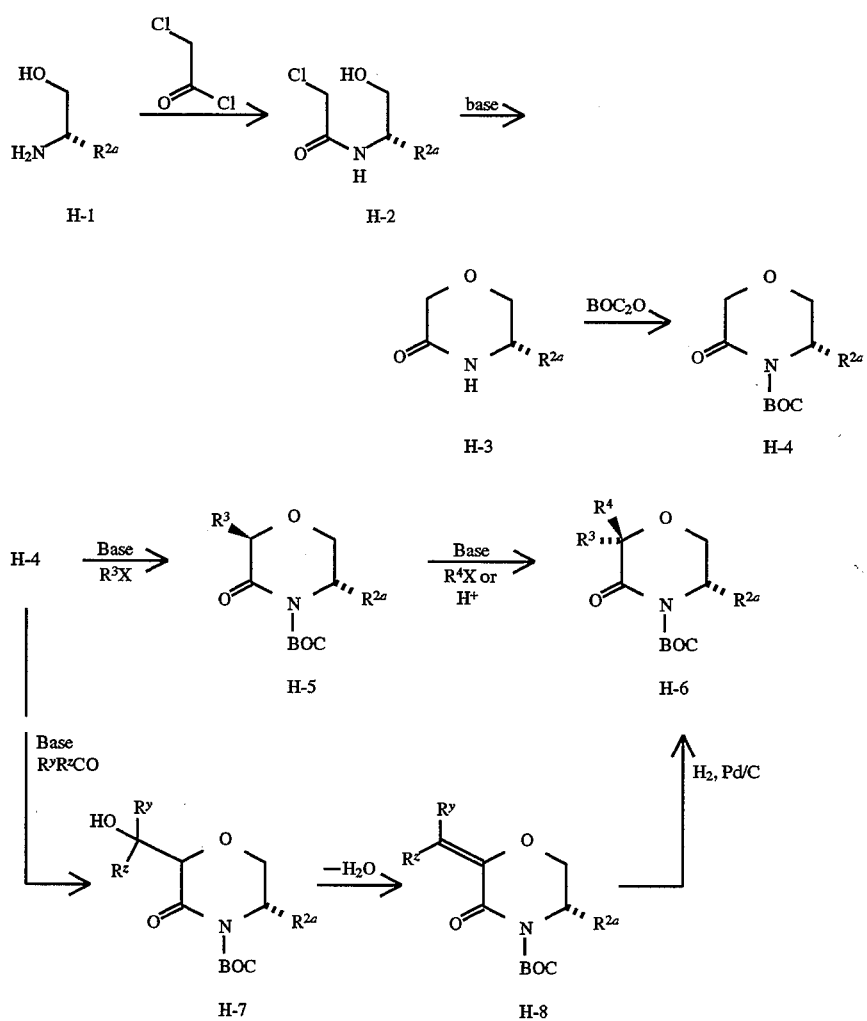

-continued
SCHEME H

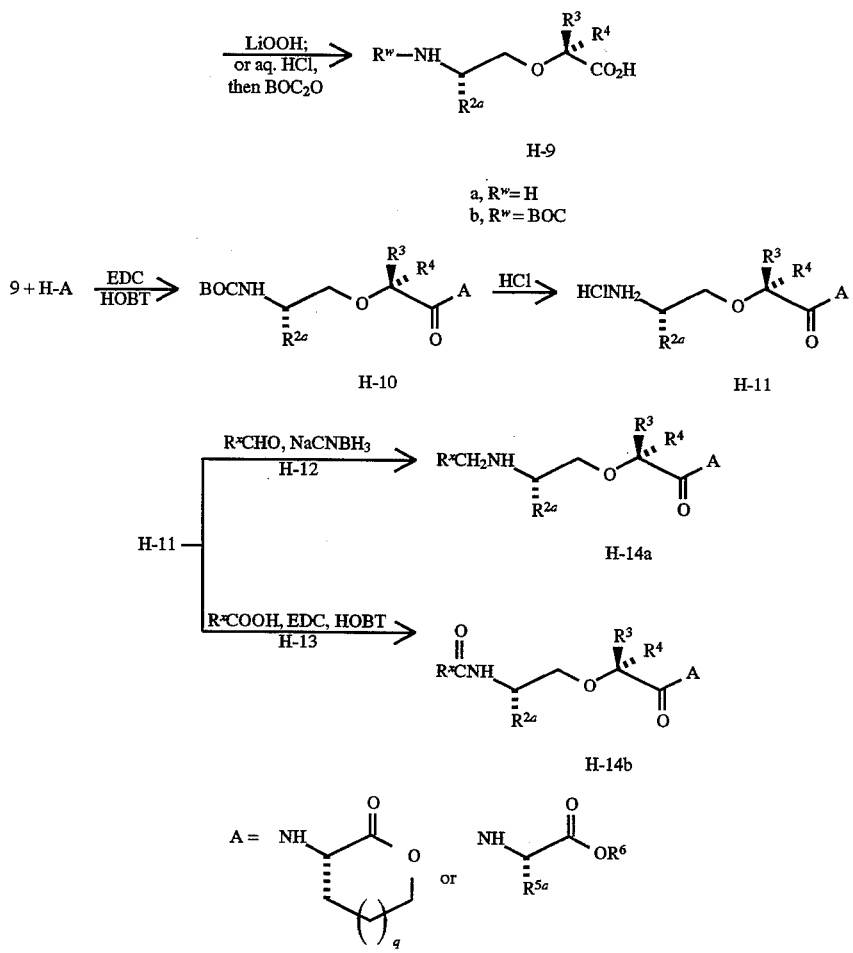

The thia, oxothia and dioxothia isostere compounds of this invention are prepared in accordance to the route depicted in Scheme I. Aminoalcohol I-1 is derivatized with $BOC_2O$ to give I-15. Mesylation of I-15 followed by reaction with methyl alpha-mercaptoacetate in the presence of cesium carbonate gives sulfide I-16. Removal of the BOC group in I-16 with TFA followed by neutralization with di-isopropylethylamine leads to lactam I-17. N-BOC derivative I-18 is obtained via the reaction of I-17 with BOC anhydride in THF catalyzed by DMAP. Sequential alkylation of I-18 with the alkyl halides $R^3X$ and $R^4X$ in THF/DME using NaHDMS as the deprotonation reagent produces I-19. Hydrolysis of I-19 in hydro-chloride to yield I-20a, which is derivatized with Boc anhydride to yield I-20b. The coupling of I-20b with an alpha-aminolactone (e.g., homoserine lactone, etc.) or the ester of an amino acid is carried out under conventional conditions as exemplified in the previously described references to afford I-21. Sulfide I-21 is readily oxidized to sulfone I-22 by the use of MCPBA (m-chloroperoxybenzoic acid). The N-BOC group of either I-21 or I-22 is readily removed by treatment with gaseous hydrogen chloride. The resultant amine hydrochloride I-23 undergoes reductive alkylation in the presence of an aldehyde $R^xCHO$ (I-12) and a reducing agent (e.g., sodium cyanoborohydride); or acylation in the presence of $R^xCOOH$ (I-13) and a peptide coupling reagent to afford the products I-24 and I-25.

SCHEME I

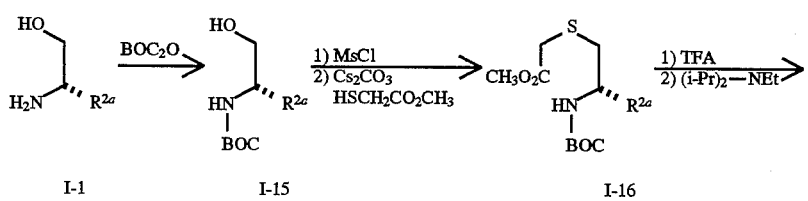

-continued
SCHEME I

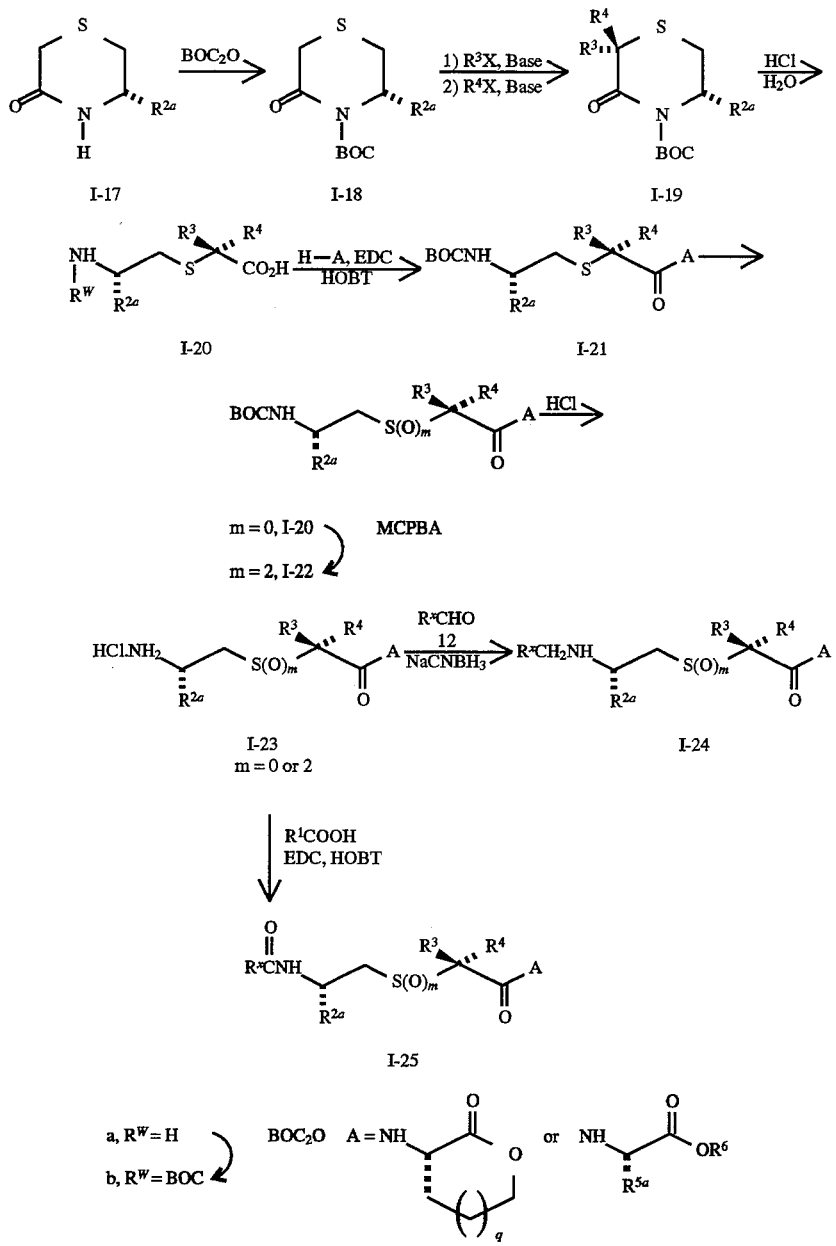

Reaction Schemes J–M illustrate reactions wherein the non-sulfhydryl-containing moiety at the N-terminus of the compounds of the instant invention is attached to an acyclic peptide unit which may be further elaborated to provide the instant compounds. These reactions may be employed in a linear sequence to provide the compounds of the invention or they may be used to synthesize fragments which are subsequently joined by the reactions described in Reaction Schemes A–E.

The intermediates whose synthesis are illustrated in Reaction Schemes A and C can be reductively alkylated with a variety of aldehydes, such as V, as shown in Reaction Scheme J. The aldehydes can be prepared by standard procedures, such as that described by O. P. Goel, U. Krolls, M. Stier and S. Kesten in *Organic Syntheses*, 1988, 67, 69–75, from the appropriate amino acid (Reaction Scheme J). The reductive alkylation can be accomplished at pH 5–7 with a variety of reducing agents, such as sodium triacetoxyborohydride or sodium cyanoborohydride in a solvent such as dichloroethane, methanol or dimethylformamide. The product VI can be deprotected to give the final compounds VII with trifluoroacetic acid in methylene chloride. The final product VII is isolated in the salt form, for example, as a trifluoroacetate, hydrochloride or acetate salt, among others. The product diamine VII can further be selectively protected to obtain VIII, which can subsequently be reductively alkylated with a second aldehyde to obtain IX. Removal of the protecting group, and conversion to cyclized products such as the dihydroimidazole XI can be accomplished by literature procedures.

Alternatively, the protected dipeptidyl analog intermediate can be reductively alkylated with other aldehydes such as 1-trityl-4-carboxaldehyde or 1-trityl-4-imidazolylacetaldehyde, to give products such as XII (Reaction Scheme K). The trityl protecting group can be removed from XII to give XIII, or alternatively, XII can first be treated with an alkyl halide then subsequently deprotected to give the alkylated imidazole XIV. Alternatively, the dipeptidyl analog intermediate can be acylated or sulfonylated by standard techniques.

The imidazole acetic acid XV can be converted to the acetate XVII by standard procedures, and XVII can be first reacted with an alkyl halide, then treated with refluxing methanol to provide the regiospecifically alkylated imidazole acetic acid ester XVIII. Hydrolysis and reaction with the protected dipeptidyl analog intermediate in the presence of condensing reagents such as 1-(3-dimethylaminopropyl)-3-ethylcarbodiimide (EDC) leads to acylated products such as XIX.

Similar procedures as are illustrated in Reaction Schemes J–M may be employed using other peptidyl analog intermediates such as those whose synthesis is illustrated in Reaction Schemes B–I.

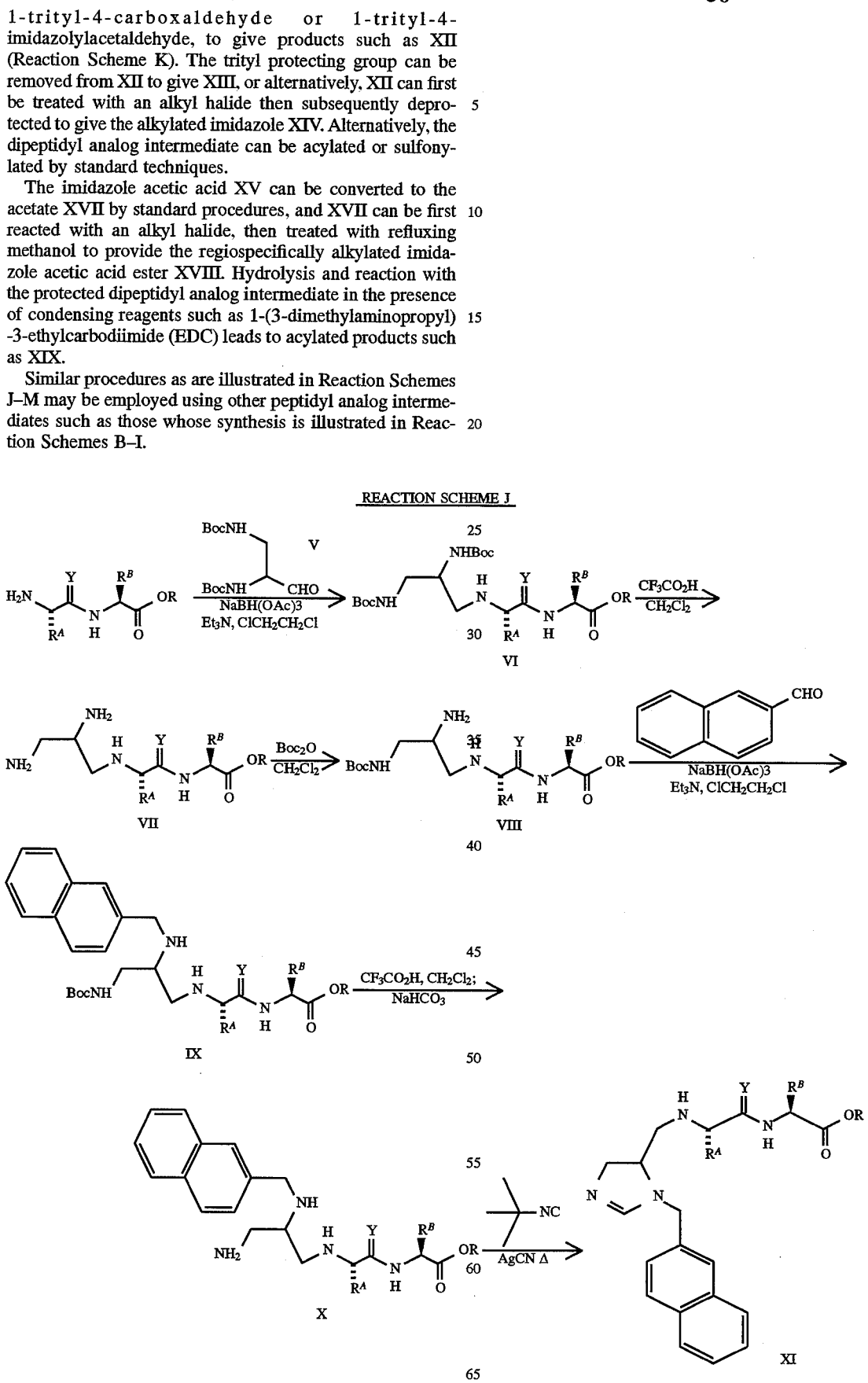

REACTION SCHEME K

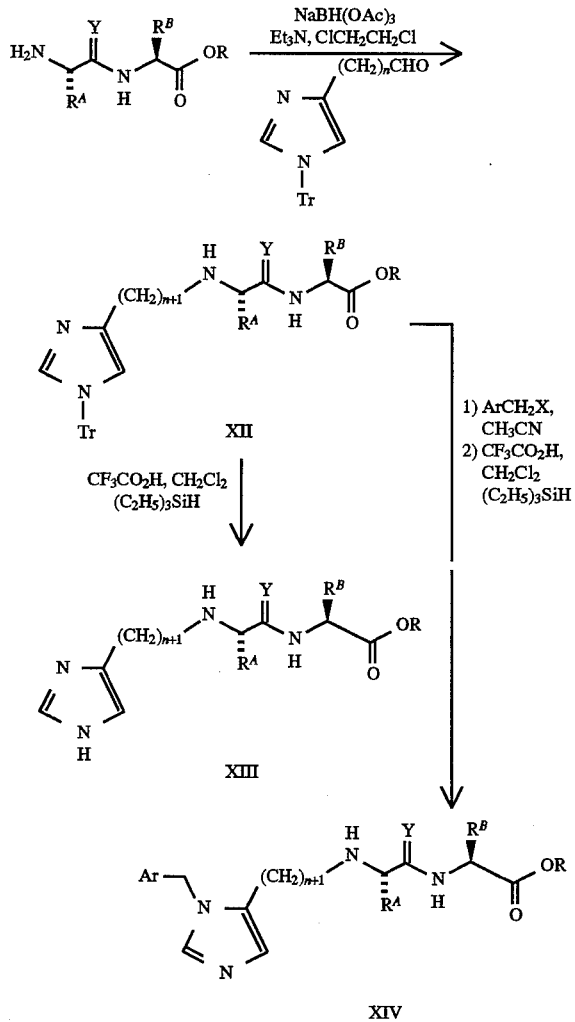

REACTION SCHEME L

REACTION SCHEME M

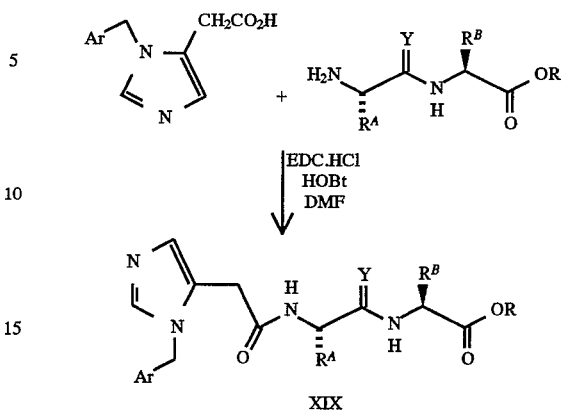

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention are also useful for inhibiting proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the benign proliferative disorder neurofibromatosis, or tumors in which the Ras is activated due to mutation or overexpression of tyrosine kinase oncogenes (e.g., neu, src, abl, lck, and fyn) may be inhibited by the compounds of this invention. Furthermore, arteriosclerosis and diabetic disturbance of blood vessels may be prevented or treated by use of the instant compounds to inhibit proliferation of vascular smooth muscle cells.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

Preparation of N-[2(S)-(1-(Phenylmethyl)-1H-imidazol-4-ylacetyl)amino-3(S)-methylpentyl]-N-1-naphthylmethyl-glycyl-methionine Bis Trifluoroacetate (13) and N-[2(S)-(1-(Phenylmethyl)-1H-imidazol-5-ylacetyl)amino-3(S)-methylpentyl]-N-1-naphthylmethyl-glycyl-methionine Bis Trifluoroacetate (14)

Step A: Preparation of 1H-Imidazole-4-acetic acid methyl ester-hydrochloride (1)

Into a solution of 1H-imidazole-4-acetic acid hydrochloride (4 g, 24.6 mmol) in methanol (100 ml) was bubbled hydrogen chloride gas until saturated. This solution was allowed to stand for 18 h at room temperature and the solvent evaporated in vacuo to give (1) as a white solid.

$^1$H NMR (CDCl$_3$, 400 MHz) δ 8.85 (1H, s), 7.45 (1H, s), 3.89 (2H, s) and 3.75 (3H, s) ppm.

Step B: Preparation of 1-(Phenylmethyl)-1H-imidazol-4-ylacetic acid methyl ester (2) and 1-(Phenylmethyl)-1H-imidazol-5-ylacetic acid methyl ester (3) (3:1 mixture)

To a solution of sodium hydride (37.3 mg, 1.56 mmol) in dimethylformamide (2 ml) cooled to 0° C. (ice bath) was added, via cannula, a solution of 1 (115 mg, 0.707 mmol) in dimethylformamide (3 ml). This suspension was allowed to stir at 0° C. for 15 min. To this suspension was added benzyl bromide (84 µL, 0.707 mmol) and the mixture was stirred at room temperature for 2 h. After this time, the mixture was quenched with sat. aq. sodium bicarbonate (15 ml) and water (20 ml) and extracted with methylene chloride (2×50 ml). The combined extracts were washed with brine (20 ml), dried (MgSO$_4$), filtered and the solvent was evaporated in vacuo. The residue was purified by flash chromatography eluting with acetonitrile to give a 3:1 mixture of 2 and 3.

$^1$H NMR (CDCl$_3$, 400 MHz) δ 7.53 (0.25H, s), 7.48 (0.75H, s), 7.35 (3H, m), 7.18 (1.5H, d, J=7.4 Hz), 7.06 (0.5H, d, J=7.2 Hz), 7.00 (0.25H, s), 6.87 (0.75H, s), 5.16 (0.5H, s), 5.08 (1.5H, s), 3.72 (1.5H, s), 3.65 (2.25H, s), 3.63 (0.75H, s) and 3.48 (0.5H, s) ppm.

Step C: Preparation of 1-(Phenylmethyl)-1H-imidazol-4-ylacetic acid hydrochloride (4) and 1-(Phenylmethyl)-1H-imidazol-5-ylacetic acid hydrochloride (5) (3:1 mixture)

A solution of 2 and 3 (3:1 mixture, 106 mg) in 1.0N HCl (3 ml) was heated to 45° C. for 4 h. After this time, the solution was evaporated in vacuo to give a 3:1 mixture of 4 and 5.

$^1$H NMR (DMSO, 400 MHz) δ 9.26 (0.75H, s), 9.23 (0.25H, s), 7.60 (0.25H, m), 7.58 (0.75H, s), 7.45-7.26 (5H, m), 5.43 (0.5H, s), 5.41 (0.5H, s), 3.77 (1.5H, s), 3.75 (0.5H, s) ppm.

Step D: Preparation of N-(2(S)-(t-butoxycarbonylamino)-3 (S)-methylpentyl)glycine methyl ester (6)

Glycine methyl ester hydrochloride (4.41 g, 0.035 mol) was dissolved in 1,2-dichloroethane (50 mL) and DMF (5 mL) and treated with 3A molecular sieves (10 g) and N-t-butoxycarbonyl-isoleucinal (6.3 g, 0.029 mol) with stirring at 0° C. Sodium triacetoxyborohydride (9.27 g, 0.044 mol) was added, and the pH of the mixture was adjusted to 6 with triethylamine (3 mL, 0.022 mol). After stirring for 18 h the mixture was filtered, concentrated to a small volume and partitioned between EtOAc and water. The aqueous layer was extracted with EtOAc (2×50 mL). The combined organic phase was washed with aqueous saturated NaHCO$_3$ solution, brine, and dried (Na$_2$SO$_4$). Filtration and concentration afforded a residue which was purified by flash chromatography (SiO$_2$, EtOAc:hexane, 1:3) to give (6).

$^1$H NMR (CDCl$_3$) δ 4.69 (1H, m), 3.72 (3H, s), 3.48–3.62 (1H, m), 3.42 (2H, ABq), 2.65 (2H, d, J=6 Hz), 1.4–1.6 (2H, m), 1.48 (9H, s), 1.04–1.2 (1H, m), 0.85–0.95 (6H, m) ppm.

Step E: Preparation of N-[2(S)-(t-Butoxycarbonylamino)-3 (S)-methylpentyl]-N-(1-naphthylmethyl)glycine methyl ester (7)

N-[2(S)-(t-Butoxycarbonylamino)-3(S)-methyl-pentyl] glycine methyl ester (6, 2.00 g, 6.97 mmol) was dissolved in 1,2-dichloroethane (56 ml) and 3A molecular sieves were added followed by 1-naphthaldehyde (1.89 ml, 13.9 mmol) and sodium triacetoxy-borohydride (6.65 g, 31.4 mmol). The mixture was stirred at ambient temperature for 16 h, and filtered through glass fiber paper and concentrated. The residue was partitioned between EtOAc and sat. NaHCO$_3$ (100 ml/25 ml). The aqueous layer was extracted with EtOAc (3×50 ml). The organic layers were combined, dried (Na$_2$SO$_4$), filtered, and concentrated to give 5.0 g of crude product which was purified by chromatography (SiO$_2$, 15–33% ethyl acetate/hexane) to give 7.

$^1$H NMR (CD$_3$OD) δ 8.44-8.38 (1H, d, J=6 Hz), 7.88-7.77 (2H, m,), 7.55-7.35 (4H, m), 6.34-6.27 (1H, m), 4.25 (2H, ABq), 3.66 (3H, s), 3.40-3.23 (1H, m), 2.90 (1H, dd, J=6 and 15 Hz), 2.63 (1H, dd, J=6 and 15 Hz), 1.57-1.46 (1H, m), 1.43 (9H, s), 1.34-1.18 (2H, m), 1.06-0.85 (1H, m) and 0.85-0.71 (6H, m) ppm.

Step F: Preparation of N-[2(S)-(t-Butoxycarbonylamino)-3 (S)-methylpentyl]-N-(1-naphthylmethyl)glycine (8)

N-[2(S)-(t-Butoxycarbonylamino)-3(S)-methylpentyl]-N-(1-naphthylmethyl)glycine methyl ester (7, 2.61 g, 6.10 mmol) was dissolved in MeOH (50 ml) and 1N NaOH (24.4 ml, 24.4 mmol) was added. The mixture was stirred at ambient temperature for 4 h and concentrated. The resulting residue was dissolved in water (25 ml) and neutralized with 1N HCl (24.4 ml). The aqueous layer was washed with EtOAc (3×50 ml). The organic layers were combined, dried with Na$_2$SO$_4$, filtered, and concentrated to give the product.

$^1$H NMR (CD$_3$OD) δ 8.43 (1H, d, J=6 Hz), 7.97 (2H, t, J=6 Hz) 7.75-7.48 (4H, m), 4.96 (1H, d, J=12 Hz), 4.72 (1H, d, J=12 Hz), 3.80-3.58 (3H, m), 3.49-3.40 (1H, dd,, J=3 and 12 Hz), 3.03 (1H, dd, J=3 and 12 Hz), 1.42 (9H, s,), 1.37-1.28 (2H, m), 1.80-1.00 (1H, m), 0.94-0.78 (6H, m,) ppm.

Step G: Preparation of N-[2(S)-(t-Butoxycarbonylamino)-3 (S)-methylpentyl]-N-(1-naphthylmethyl)glycine-methionine methyl ester (9)

N-[2(S)-(t-Butoxycarbonylamino)-3(S)-methylpentyl]-N-(1-naphthylmethyl)glycine (8, 2.29 g, 5.53 mmol), dissolved in DMF (20 mL), was treated with HOBT (0.822 g, 6.08 mmol), EDC (1.17 g, 6.08 mmol), and methionine methyl ester hydrochloride (1.21 g, 6.08 mmol). The pH was adjusted to 7.5 with Et$_3$N (1.7 mL, 12 mmol) and the mixture was stirred at ambient temperature for 24 h. The mixture was concentrated, and the residue was partitioned between EtOAc (50 mL) and saturated NaHCO$_3$ solution (25 mL). The aqueous layer was extracted with EtOAc (1×30 mL). The organic layers were combined, washed with brine (1×25 mL), dried (Na$_2$SO$_4$), filtered, and concentrated to give 3.2 g of crude product which was purified by chromatography (silica gel eluting with 1:3 to 1:2 ethyl acetate in hexane) to give pure product. $^1$H NMR (CD$_3$OD) δ 8.33 (1H, d, J=6 Hz), 7.90 (1H, d, J=6 Hz), 7.82 (1H, d, J=6 Hz), 7.61-7.39 (4H, m), 6.60-6.52 (1H, m), 4.32-4.06 (2H, m), 3.90-3.69 (1H, m), 3.65 (3H, s), 3.27-3.14 (2H, m), 2.93-2.70 (2H, m), 2.19-1.78 (6H, m), 1.63-1.30 (13H, m), 1.19-1.05 (1H, m), 0.95-0.81 (6H, m) ppm.

Step H: Preparation of N-(2(S)-amino-3(S)-methylpentyl)-N-(1-naphthylmethyl)-glycyl-methionine methyl ester hydrochloride (10)

N-[2(S)-(t-Butoxycarbonylamino)-3(S)-methylpentyl]-N-(1-naphthylmethyl)-glycyl-methionine methyl ester (9, 2.82 g, 5.04 mmol) was dissolved in EtOAc (50 mL) and cooled to −25° C. HCl was bubbled through the mixture until TLC (95:5 CH$_2$Cl$_2$:MeOH) indicated complete reaction. Nitrogen was bubbled through the mixture to remove excess HCl and the mixture was then concentrated to give the title compound.

$^1$H NMR (CD$_3$OD) δ 8.31 (1H, d, J=6 Hz), 7.96 (2H, d, J=6 Hz), 7.83-7.71 (1H, m), 7.68-7.49 (3H, m), 4.76-4.55 (4H, m), 3.84-3.75 (2H, m), 3.71 (3H, s), 3.70-3.59 (1H, m), 3.21-3.00 (2H, m), 2.57-2.38 (3H, m), 2.17-2.04 (4H, m), 1.97-1.81 (1H, m), 1.63-1.50 (1H, m), 1.39-1.20 (1H, m), 1.19-1.00 (1H, m), 0.95-0.79 (6H, m) ppm.

Step I: Preparation of N-[2(S)-(1-(Phenylmethyl)-1H-imidazol-4-ylacetyl)amino-3(S)-methylpentyl]-N-1-naphthylmethyl-gylycyl-methionine methyl ester bis trifluoroacetate (11) and N-[2(S)-(1-(Phenylmethyl)-1H-imidazol-5-ylacetyl)-amino-3(S)-methylpentyl]-N-1-naphthylmethyl-glycyl-methionine methyl ester bis trifluoroacetate (12)

To a solution of a 1-(phenylmethyl)-1H-imidazol-4-ylacetic acid hydrochloride (4) and 1-(phenylmethyl)-1H-imidazol-5-ylacetic acid hydrochloride (5, 3:1 mixture, 115 mg, 0.455 mmol), N-[2(S)-amino-3(S)-methylpentyl]-N-1-naphthylmethyl-glycyl-methionine methyl ester bis hydrochloride (10, 244 mg, 0.455 mmol) and 3-hydroxy-1,2,3-benzotriazin-4(3H)-one (HOOBT, 74 mg, 0.46 mmol) in dimethylformamide (5 ml) was added 1-(3-dimethylaminopropyl)-3-ethylcarbodiimide hydrochloride (EDC, 87 mg, 0.455 mmol) and triethylamine (190 µl, 1.36 mmol) and the solution stirred overnight. After this time, sat. aq. sodium bicarbonate (20 ml) and water (25 ml) were added and the mixture was extracted with ethyl acetate (2×50 ml). The combined extracts were washed with brine (5 ml) and the solvent evaporated in vacuo. The regioisomers were separated by Prep HPLC using a Nova Prep 5000 Semi preparative HPLC system and a Waters PrepPak cartridge (47×300 mm, C18, 15 um, 100A) eluting with 5–95% acetonitrile/water (0.1% TFA) at 100 ml/min (chromatography method A) to give after lyophilization pure 11 and 12.

11:

$^1$H NMR (CD$_3$OD, 400 MHz) δ 8.95 (1H, s), 8.27 (1H, m), 7.96 (2H, m), 7.68 (1H, d), 7.60-7.37 (9H, m), 5.38 (2H, s), 5.0-4.8 (1H, m), 4.52 (1H, t, J=10.6 Hz), 4.42 (1H, dd, J=4 and 6.6 Hz), 4.14 (1H, m), 3.92 (1H, d, J=13.3 Hz), 3.83 (1H, d, J=13.3 Hz), 3.70 (1H, s), 3.64 (1H, m), 3.54 (2H, m), 3.22 (1H, dd, J=7 and 8 Hz), 2.37 (1H, m), 2.10 (1H, m), 2.00 (3H, s), 1.98 (1H, m), 1.79 (1H, m), 1.58 (1H, m), 1.42 (1H, m), 1.17 (1H, m) and 0.90 (6H, m) ppm. Anal. Calcd for C$_{37}$H$_{47}$N$_5$O$_4$S.3.0 TFA.0.15 H$_2$O: C, 51.51; H, 5.06; N, 6.98. Found: C, 51.52; H, 4.98; N, 7.18. FAB HRMS exact mass calcd for C$_{37}$H$_{48}$N$_5$O$_4$S 658.342702 (MH$^+$), found 658.341278.

12:

$^1$H NMR (CD$_3$OD, 400 MHz) δ 8.8 (1H, s), 8.26 (1H, m), 7.89 (2H, m), 7.66-7.24 (8H, m), 7.21 (2H, s), 5.36 (2H, m), 4.37 (3H, m), 4.09 (1H, br s), 3.66 (3H, s), 3.56 (3H, m), 3.50-2.90 (3H, m), 2.27 (1H, br s), 2.20 (1H, br s), 1.96 (3H, s), 1.90 (1H, br s), 1.68 (1H, br s), 1.58 (1H, br s), 1.40 (1H, m), 1.18 (1H, m) and 0.89 (6H, m) ppm. Anal. Calcd for $C_{37}H_{47}N_5O_4S·1.85$ TFA·0.10 $H_2O$: C, 56.15; H, 5.68; N, 8.04. Found: C, 56.14; H, 5.62; N, 8.44. FAB HRMS exact mass calcd for $C_{37}H_{48}N_5O_4S$ 658.342702 ($MH^+$), found 658.343754.

Step J: Preparation of N-[2(S)-(1-(Phenylmethyl)-1H-imidazol-4-ylacetyl)amino-3(S)-methylpentyl]-N-1-naphthylmethyl-glycyl-methionine bis trifluoroacetate (13) and N-[2(S)-(1-(Phenylmethyl)-1H-imidazol-5-ylacetyl) amino-3(S)-methylpentyl]-N-1-naphthylmethyl-glycyl-methionine bis trifluoroacetate (14)

To a solution of N-[2(S)-(1-(Phenylmethyl)-1H-imidazol-4-ylacetyl)amino-3(S)-methylpentyl]-N-1-naphthylmethyl-glycyl-methionine methyl ester bis trifluoroacetate (11) and N-[2(S)-(1-(phenylmethyl)-1H-imidazol-5-yl)acetyl)amino-3(S)-methylpentyl]-N-1-naphthylmethyl-glycyl-methionine methyl ester bis trifluoroacetate (12, 2:1 mixture, 50 mg, 0.057 mmol) in methanol (5 ml) was added 1.0N lithium hydroxide (570 µl, 0.547 mmol). This solution was stirred for 4 h and treated with trifluoroacetic acid (100 µl). This mixture was purified by preparative HPLC using chromatography method A to give the title compounds.

13:
$^1$H NMR ($CD_3OD$, 400 MHz) δ 8.83 (1H, s), 8.21 (1H, d, J=9.5 Hz), 7.88 (2H, m), 7.54 (1H, d, J=6.9 Hz), 7.5-7.3 (9H, m), 5.32 (2H, s), 4.56 (1H, br d, J=10 Hz), 4.36 (2H, m), 4.09 (1H, m), 3.55 (4H, m), 3.17 (1H, br d, J=10 Hz), 2.98 (1H, t, J=10 Hz), 2.29 (1H, m), 2.18 (1H, m), 1.96 (1H, m), 1.95 (3H, s), 1.67 (1H, m), 1.56 (1H, m), 1.37 (1H, m), 1.11 (1H, m) and 0.88 (6H, m) ppm. Anal. Calcd for $C_{36}H_{45}N_5O_4S·2.15$ TFA: C, 54.45; H, 5.35; N, 7.88. Found: C, 54.42; H, 5.30; N, 7.97. FAB HRMS exact mass calcd for $C_{36}H_{46}N_5O_4S$ 644.327052 ($MH^+$), found 644.326691.

14:
$^1$H NMR ($CD_3OD$, 400 MHz) δ 8.80 (1H, s), 8.29 (1H, m), 7.92 (2H, m), 7.61 (1H, br), 7.32–7.53 (7H, m), 7.21 (2H, br s), 5.37 (2H, s), 4.37 (2H, m), 4.08 (1H, m), 3.57 (4H, br m), 3.05 (2H, m), 2.29 (2H, m), 2.20 (1H, m), 1.96 (3H, s), 1.70 (1H, m), 1.62 (1H, m), 1.57 (1H, m), 1.39 (1H, m), 1.13 (1H, m) and 0.88 (6H, m) ppm. FAB HRMS exact mass calcd for $C_{36}H_{46}N_5O_4S$ 644.327052 ($MH^+$), found 644.327917.

EXAMPLE 2

Preparation of N-[2(S)-(1-(4-Nitrophenylmethyl)-1H-imidazol-4-ylacetyl)amino-3(S)-methylpentyl]-N-1-naphthylmethyl-glycyl-methionine Bis Trifluoroacetate (21) and N-[2(S)-(1-(4-Nitrophenylmethyl)-1H-imidazol-5-ylacetyl)amino-3 (S)-methylpentyl]-N-1-naphthylmethyl-glycyl-methionine Bis Trifluoroacetate (22)

Step A: Preparation of 1-(4-Nitrophenylmethyl)-1H-imidazol-4-ylacetic acid methyl ester (15) and 1-(4-Nitrophenylmethyl)-1H-imidazol-5-ylacetic acid methyl ester (16) (3:1 mixture)

To a solution of sodium hydride (60% in mineral oil, 99 mg, 2.5 mmol) in dimethylformamide (2 ml) cooled to 0° C. was added, via cannula, a solution of 1H-imidazole-4-acetic acid methyl ester hydrochloride (1, 200 mg, 1.13 mmol) in dimethylformamide (3 ml). This suspension was allowed to stir at 0° C. for 15 min. To this suspension was added 4-nitrobenzyl bromide (244 mg, 1.13 mmol) and stirred at room temperature for 2 h. After this time, the mixture was quenched with sat. aq. sodium bicarbonate (15 ml) and water (20 ml) and extracted with methylene chloride (2×50 ml). The combined organic extracts were washed with brine (20 ml), dried ($MgSO_4$), filtered and the solvent was evaporated in vacuo. The residue was purified by flash chromatography using acetonitrile as eluent to give the title compounds as a yellow oil.

$^1$H NMR ($CDCl_3$, 400 MHz) δ 8.20 (2H, d, J=8.5 Hz), 7.49 (1H, s), 7.27 (2H, d, J=8.5 Hz), 7.03 (0.25H, s), 6.87 (0.75H, s), 5.28 (0.5H, s), 5.18 (1.5H, s), 3.70 (2.25H, s), 3.65 (1.5H, s), 3.61 (0.75H, s) and 3.44 (0.5H, s) ppm.

Step B: Preparation of 1-(4-Nitrophenylmethyl)-1H-imidazol-4-ylacetic acid hydrochloride (17) and 1-(4-Nitrophenylethyl)-1H-imidazol-5-ylacetic acid (18) (3:1 mixture)

To a solution of a mixture of 1-(4-Nitrophenylmethyl)-1H-imidazol-4-ylacetic acid methyl ester (15) and 1-(4-Nitrophenylmethyl)- 1H-imidazol-5-ylacetic acid methyl ester (16, 3:1 mixture, 216 mg, 0.785 mmol) in methanol (3 ml) and tetrahydrofuran (3 ml) under argon was added 1.0M sodium hydroxide (1.18 ml, 1.18 mmol) and stirred for 18 h. After this time, 1.0N hydrochloric acid (2.36 ml, 2.36 mmol) was added and the mixture evaporated in vacuo to give the title compounds.

$^1$H NMR ($CDCl_3$, 400 MHz) δ 9.04 (0.75H, s), 8.83 (0.25H, s), 8.28 (2H, d, J=8.8 Hz), 7.61 (2H, d, J=8.8 Hz), 7.54 (0.75H, s), 7.43 (0.25H, s), 5.61 (0.5H, s), 5.58 (1.5H, s), 3.84 (0.5H, s) and 3.82 (1.5H, s) ppm.

Step C: Preparation of N-[(2S)-(1-(4-Nitrophenylmethyl)-1H-imidazol-4-ylacetyl) amino-3(S)-methylpentyl]-N-1-naphthylmethyl-glycyl-methionine methyl ester bis trifluoroacetate (19) and N-[2(S)-(1-(4-Nitrophenyl-methyl)-1H-imidazol-5-ylacetyl)amino-3(S)-methylpentyl]-N-1-naphthylmethyl-glycyl-methionine methyl ester bis trifluoroacetate (20)

To a solution of 1-(4-nitrophenylmethyl)-1H-imidazol-4-ylacetic acid hydrochloride (17) and 1-(4-nitrophenylmethyl)-1H-imidazol-5-ylacetic acid hydrochloride (18, 3:1 mixture, 153 mg, 0.392 mmol), N-[2(S)-amino-3(S)-methylpentyl]-N-naphthylmethyl-glycyl-methionine methyl ester bis hydrochloride (10, 209 mg, 0.392 mmol) and 3-hydroxy-1,2,3-benzotriazin-4(3H)-one (HOOBT, 64 mg, 0.39 mmol) in methylene chloride (10 ml) was added 1-(3-dimethylaminopropyl)-3-ethylcarbodiimide hydrochloride (EDC, 75.2 mg, 0.392 mmol) and triethylamine (219 µl, 1.57 mmol) and the mixture stirred overnight at room temperature. After this time, sat. aq. sodium bicarbonate (10 ml) was added and the mixture was extracted with methylene chloride. The combined extracts were washed with sat. aq. sodium bicarbonate (10 ml) and the solvent evaporated in vacuo. The regioisomers were separated by preparative HPLC (chromatography method A) to give after lyophilization 19 and 20.

19:
$^1$H NMR ($CD_3OD$, 400 MHz) δ 8.96 (1H, s), 8.17 (1H, m), 8.23 (2H, d, J=8.7 Hz), 7.92 (2H, d, J=8.9 Hz), 7.61 (1H, d, J=6.9 Hz), 7.56 (2H, d, J=8.9 Hz), 7.50 (2H, m), 7.44 (2H, m), 5.52 (2H, s), 4.70 (1H, d, J=9.4 Hz), 4.49 (1H, d, J=11.9 Hz), 4.38 (1H, dd, J=4.7 and 8.9 Hz), 4.13 (1H, m), 3.67 (3H, s), 3.65 (4H, m), 3.30 (1H, m), 3.06 (1H, m), 2.31 (1H, m), 2.23 (1H, m), 1.97 (3H, s), 1.94 (1H, m), 1.71 (1H, m), 1.57 (1H, m), 1.42 (1H, m), 1.17 (1H, m), 0.90 (3H, d, J=6.9 Hz) and 0.87 (3H, t, J=7.4 Hz) ppm. Anal. Calcd for $C_{37}H_{46}N_6O_6S·2.40$ TFA·0.25 $H_2O$: C, 51.18; H, 5.02; N, 8.57. Found: C, 51.17; H, 5.03; N, 8.80. FAB MS calcd for $C_{37}H_{47}N_6O_6S$ 703 ($MH^+$), found 703.

20:
$^1$H NMR ($CD_3OD$, 400 MHz) δ 8.91 (1H, s), 8.26 (1H, d, J=12.8 Hz), 8.21 (2H, d, J=10.7 Hz), 7.91 (2H, m), 7.65-7.36

(7H, m), 5.51 (2H, s), 4.72-3.99 (4H, m), 3.66 (3H, s), 3.66-3.24 (4H, m), 3.20-2.85 (2H, m), 2.29 (1H, m), 2.20 (1H, m), 1.96 (3H, s), 1.91 (1H, br s), 1.70 (1H, d, J=16 Hz), 1.56 (1H, m), 1.38 (1H, m), 1.13 (1H, m) and 0.88 (6H, m) ppm. FAB HRMS exact mass calcd for $C_{37}H_{47}N_6O_6S$ 703.32778 (MH$^+$), found 703.32852.

Step D: Preparation of N-[2(S)-(1-(4-Nitrophenylmethyl)-1H-imidazol-4-ylacetyl)amino-3(S)-methylpentyl]-N-1-naphthylmethyl-glycyl-methionine bis trifluoroacetate (21)

To a solution of N-[2(S)-(1-(4-nitrophenylmethyl)-1H-imidazol-4-ylacetyl)amino-3(S)-methylpentyl]-N-1-naphthylmethyl-glycyl-methionine methyl ester bis trifluoroacetate (19, 21 mg, 0.023 mmol) in methanol (1 ml) at room temperature was added 1.0N lithium hydroxide (135 µl, 0.135 mmol). This solution was stirred for 4 h and treated with trifluoroacetic acid (100 µl). This mixture was purified by preparative HPLC using chromatography method A to give 21.

$^1$H NMR (CD$_3$OD, 400 MHz) δ 8.86 (1H, s), 8.23 (2H, d, J=8.8 Hz), 8.22 (1H, m), 7.90 (2H, dd, J=7.3 Hz), 7.55 (2H, d, J=8.4 Hz), 7.44-7.28 (5H, m), 5.50 (2H, s), 4.53 (1H, m), 4.35 (2H, m), 4.12 (1H, m), 3.79-3.25 (4H, m), 3.26-2.86 (2H, m), 2.27 (1H, m), 2.18 (1H, m), 1.96 (3H, s), 1.9 (1H, m), 1.67 (1H, m), 1.57 (1H, m), 1.42 (1H, m), 1.15 (1H, m), 0.90 (3H, d, J=6.9 Hz) and 0.86 (3H, t, J=7.3 Hz) ppm. FAB HRMS exact mass calcd for $C_{36}H_{45}N_6O_6S$ 689.31213 (MH$^+$), found 689.31262.

Step E: Preparation of N-[2(S)-(1-(4-Nitrophenylmethyl)-1H-imidazol-5-ylacetyl)amino-3(S)-methylpentyl]-N-1-naphthylmethyl-glycyl-methionine bis trifluoroacetate (22)

To a solution of N-[2(S)-N'-(1-(4-nitrophenylmethyl)-1H-imidazol-5-ylacetyl)amino-3(S)-methylpentyl]-N-1-naphthylmethyl-glycyl-methionine methyl ester bis trifluoroacetate (20, 29 mg, 0.031 mmol) in methanol (1 ml) was added 1.0N lithium hydroxide (187 µl, 0.187 mmol). This solution was stirred for 4 h and treated with trifluoroacetic acid (100 µl). This mixture was purified by preparative HPLC using chromatography method A to give 22.

$^1$H NMR (CD$_3$OD, 400 MHz) δ 8.89 (1H, s), 8.25 (1H, m), 8.21 (2H, d, J=9.0 Hz), 7.89 (2H, m), 7.64-7.34 (7H, m), 5.52 (2H, s), 4.59-3.88 (4H, m), 3.77-3.38 (4H, m), 3.18-2.75 (2H, m), 2.27 (1H, m), 2.18 (1H, m), 1.96 (3H, s), 1.9 (1H, m), 1.67 (1H, m), 1.57 (1H, m), 1.42 (1H, m), 1.15 (1H, m), 0.89 (6H, m) ppm. FAB HRMS exact mass calcd for $C_{36}H_{45}N_6O_6S$ 689.31213 (MH$^+$), found 689.31135.

EXAMPLE 3

Regioselective Preparation of N-[2(S)-(1-(4-Nitrophenylmethyl)-1H-imidazol-5-ylacetyl)amino-3(S)-methylpentyl]-N-1-naphthylmethyl-glycyl-methionine Methyl Ester Bis Trifluoroacetate (20)

Step A: Preparation of 1-(Triphenylmethyl)-1H-imidazol-4-ylacetic acid methyl ester (23)

To a suspension of 1H-imidazole-4-acetic acid methyl ester hydrochloride (1, 7.48, 42.4 mmol) in methylene chloride (200 ml) was added triethylamine (17.7 ml, 127 mmol) and triphenylmethyl bromide (16.4 g, 50.8 mmol) and stirred for 72 h. After this time, reaction mixture was washed with sat. aq. sodium bicarbonate (100 ml) and water (100 ml). The organic layer was evaporated in vacuo and purified by flash chromatography (30–100% ethyl acetate/hexanes gradient elution) to provide 23 as a white solid.

$^1$H NMR (CDCl$_3$, 400 MHz) δ 7.35 (1H, s), 7.31 (9H, m), 7.22 (6H, m), 6.76 (1H, s), 3.68 (3H, s) and 3.60 (2H, s) ppm.

Step B: Preparation of 1-(4-Nitrophenylmethyl)-1H-imidazol-5-ylacetic acid methyl ester (16)

To a solution of 1-(triphenylmethyl)-1H-imidazol-4-ylacetic acid methyl ester (23, 274 mg, 0.736 mmol) in acetonitrile (10 ml) was added 4-nitrobenzylbromide (159 mg, 0.736 mmol) and heated to 55° C. for 16 h. After this time, the reaction was cooled to room temperature, treated with ethyl acetate (20 ml) and the resulting precipitate was filtered. The filtrate was concentrated to dryness in vacuo and the residue was redissolved in acetonitrile (4 ml) and heated to 65° C. for 3 h. After this time, the reaction mixture was evaporated to dryness and combined with initial precipitate. This residue was dissolved in methanol (5 ml) and heated to reflux for 30 min. The resulting solution was evaporated in vacuo and the residue was purified by flash chromatography (2–5% methanol/methylene chloride gradient elution) to provide 16.

$^1$H NMR (CDCl$_3$, 400 MHz) δ 8.20 (2H, d, J=8.8 Hz), 7.53 (1H, s), 7.19 (2H, d, J=8.8 Hz), 7.03 (1H, s), 5.28 (2H, s), 3.61 (3H, s) and 3.61 (2H, s) ppm.

Step C: Preparation of 1-(4-Nitrophenylmethyl)-1H-imidazol-5-ylacetic acid hydrochloride (18)

1-(4-Nitrophenylmethyl)-1H-imidazol-5-ylacetic acid methyl ester (0.115 g, 0.42 mmol) was dissolved in 1.0N hydrochloric acid (10 ml) and heated at 55° C. for 3 h. The solution was evaporated in vacuo to give 18 as a white solid.

$^1$H NMR (CD$_3$OD, 400 MHz) δ 9.06 (1H, s), 8.27 (2H, d, J=8.8 Hz), 7.61 (1H, s), 7.55 (2H, d, J=8.8 Hz), 5.63 (2H, s) and 3.81 (2H, s) ppm.

Step D: Preparation of N-[2(S)-(1-(4-Nitrophenylmethyl)-1H-imidazol-5-ylacetyl)amino-3(S)-methylpentyl]-N-1-naphthylmethyl-glycyl-methionine methyl ester bis trifluoroacetate (20)

Following the procedure described in Example 2, Step C, but using the 1-(4-nitrophenylmethyl)-1H-imidazol-5-ylacetic acid hydrochloride, prepared as described in Step C provided the title compound.

EXAMPLE 4

Preparation of N-[2(S)-(1-(2-Naphthylmethyl)-1H-imidazol-5-ylacetyl)amino-3(S)-methylpentyl]-N-1-naphthylmethyl-glycyl-methionine Bis Trifluoroacetate Step A: Preparation of N-[2(S)-(1-(2-Naphthylmethyl)-1H-imidazol-5-ylacetyl)amino-3(S)-methylpentyl]-N-1-naphthylmethyl-glycyl-methionine methyl ester bis trifluoroacetate Following the procedure described in Example 3, Steps B–D, but using 2-(bromomethyl)naphthlene in place of 4-nitrobenzylbromide provided the title compound.

$^1$H NMR (CD$_3$OD, 400 MHz) δ 8.89 (1H, s), 8.29 (1H, d, J=9 Hz), 7.92 (4H, m), 7.83 (1H, d, J=9 Hz), 7.68 (1H, s), 7.58-7.42 (7H, m), 7.33 (1H, d, J=9 Hz), 5.54 (2H, s), 4.90-4.50 (2H, m), 4.38 (1H, m), 4.05 (1H, m), 3.93-3.32 (5H, m), 3.65 (3H, s), 3.12 (1H, m), 2.24 (2H, m), 1.93 (3H, s), 1.87 (1H, br s), 1.72 (1H, br s), 1.52 (1H, br s), 1.38 (1H, br s), 1.13 (1H, br s) and 0.87 (6H, m) ppm. Anal. Calcd for $C_{41}H_{49}N_5O_4S$.3.20 TFA.0.75 H$_2$O: C, 52.41; H, 4.98; N, 6.45. Found: C, 52.40; H, 4.96; N, 6.63. FAB HRMS exact mass calcd for $C_{41}H_{50}N_5O_4S$ 708.358352 (MH$^+$), found 708.357618.

Step B: Preparation of N-[2(S)-(1-(2-Naphthylmethyl)-1H-imidazol-5-ylacetyl)amino-3(S)-methylpentyl]-N-1-naphthylmethyl-glycyl-methionine bis trifluoroacetate Following the procedure described in Example 2, Step E, but using the methyl ester prepared as described in Step A provided the title compound.

$^1$H NMR (CD$_3$OD, 400 MHz) δ 8.88 (1H, s), 8.28 (1H, d, J=9 Hz), 7.96-7.78 (5H, m), 7.67 (1H, s), 7.57-7.41 (7H, m), 7.32 (1H, d, J=9 Hz), 5.55 (2H, s), 4.81 (1H, m), 4.56 (1H, m), 4.37 (1H, m), 4.06 (1H, m), 3.89-3.50 (4H, m), 3.42 (1H, m), 3.10 (1H, m), 2.28 (1H, m), 2.19 (1H, m), 2.03-1.86 (1H, m), 1.93 (3H, s), 1.90 (1H, m), 1.71 (1H, m), 1.52 (1H, m), 1.37 (1H, m) and 0.87 (6H, m) ppm. Anal. Calcd for $C_{40}H_{47}N_5O_4S \cdot 2.95$ TFA $\cdot 0.5$ $H_2O$: C, 53.05; H, 4.94; N, 6.74. Found: C, 53.03; H, 4.95; N, 7.10. FAB HRMS exact mass calcd for $C_{40}H_{48}N_5O_4S$ 694.342702 (MH$^+$), found 694.342837.

EXAMPLE 5

Preparation of N-[2(S)-(1-(1-Naphthylmethyl)-1H-imidazol-5-ylacetyl)amino-3(S)-methylpentyl]-N-1-naphthylmethyl-glycyl-methionine Bis Trifluoroacetate Step A: Preparation of N-[2(S)-(1-(1-Naphthylmethyl)-1H-imidazol-5-ylacetyl)amino-3(S)-methylpentyl]-N-1-naphthylmethyl-glycyl-methionine methyl ester bis trifluoroacetate Following the procedure described in Example 3, Steps A–D, but using 1-(bromomethyl)naphthlene in place of 4-nitrobenzylbromide provided the title compound.

$^1$H NMR (CD$_3$OD, 400 MHz) δ 8.42 (1H, s) 8.31 (1H, d, J=8.9 Hz), 8.04-7.80 (5H, m), 7.69 (1H, m), 7.59-7.39 (7H, m), 7.20 (1H, d, J=8.2 Hz), 5.80 (2H, s), 5.0-4.5 (2H, m), 4.26 (1H, m), 4.13 (1H, m), 4.0-3.6 (4H, m), 3.64 (3H, s), 3.49 (1H, m), 3.18 (1H, m), 2.17 (2H, m), 1.91 (3H, s), 1.86 (1H, m), 1.67 (1H, m), 1.55 (1H, m), 1.41 (1H, m), 1.16 (1H, br s), and 0.88 (6H, m) ppm. Anal. Calcd for $C_{41}H_{49}N_5O_4S \cdot 3.10$ TFA $\cdot 0.55$ $H_2O$: C, 52.92; H, 5.01; N, 6.54. Found: C, 52.90; H, 4.99; N, 6.59. FAB HRMS exact mass calcd for $C_{41}H_{50}N_5O_4S$ 708.358352 (MH$^+$), found 708.357618.

Step B: Preparation of N-[2(S)-(1-(1-Naphthylmethyl)-1H-imidazol-5-ylacetyl)amino-3(S)-methylpentyl]-N-1-naphthylmethyl-glycyl-methionine bis trifluoroacetate Following the procedure described in Example 2, Step E, but using the methyl ester prepared as described in Step A provided the title compound.

$^1$H NMR (CD$_3$OD, 400 MHz) δ 8.41 (1H, s), 8.19 (1H, d, J=7.7 Hz), 7.99 (2H, m), 7.87 (3H, m), 7.64 (1H, m), 7.56 (1H, t, J=7 Hz), 7.46 (6H, m), 7.16 (1H, d, J=8 Hz), 5.79 (2H, s), 5.04-4.71 (1H, m), 4.61-4.38 (1H, m), 4.38-4.21 (1H, m), 4.14 (1H, m), 3.97-3.51 (4H, m), 3.51-3.21 (1H, m), 3.21-2.85 (1H, m), 2.21 (1H, m), 2.13 (1H, m), 1.98 (1H, m), 1.91 (3H, s), 1.66 (1H, m), 1.56 (1H, m), 1.40 (1H, m), 1.15 (1H, m), and 0.87 (6H, m) ppm. Anal. Calcd for $C_{40}H_{47}N_5O_4S \cdot 2.70$ TFA $\cdot 0.5$ $H_2O$: C, 53.95; H, 5.06; N, 6.93. Found: C, 53.97; H, 5.06; N, 7.10. FAB HRMS exact mass calcd for $C_{40}H_{48}N_5O_4S$ 694.342702 (MH$^+$), found 694.342837.

EXAMPLE 6

Preparation of N-[2(S)-(1-Farnesyl-1H-imidazol-5-ylacetyl)amino-3(S)-methylpentyl]-N-1-naphthylmethyl-glycyl-methionine Bis Trifluoroacetate Step A: Preparation of 1-Farnesyl-1H-imidazol-5-ylacetic acid methyl ester To a solution of 1-(triphenylmethyl)-1H-imidazol-4-ylacetic acid methyl ester (200 mg, 0.523 mmol) in acetonitrile (5 ml) was added trans, trans-farnesyl bromide (156 μl, 0.575 mmol) and heated at 55° C. for 16 h. After this time, the reaction was heated at 80° C. for 3 h and then the reaction mixture was evaporated in vacuo. The residue was dissolved in methanol (5 ml) and heated to reflux for 30 min and then evaporated in vacuo. The residue was purified by flash chromatography (2–4% methanol/methylene chloride gradient elution) to provide the title compound.

$^1$H NMR (CDCl$_3$, 400 MHz) δ 7.50 (1H, s), 6.92 (1H, s), 5.24 (1H, t, J=5.9 Hz), 5.09 (2H, m), 4.49 (2H, d, J=6.9 Hz), 3.69 (3H, s), 3.60 (2H, s), 1.91-2.15 (8H, m), 1.72 (3H, s), 1.65 (3H, s), 1.59 (3H, s) and 1.57 (3H, s) ppm.

Step B: Preparation of N-[2(S)-(1-(1-Farnesyl)-1H-imidazol-5-ylacetyl)amino-3(S)-methylpentyl]-N-1-naphthylmethyl-glycyl-methionine methyl ester bis trifluoroacetate Following the procedure described in Example 3, Steps C–D, but using 1-farnesyl-1H-imidazol-5-ylacetic acid methyl ester described in Step A in place of 1-(4-nitrophenylmethyl)-1H-imidazol-5-ylacetic acid methyl ester provided the title compound.

$^1$H NMR (CD$_3$OD, 400 MHz) δ 8.70 (1H, s), 8.26 (1H, m), 7.91 (2H, m), 7.52 (3H, m), 7.48 (1H, m), 7.37 (1H, s), 5.40 (1H, m), 5.08 (2H, m), 4.94-4.72 (3H, m), 4.71 (1H, m), 4.40 (1H, m), 4.13 (1H, m), 3.95-2.80 (6H, m), 3.68 (3H, s), 2.27 (1H, m), 2.21 (1H, m), 2.09 (8H, m), 1.97 (3H, s), 1.92 (2H, m), 1.72 (3H, s), 1.65 (1H, m), 1.65 (3H, s), 1.60 (3H, s), 1.58 (3H, s), 1.42 (1H, m), 1.18 (1H, m) and 0.90 (6H, m) ppm. FAB HRMS exact mass Calcd for $C_{45}H_{66}N_5O_4S$ 772.483553 (MH$^+$), found 772.481709.

Step C: Preparation of N-[2(S)-[1-(1-Farnesyl)-1H-imidazol-5-ylacetyl]amino-3(S)-methylpentyl]-N-1-naphthylmethyl-glycyl-methionine bis trifluoroacetate Following the procedure described in Example 2, Step E, but using the methyl ester prepared as described in Step B provided the title compound.

$^1$H NMR (CD$_3$OD, 400 MHz) δ 8.68 (1H, s), 8.18 (1H, m), 7.90 (2H, m), 7.52 (3H, m), 7.44 (1H, t, J=7.5 Hz), 7.37 (1H, s), 5.29 (1H, br t, J=7 Hz), 5.08 (2H, m), 4.95-4.64 (1H, m), 4.73 (2H, m), 4.37 (2H, m), 4.12 (1H, m), 3.71 (2H, m), 3.47 (2H, m), 3.11 (1H, m), 2.95 (1H, m), 2.27 (1H, m), 2.23-2.01 (9H, m), 2.01-1.89 (1H, m), 1.97 (3H, s), 1.77-1.54 (2H, m), 1.71 (3H, s), 1.65 (3H, s), 1.60 (3H, s), 1.58 (3H, s), 1.42 (1H, m), 1.16 (1H, m), 0.91 (3H, t, J=7 Hz) and 0.87 (3H, d, J=7.5 Hz) ppm. FAB HRMS exact mass calcd for $C_{44}H_{64}N_5O_4S$ 758.467903 (MH$^+$), found 758.467591.

EXAMPLE 7

Preparation of N-[2(S)-(1-Geranyl-1H-imidazol-5-ylacetyl)amino-3(S)-methylpentyl]-N-1-naphthylmethyl-glycyl-methionine Bis Trifluoroacetate Step A: Preparation of N-[2(S)-(1-Geranyl-1H-imidazol-5-ylacetyl)amino-3(S)-methylpentyl]-N-1-naphthylmethyl-glycyl-methionine methyl ester bis trifluoroacetate Following the procedure described in Example 6, Steps A–B, but using trans-geranyl bromide in place of farnesyl bromide provided the title compound.

$^1$H NMR (CD$_3$OD, 400 MHz) δ 8.67 (1H, s), 8.27 (1H, m), 7.92 (2H, m), 7.57 (1H, m), 7.53 (2H, m), 7.46 (1H, dd, J=9 Hz), 7.36 (1H, s), 5.29 (1H, t, J=6 Hz), 5.08 (1H, t, J=6 Hz), 4.71 (1H, m), 4.71-4.12 (1H, m), 4.38 (1H, m), 4.12 (1H, m), 3.80-3.33 (4H, m), 3.68 (3H, s), 3.14 (1H, m), 2.96 (1H, m), 2.29 (1H, m), 2.21 (1H, m), 2.12 (4H, m), 2.11 (1H, m), 1.97 (3H, s), 1.97 (1H, m), 1.70 (3H, s), 1.68 (3H, s), 1.65 (1H, m), 1.60 (3H, s), 1.41 (1H, m), 1.15 (1H, m), 0.91 (3H, d, J=7 Hz) and 0.88 (3H, t, J=7.5 Hz) ppm. Anal. Calcd for $C_{40}H_{57}N_5O_4S \cdot 1.80$ TFA $\cdot 0.25$ $H_2O$: C, 57.31; H, 6.54; N, 7.66. Found: C, 57.28; H, 6.54; N, 7.90. FAB HRMS exact mass calcd for C$_{40}$H$_{58}$N$_5$O$_4$S 704.420953 (MH$^+$), found 704.420223.

Step B: Preparation of N-[2(S)-(1-Geranyl-1H-imidazol-5-ylacetyl)amino-3(S)-methylpentyl]-N-1-naphthylmethyl-glycyl-methionine bis trifluoroacetate Following the procedure described in Example 2, Step E, but using the methyl ester prepared as described in Step A provided the title compound.

$^1$H NMR (CD$_3$OD, 400 MHz) δ 8.67 (1H, s), 8.27 (1H, m), 7.92 (2H, m), 7.59 (1H, m), 7.52 (2H, m), 7.46 (1H, t, J=7.8 Hz), 7.38 (1H, s), 5.28 (1H, t, J=11.2 Hz), 5.04 (1H, m), 4.96-4.54 (1H, m), 4.72 (2H, s), 4.54-4.31 (1H, m), 4.39 (1H, m), 4.13 (1H, m), 3.82-3.31 (4H, m), 3.68 (2H, m), 3.31-2.79 (2H, m), 2.30 (1H, m), 2.12 (5H, m), 1.97 (3H, s), 1.97 (1H, m), 1.73 (1H, m), 1.71 (3H, s), 1.70 (3H, s), 1.60 (3H, s), 1.44 (1H, m), 1.18 (1H, m) and 0.92 (3H, d, J=6.8 Hz), and 0.90 (3H, t, J=7.5 Hz) ppm. FAB HRMS exact mass calcd for C$_{39}$H$_{56}$N$_5$O$_4$S 690.405303 (MH$^+$), found 690.405157.

EXAMPLE 8

Preparation of N-[2(S)-(1-(4-Pyridylmethyl)-1H-imidazol-4-ylacetyl)amino-3(S)-methylpentyl]-N-1-naphthylmethyl-glycyl-methionine Tris Trifluoroacetate (28) and N-[2(S)-(1-(4-Pyridylmethyl)-1H-imidazol-5-ylacetyl)amino-(3S)-methylpentyl]-N-1-naphthylmethyl-glycyl-methionine Tris Trifluoroacetate (29)

Step A: Preparation of 1-(4-Pyridylmethyl)-1H-imidazol-4-ylacetic acid methyl ester (24) and 1-(4-Pyridylmethyl)-1H-imidazol-5-ylacetic acid methyl ester (25) (3:1 mixture)

To a solution of sodium hydride (60% in mineral oil, 99 mg, 2.5 mmol) in dimethylformamide (2 ml) cooled at 0° C. over ice bath was added, via cannula, a solution of 1H-imidazole-4-acetic acid methyl ester hydrochloride (1, 115 mg, 0.707 mmol) in dimethylformamide (2 ml). The suspension was stirred at 0° C. for 15 min. This suspension was added to a solution prepared by adding 4-picolyl chloride hydrochloride (185 mg, 0.707 mmol) to sodium hydride (60% in mineral oil, 45.2 mg, 1.13 mmol) in dimethylformamide (2 ml) at 0° C. After the addition was complete, the mixture was stirred at 0° C. for 15 min and then at room temperature for 1.5 h. After this time, the mixture was quenched with sat. aq. sodium bicarbonate (50 ml) and extracted with methylene chloride (2×50 ml). The combined organic extracts were washed with brine (50 ml), dried (MgSO$_4$), filtered and the solvent evaporated in vacuo. The residue was purified by flash chromatography(3–7% methanol/methylene chloride gradient elution) to give a 3:1 mixture of 24 and 25.

$^1$H NMR (CDCL$_3$, 400 MHz) δ 8.57 (1.5H, d, J=5 Hz), 8.56 (0.5H, d, J=7 Hz), 7.51 (0.25H, s), 7.46 (0.75H, s), 7.01 (0.25H, s), 6.99 (1.5H, d, J=5 Hz), 6.90 (0.5H, d, J=7 Hz), 6.86 (0.75H, s), 5.17 (0.5H, s), 5.08 (1.5H, s), 3.69 (2.25H, s), 3.64 (1.5H, s), 3.58 (0.75H, s) and 3.43 (0.5H, s) ppm.

Step B: Preparation of N-[2(S)-(1-(4-Pyridylmethyl)-1H-imidazol-4-ylacetyl)amino-3(S)-methylpentyl]-N-1-naphthylmethyl-glycyl-methionine methyl ester tris trifluoroacetate (26) and N-[2(S)-(1-(4-Pyridylmethyl)-1H-imidazol-5 -ylacetyl)amino-3(S)-methylpentyl]-N-1-naphthylmethyl-glycyl-methionine methyl ester tris trifluoroacetate (27)

Following the procedure described in Example 2, Steps B–C, but using the mixture of pyridylmethylimidazolylacetic acid from Step A provided the title compounds after preparative HPLC.

26:

$^1$H NMR (CD$_3$OD, 400 MHz) δ 8.99 (1H, s), 8.65 (2H, d, J=4.9 Hz), 8.28 ($^1$H, d, J=9.4 Hz), 7.91 (2H, m), 7.69 (1H, d, J=6.5 Hz), 7.61-7.44 (6H, m), 5.59 (2H, s), 4.90 (1H, m), 4.68 (1H, d, J=13.4 Hz), 4.42 (1H, m), 4.16 (1H, m), 3.90 (1H, d, J=15.6 Hz), 3.82 (1H, d, J=15.6 Hz), 3.75-3.55 (2H, m), 3.69 (3H, s), 3.50 (1H, d, J=13.1 Hz), 3.20 (1H, m), 2.37 (1H, m), 2.29 (1H, m), 1.99 (3H, s), 1.96 (1H, m), 1.77 (1H, m), 1.58 (1H, m), 1.23 (1H, m), 1.19 (1H, m) and 0.91 (6H, m) ppm. Anal. Calcd for C$_{36}$H$_{46}$N$_6$O$_4$S.4.95 TFA.2.2 H$_2$O: C, 43.65; H, 4.42; N, 6.65. Found: C, 43.65; H, 4.16; N, 6.68. FAB HRMS exact mass calcd for C$_{36}$H$_{47}$N$_6$O$_4$S 659.337951 (MH$^+$), found 659.336943

27:

$^1$H NMR (CD$_3$OD, 400 MHz) δ 9.01 (1H, s), 8.63 (2H, m), 8.28 (1H, m), 7.98 (2H, m), 7.70 (1H, d, J=6.0 Hz), 7.52 (4H, m), 7.41 (2H, d, J=6.2 Hz), 5.62 (2H, s), 4.94 (1H, m), 4.72 (1H, m), 4.42 (1H, m), 4.07 (1H, m), 3.89 (2H, m), 3.68 (1H, m), 3.69 (3H, s), 3.55 (2H, m), 3.24 (1H, m), 2.39 (1H, m), 2.31 (1H, m), 2.00 (3H, s), 1.98 (1H, m), 1.79 (1H, m), 1.58 (1H, m), 1.42 (1H, m), 1.18 (1H, m) and 0.91 (6H, m) ppm. FAB HRMS exact mass calcd for C$_{36}$H$_{47}$N$_6$O$_4$S 659.337951 (MH$^+$), found 659.336826.

Step C: Preparation of N-[2(S)-(1-(4-Pyridylmethyl)-1H-imidazol-4-ylacetyl)amino-3(S)-methylpentyl]-N-1-naphthylmethyl-glycyl-methionine methyl ester tris trifluoroacetate (28)

Following the procedure described in Example 2, Step D, but using the methyl ester 26 prepared as described in Step B provided the title compound.

$^1$H NMR (CD$_3$OD, 400 MHz) δ 8.96 (1H, s), 8.55 (2H, d, J=5.2 Hz), 8.21 (1H, d, J=7.2 Hz), 7.97 (2H, m), 7.69 (1H, d, J=7.2 Hz), 7.60-7.40 (6H, m), 5.58 (2H, s), 4.91 (1H, d, J=13.2 Hz), 4.69 (1H, d, J=13.2 Hz), 4.38 (1H, dd, J=4.6 and 8.8 Hz), 4.15 (1H, m), 3.89 (1H, d, J=16.1 Hz), 3.81 (1H, d, J=16.1 Hz), 3.71 (1H, d, J=17 Hz), 3.62 (1H, d, J=17 Hz), 3.50 (1H, dd, J=3.4 and 12 Hz), 3.21 (1H, m), 2.38 (1H, m), 2.27 (1H, m), 1.99 (1H, m), 1.99 (3H, s), 1.77 (1H, m), 1.58 (1H, m), 1.43 (1H, m), 1.16 (1H, m), and 0.88 (6H, m) ppm. FAB HRMS exact mass calcd for C$_{35}$H$_{45}$N$_6$O$_4$S 645.322301 (MH$^+$), found 645.323649.

Step D: Preparation of N-[2(S)-(1-(4-Pyridylmethyl)-1H-imidazol-5-ylacetyl)amino-3(S)-methylpentyl]-N-1-naphthylmethyl-glycyl-methionine tris trifluoroacetate (29)

Following the procedure described in Example 2, Step E, but using the methyl ester 27 prepared as described in Step B provided the title compound.

$^1$H NMR (CD$_3$OD, 400 MHz) δ 8.97 (1H, s), 8.58 (2H, s), 8.27 (1H, m), 7.95 (2H, m), 7.64 (1H, m), 7.50 (4H, m), 7.31 (2H, d, J=4.4 Hz), 5.57 (2H, m), 4.63 (2H, m), 4.38 (1H, m), 4.09 (1H, m), 3.78 (2H, m), 3.60 (2H, m), 3.42 (1H, m), 3.15 (1H, m), 2.36 (1H, m), 2.15 (1H, m), 2.01 (1H, m), 1.98 (3H, s), 1.76 (1H, m), 1.55 (1H, m), 1.41 (1H, m), 1.15 (1H, m) and 0.88 (6H, m) ppm. FAB HRMS exact mass calcd for C$_{35}$H$_{45}$N$_6$O$_4$ 645.322301 (MH$^+$), found 645.321321.

EXAMPLE 9

Preparation of N-[2(S)-(1-(4-Cyanophenylmethyl)-1H-imidazol-5-ylacetyl)amino-3(S)-methylpentyl]-N-1-naphthylmethyl-glycyl-methionine Bis Trifluoroacetate Step A: Preparation of N-[2(S)-(1-(4-Cyanophenylmethyl)-1H-imidazol-5-ylacetyl)amino-3(S)-methylpentyl]-N-1-naphthylmethyl-glycyl-methionine methyl ester bis trifluoroacetate Following the procedure described in Example 3, Steps B–D, but using a-bromo-p-tolunitrile in place of 4-nitrobenzylbromide provided the title compound.

$^1$H NMR (CD$_3$OD, 400 MHz) δ 8.92 (1H, s), 8.31 (1H, m), 8.01 (1H, d, J=8 Hz), 7.96 (1H, m), 7.75 (2H, d, J=8 Hz), 7.62 (1H, s), 7.58-7.48 (3H, m), 7.45 (1H, m), 7.41 (2H, d, J=8 Hz), 5.51 (2H, s), 4.97 (1H, m), 4.76 (1H, m), 4.41 (1H, m), 4.10 (1H, m) 3.92 (2H, m), 3.75-3.47 (3H, m), 3.69 (3H, s), 3.25 (1H, m), 2.37 (1H, m), 2.30 (1H, m), 2.00 (3H, s), 1.97 (1H, m), 1.79 (1H, m), 1.58 (1H, m), 1.43 (1H, m), 1.19 (1H, m) and 0.91 (6H, m) ppm. Anal. Calcd for C$_{38}$H$_{46}$N$_6$O$_4$S.2.40 TFA.1.90 H$_2$O: C, 51.89; H, 5.31; N, 8.48. Found: C, 51.88; H, 5.29; N, 8.72. FAB HRMS exact mass calcd for C$_{38}$H$_{47}$N$_6$O$_4$S 683.337951 (MH$^+$), found 683.338437.

Step B: Preparation of N-[2(S)-(1-(4-Cyanophenylmethyl)-1H-imidazol-5-ylacetyl)amino-3(S)-methylpentyl]-N-1-naphthylmethyl-glycyl-methionine bis trifluoroacetate To a solution of N-[2(S)-(1-(4-cyanophenylmethyl)-1H-imidazol-5-ylacetyl)amino-3(S)-methylpentyl]-N-1-naphthylmethyl-glycyl-methionine methyl ester bis trifluoroacetate (25.6 mg, 0.028 mmol) in methanol (1 ml) was added 1.0N sodium hydroxide (280 μl, 0.280 mmol) and stirred for 2 h. After this time, the mixture was treated with trifluoroacetic acid (to pH<3) and purified by preparative HPLC (chromatography method A) to give after lyophilization, the title compound.

$^1$H NMR (CD$_3$OD, 400 MHz) δ 8.87 (1H, s), 8.27 (1H, d, J=9.2 Hz), 7.90 (2H, m), 7.73 (2H, d, J=8 Hz), 7.60 (1H, s), 7.46 (4H, m), 7.36 (2H, d, J=8 Hz), 5.48 (2H, s), 4.95-4.28 (2H, m), 4.36 (1H, m), 4.09 (1H, m), 3.59 (4H, m), 3.51-2.73 (2H, m), 2.29 (1H, m), 2.19 (1H, m), 2.03-1.85 (1H, m), 1.97 (3H, s), 1.70 (1H, m), 1.56 (1H, m), 1.39 (1H, m), 1.14 (1H, m) and 0.89 (6H, m) ppm. Anal. Calcd for C$_{37}$H$_{44}$N$_6$O$_4$S.2.45 TFA.1.3 H$_2$O: C, 51.80; H, 5.09; N, 8.65. Found: C, 51.78; H, 5.07; N, 8.95. FAB HRMS exact mass Calcd for C$_{37}$H$_{44}$N$_6$O$_4$S 669.322301 (MH$^+$), found 669.323148.

EXAMPLE 10

Preparation of N-[2(S)-(1-(4-Methoxyphenylmethyl)-1H-imidazol-5-ylacetyl)amino-3(S)-methylpentyl]-N-1-naphthylmethyl-glycyl-methionine Bis Trifluoroacetate Step A: Preparation of N-[2(S)-(1-(4-Methoxyphenylmethyl)-1H-imidazol-5-yl)acetyl)amino-3(S)-methylpentyl]-N-1-naphthylmethyl-glycyl-methionine methyl ester bis trifluoroacetate Following the procedure described in Example 3, Steps B–D, but using 4-methoxybenzyl chloride in place of 4-nitrobenzylbromide provided the title compound.

$^1$H NMR (CD$_3$OD, 400 MHz) δ 8.70 (1H, s), 8.27 (1H, m), 7.92 (2H, m), 7.70-7.35 (5H, m), 7.18 (2H, d, J=8.5 Hz), 6.92 (2H, d, J=8.5 Hz), 5.27 (2H, s), 4.60-4.00 (4H, m), 3.79 (3H, s), 3.67 (3H, s), 3.61 (4H, m), 3.40-2.75 (2H, m), 2.28 (1H, m), 2.19 (1H, m), 1.96 (3H, s), 1.91 (1H, m), 1.70 (1H, m), 1.60 (1H, m), 1.43 (1H, m), 1.18 (1H, m) and 0.91 (6H, m) ppm. Anal. Calcd for C$_{38}$H$_{49}$N$_5$O$_5$S.1.75 TFA.1.75 H$_2$O: C, 54.45; H, 5.98; N, 7.67. Found: C, 54.44; H, 5.95; N, 7.85. FAB HRMS exact mass calcd for C$_{38}$H$_{50}$N$_5$O$_5$S 688.353267 (MH$^+$), found 688.352186.

Step B: Preparation of N-[2(S)-(1-(4-Methoxyphenylmethyl)-1H-imidazol-5-ylacetyl)amino-3(S)-methylpentyl]-N-1-naphthylmethyl-glycyl-methionine bis trifluoroacetate Following the procedure described in Example 9, Step B, but substituting the methyl ester from Step A provided the title compound.

$^1$H NMR (CD$_3$OD, 400 MHz) δ 8.70 (1H, s), 8.27 (1H, m), 7.92 (2H, m), 7.63 (1H, s), 7.56-7.35 (4H, m), 7.18(2H, d, J=8.6 Hz), 6.93 (2H, d, J=8.6 Hz), 5.27 (2H, s), 4.93-4.29 (2H, m), 4.36 (1H, m), 4.12 (1H, m), 3.79 (3H, s), 3.63 (4H, m), 3.07 (2H, m), 2.28 (1H, m), 2.19 (1H, m), 2.02-1.88 (1H, m), 1.95 (3H, s), 1.70 (1H, m), 1.60 (1H, m), 1.43 (1H, m), 1.18 (1H, m) and 0.91 (6H, m) ppm. FAB HRMS exact mass calcd for C$_{37}$H$_{48}$N$_5$O$_5$S 674.337617 (MH$^+$), found 674.338053.

EXAMPLE 11

Preparation of N-[2(S)-(1-(4-Quinolinylmethyl)-1H-imidazol-5-ylacetyl)amino-3(S)-methylpentyl]-N-1-naphthylmethyl-glycyl-methionine Bis Trifluoroacetate Step A: Preparation of N-[2(S)-(1-(4-Quinolinylmethyl)-1H-imidazol-5-ylacetyl)amino-3(S)-methylpentyl]-N-1-naphthylmethyl-glycyl-methionine methyl ester bis trifluoroacetate Following the procedure described in Example 3, Steps B–D, but using 4-(bromomethyl)quinoline hydrochloride in place of 4-nitrobenzylbromide provided the title compound.

$^1$H NMR (CD$_3$OD, 400 MHz) δ 8.88 (1H, s), 8.83 (1H, d, J=4.8 Hz), 8.28 (1H, m), 8.15 (1H, d, J=8.6 Hz), 7.99-7.85 (4H, m), 7.67 (2H, m), 7.57 (1H, s), 7.48 (3H, m), 6.96 (1H, m), 6.02 (2H, s), 4.90 (1H, m), 4.62 (1H, m), 4.18 (1H, m), 4.07 (1H, m), 3.94-3.50 (4H, m), 3.64 (3H, s), 3.45 (1H, m), 3.13 (1H, m), 2.28 (1H, m), 2.21 (1H, m), 1.95 (3H, s), 1.87 (1H, m), 1.69 (1H, m), 1.48 (1H, m), 1.35 (1H, m), 1.11 (1H, m) and 0.84 (6H, m) ppm. FAB HRMS exact mass calcd for C$_{40}$H$_{49}$N$_6$O$_4$S 709.353601 (MH$^+$), found 709.353711.

Step B: Preparation of N-[2(S)-(1-(4-Quinolinylmethyl)-1H-imidazol-5-ylacetyl)amino-3(S)-methylpentyl]-N-1-naphthylmethyl-glycyl-methionine bis trifluoroacetate Following the procedure described in Example 9, Step B, but substituting the methyl ester from Step A provided the title compound.

$^1$H NMR (CD$_3$OD, 400 MHz) δ 8.87 (1H, s), 8.82 (1H, d, J=5 Hz), 8.28 (1H, m), 8.15 (1H, d, J=8.6 Hz), 8.06-7.82 (4H, m), 7.67 (2H, m), 7.58 (1H, s), 7.48 (3H, s), 6.96 (1H, m), 6.03 (2H, s), 4.93-4.57 (2H, m), 4.22 (1H, m), 4.08 (1H, m), 3.72 (4H, m), 3.47 (1H, m), 3.13 (1H, m), 2.28 (1H, m), 2.21 (1H, m), 1.95 (3H, s), 1.87 (1H, m), 1.70 (1H, m), 1.48 (1H, m), 1.35 (1H, m), 1.09 (1H, m) and 0.84 (6H, m) ppm. FAB HRMS exact mass calcd for C$_{39}$H$_{47}$N$_6$O$_4$S 695.33795 (MH$^+$), found 695.33893.

EXAMPLE 12

Preparation of N-[2(S)-(1-(2-Naphthylmethyl)-1H-imidazol-5-ylacetyl)amino-3(S)-methylpentyl]-N-1-phenylmethyl-glycyl-methionine Bis Trifluoroacetate Step A: Preparation of N-[2(S)-(1-(2-Naphthylmethyl)-1H-imidazol-5-ylacetyl)amino-3(S)-methylpentyl]-N-1-phenylmethyl-glycyl-methionine methyl ester bis trifluoroacetate To a solution of 1-(2-naphthylmethyl)-1H-imidazol-5-ylacetic acid hydrochloride (prepared in Example 4, 75 mg, 0.25 mmol), N-[2(S)-amino-3(S)-methylpentyl]-N-phenylmethyl-glycyl-methionine methyl ester bis hydrochloride (prepared analogously to 10, 112 mg, 0.248 mmol) and 3-hydroxy-1,2,3-benzotriazin-4(3H)-one (HOOBT, 44 mg, 0.27 mmol) in dimethylformamide (5 ml) was added 1-(3-dimethylaminopropyl)-3-ethylcarbodiimide hydrochloride (EDC, 52 mg, 0.272 mmol) and triethylamine (171 μl, 1.23 mmol) and the suspension stirred for 3 days. After this time, sat. aq. sodium bicarbonate (10 ml) and water (10 ml) was added and the mixture was extracted with ethyl acetate (2×50 ml). The combined extracts were washed with brine (20 ml) and the solvent evaporated in vacuo. Purification by preparative HPLC (chromatography method A) gave, after lyophilization, the title compound.

$^1$H NMR (CD$_3$OD, 400 MHz) δ 8.94 (1H, s), 7.93 (1H, d, J=8.5 Hz), 7.88 (2H, m), 7.81 (1H, s), 7.55 (5H, m), 7.43 (4H, m), 5.68 (2H, s), 4.60 (1H, m), 4.46 (1H, dd, J=4.5 Hz), 4.27 (1H, d, J=13 Hz), 4.14 (1H, m), 3.95 (1H, d, J=15.5 Hz), 3.85 (1H, d, J=15.5 Hz), 3.83 (2H, s), 3.67 (3H, s), 3.48 (1H, d, J=13 Hz), 3.24 (1H, d, J=13 Hz), 2.40 (1H, m), 2.31 (1H, m), 2.00 (1H, m), 1.96 (3H, s), 1.85 (1H, m), 1.57 (1H, m), 1.44 (1H, m), 1.19 (1H, m), 0.93 (3H, d, J=6.7 Hz) amd 0.91 (3H, t, J=7 Hz) ppm. Anal. Calcd for C$_{37}$H$_{47}$N$_5$O$_4$S.2.85 TFA.0.40 H$_2$O: C, 51.80; H, 5.16; N, 7.07. Found: C, 51.80; H, 5.14; N, 7.31.

Step B: Preparation of N-[2(S)-(1-(2-Naphthylmethyl)-1H-imidazol-5-ylacetyl)amino-3(S)-methylpentyl]-N-1-phenylmethyl-glycyl-methionine bis trifluoroacetate Following the procedure described in Example 9, Steps B, but substituting the methyl ester from Step A provided the title compound.

$^1$H NMR (CD$_3$OD, 400 MHz) δ 8.92 (1H, s), 7.93 (1H, d, J=8.6 Hz), 7.87 (2H, m), 7.78 (1H, s), 7.55 (3H, m), 7.43 (2H, m), 7.39 (1H, d, J=8.4 Hz), 7.35 (3H, m), 5.67 (2H, s), 4.46 (1H, dd, J=4.5 Hz), 4.41-3.90 (1H, m), 4.11 (1H, m), 4.00 (1H, m), 3.75 (2H, m), 3.64 (2H, m), 3.20 (1H, m), 2.98 (1H, m), 2.43 (1H, m), 2.35 (1H, m), 2.08 (1H, m), 1.97 (3H, s), 1.91 (1H, m), 1.54 (1H, m), 1.40 (1H, m), 1.15 (1H, m) and 0.89 (6H, m) ppm. Anal. Calcd for C$_{36}$H$_{45}$N$_5$O$_4$S.2.70 TFA.0.70 H$_2$O: C, 51.57; H, 5.13; N, 7.26. Found: C, 51.54; H, 5.11; N, 7.43. FAB HRMS exact mass calcd for C$_{36}$H$_{46}$N$_5$O$_4$S 644.327052 (MH$^+$), found 644.326203.

EXAMPLE 13

Preparation of N-[2(S)-(1-(2-Naphthylmethyl)-1H-imidazol-5-ylethyl)amino-3(S)-methylpentyl]-N-1-naphthylmethyl-glycyl-methionine Bis Trifluoroacetate Step A: Preparation of N-Methoxy-N-methyl-1-(2-naphthylmethyl)-1H-imidazol-5-ylacetamide To a solution of 1-(2-naphthylmethyl)-1H-imidazol-5-ylacetic acid hydrochloride (prepared in Example 4, 0.819 mg, 2.70 mmol) in dimethylformamide (15 ml) was added sequentially N, O-dimethylhydroxylamine hydrochloride (293 mg, 3.0 mmol), 3-hydroxy-1,2,3-benzotriazin-4(3H)-one (HOOBT, 489 mg, 3.0 mmol), 1-(3-dimethylaminopropyl)-3-ethylcarbodiimide hydrochloride (EDC, 575 mg, 3.0 mmol) and triethylamine (1.67 ml, 12.0 mmol) and the resulting mixture stirred at room temperature for 18 h. Saturated aq. sodium bicarbonate (30 ml) and water (30 ml) were added and the mixture was extracted with methylene chloride (2×50 ml). The combined organic extracts were washed with brine (50 ml) and the solvent evaporated in vacuo. The residue was purified by flash chromatography (2–4% methanol/methylene chloride gradient elution) to provide the title compound as an oil.

$^1$H NMR (CDCl$_3$, 400 MHz) δ 7.80 (2H, m), 7.74 (1H, m), 7.56 (1H, s), 7.47 (3H, m), 7.22 (1H, d, J=8.6 Hz), 6.97 (1H, s), 5.37 (2H, s), 3.58 (2H, s), 3.51 (3H, s) and 3.12 (3H, s) ppm.

Step B: 1-(2-Naphthylmethyl)-1H-imidazol-5-ylacetaldehyde (30)

To a suspension of lithium aluminum hydride (40.8 mg, 1.07 mmol) in tetrahydrofuran (5 ml) at −45° C. was added a solution of N-methoxy-N-methyl-1-(2-naphthylmethyl)-1H-imidazol-5-ylacetamide (243 mg, 0.895 mmol) in tetrahydrofuran (5 ml) via cannula at such a rate to maintain the temperature at <−35° C. After the addition was complete, the reaction was allowed to warm to +5° C. and then recooled to −35° C. To this solution was added a solution of potassium bisulfate (272 mg) in water (1 ml). The mixture was stirred for 30 min at room temperature and then filtered through celite. The celite pad was washed with ethyl acetate (25 ml). The combined filtrates were washed with sat. sodium bicarbonate (10 ml) and then water (10 ml). The organic layer was dried (MgSO$_4$), filtered and evaporated in vacuo to give 30 as a clear oil. This material was used as is in the next step.

$^1$H NMR (CDCl$_3$, 400 MHz) δ 9.50 (1H, t, J=2 Hz), 7.85-7.70 (3H, m), 7.64 (1H, s), 7.53-7.40 (3H, m), 7.16 (1H, d, J=12 Hz), 7.06 (1H, s), 5.20 (2H, s) and 3.53 (2H, m) ppm.

Step C: Preparation of N-[2(S)-(1-(2-Naphthylmethyl)-1H-imidazol-5-ylethyl)amino-3(S)-methylpentyl]-N-1-naphthylmethyl-glycyl-methionine methyl ester bis trifluoroacetate To a solution of 1-(2-naphthylmethyl)-1H-imidazol-5-ylacetaldehyde (116.8 mg, 0.465 mmol) and N-[2(S)-amino-3(S)-methylpentyl]-N-naphthylmethyl-glycyl-methionine methyl ester bis hydrochloride (10, 297 mg, 0.558 mmol) in 1,2-dichloroethane (10 ml) and dimethylformamide (5 ml) was added 3A molecular sieves (500 mg) and sodium triacetoxyborohydride (473 mg, 2.23 mmol). This mixture was stirred at room temperature for 18 h. After this time, the mixture was filtered through a sintered glass funnel. The filtrate was diluted with methylene chloride (100 ml) and washed with sat. sodium bicarbonate (50 ml). The organic layer was dried over magnesium sulfate, filtered and the solvent was evaporated in vacuo. The residue was purified first by flash chromatography eluting with 2–5% methanol/methylene chloride and then by preparative HPLC (chromatography method A) to provide the title compound as a white foam.

$^1$H NMR (CD$_3$OD, 400 MHz) δ 9.05 (1H, s), 8.10 (1H, d, J=7.5 Hz), 8.02-7.79 (5H, m), 7.75 (1H, s), 7.65-7.27 (7H, m), 7.21 (1H, s), 5.59 (2H, s), 4.65 (1H, dd, J=4.7 and 9.4 Hz), 4.31 (1H, d, J=13 Hz), 4.17 (1H, d, J=13 Hz), 3.69 (3H, s), 3.65 (1H, d, J=17 Hz), 3.55 (1H, d, J=17 Hz), 3.00 (1H, dd, J=3.5 and 14 Hz), 2.93-2.42 (6H, m), 2.33 (1H, m), 2.23 (1H, m), 2.13 (1H, m), 2.06 (3H, s), 1.96 (1H, m), 1.41 (1H, m), 1.07 (2H, m), 0.75 (3H, d, J=6.5 Hz) and 0.70 (3H, t, J=7.5 Hz) ppm. FAB HRMS exact mass calcd for C$_{41}$H$_{52}$N$_5$O$_3$S 694.37909 (MH$^+$), found 694.37959.

Step D: Preparation of N-[2(S)-(1-(2-Naphthylmethyl)-1H-imidazol-5-ylethyl)amino-3(S)-methylpentyl]-N-1-naphthylmethyl-glycyl-methionine bis trifluoroacetate Following the procedure described in Example 2, Steps D, but substituting the methyl ester from Step C provided the title compound.

$^1$H NMR (CD$_3$OD, 400 MHz) δ 8.95 (1H, s), 8.09 (1H, d, J=7.7 Hz), 7.94 (1H, d, J=8.5 Hz), 7.93-7.78 (4H, m), 7.73 (1H, s), 7.62-7.24 (7H, m), 7.17 (1H, s), 5.56 (2H, s), 4.61 (1H, dd, J=4.3 and 10 Hz), 4.31 (1H, d, J=13 Hz), 4.14 (1H, d, J=13 Hz), 3.65 (1H, d, J=17 Hz), 3.55 (1H, d, J=17 Hz), 2.99 (1H, d, J=15 Hz), 2.91-2.43 (6H, m), 2.25-1.91 (4H, m), 2.06 (3H, s), 1.33 (1H, m), 1.01 (2H, m), 0.72 (3H, d, J=6.7 Hz) and 0.65 (3H, t, J=7.5 Hz) ppm. FAB HRMS exact mass calcd for C$_{40}$H$_{50}$N$_5$O$_3$S 680.36344 (MH$^+$), found 680.36282

EXAMPLE 14

Preparation of 2(S)-[N-2(S)-(1-(2-Naphthylmethyl)-1H-imidazol-5-ylacetyl)amino-3(S)-methyl]pentyloxy-3-phenylpropionyl-methionine Sulfone Methyl Ester Hydrochloride Step A: Preparation of N-(α-chloroacetyl)-L-isoleucinol To a stirred solution of L-isoleucinol (20 g, 0.17 mol) and triethylamine (28.56 ml, 0.204 mol) in $CH_2Cl_2$ (500 ml) at −78° C. was added chloroacetyl chloride (16.3 ml, 0.204 mol) over 5 minutes. The cooling bath was removed and the solution allowed to warm to −20° C. The mixture was diluted with EtOAc and washed sequentially with 1M HCl, and brine and dried ($Na_2SO_4$). Evaporation in vacuo afforded the title compound Rf=0.3 $CH_2Cl_2$:MeOH (95:5);

$^1$H NMR ($CDCl_3$) δ 6.80 (1H, brd, J=5 Hz), 4.10 (2H, s), 3.84 (1H, m), 3.79 (2H, m), 2.65 (1H, brs), 1.72 (1H, m), 1.55 (1H, m), 1.17 (1H, m), 0.96 (3H, d, J=6 Hz) 0.90 (3H, t, J=6 Hz).

Step B: Preparation of 5(S)-[1(S)-methyl]propyl-2,3,5,6-tetra-hydro-4H-1,4-oxazin-3-one To a stirred solution of N-(α-chloroacetyl)-L-isoleucinol (68, 7.4 g, 0.038 mol) in THF (125 ml) under argon at 0° C. was slowly added sodium hydride (2.2 g of a 60% dispersion in mineral oil, 0.055 mol) with concomitant gas evolution. After completing the addition, the mixture was warmed to room temperature (R.T.) and stirred for 16 hr. Water (2.8 ml) was added and the solvents evaporated in vacuo. The residue was dissolved in $CHCl_3$ (70 ml) and washed with saturated NaCl solution. The organic layer was dried ($Na_2SO_4$) and evaporated in vacuo. The residue was chromatographed using silica gel eluting with $CH_2Cl_2$:MeOH (96:4) to afford the title compound as a white solid. Rf=0.35 $CH_2Cl_2$:MeOH (95:5);

$^1$H NMR ($CDCl_3$) δ 6.72 (1H, brs), 4.20 (1H, d, J=14.5 Hz), 4.10 (1H, d, J=14.5 Hz), 3.88 (1H, dd, J=9 and 3.5 Hz), 3.58 (1H, dd, J=9 and 6.5 Hz), 3.45 (1H, brqt, J=3.5 Hz), 1.70-1.45 (2H, m), 1.34-1.15 (1H, m), 0.96 (3H, t, J=6.5 Hz), 0.94 (3H, d, J=6.5 Hz).

Step C: Preparation of N-(tert-butoxycarbonyl)-5(S)-[1(S)-methyl]propyl-2,3,5,6-tetrahydro-4H-1,4-oxazin-3-one 5(S)-[1(S)-Methyl]propyl-2,3,5,6-tetrahydro 4H-1,4-oxazin-3-one (12.2 g, 0.0776 mol) and DMAP (18.9 g, 0.155 mol) were dissolved in methylene chloride (120 ml) under argon at room temperature. Boc anhydride (33.9 g, 0.155 mol) was added to the stirred solution in one portion, with concomitant gas evolution and the mixture was stirred at for 16 hr. The solvent was evaporated in vacuo and the residue was taken up in ethyl acetate and washed sequentially with 10% citric acid, 50% $NaHCO_3$ and finally brine. The organic extract was dried ($Na_2SO_4$) and evaporated in vacuo. Chromatography of the residue over silica gel eluting with 20% EtOAc in hexanes afforded the title compound as a white solid. Rf=0.75 EtOAc:hexanes (20:80); mp 59°–60° C.

Anal. Calcd for $C_{13}H_{23}O_4N$: C, 60.68; H, 9.01; N, 5.44. Found: C, 60.75; H, 9.01; N, 5.58.

$^1$H NMR ($CDCl_3$) δ 4.25 (1H, d, J=15 Hz), 4.15 (1H, d, J=15 Hz), 4.15-4.00 (2H, m), 3.73 (1H, dd, J=10 and 2 Hz), 1.88 (1H, qt, J=6 Hz), 1.55 (9H, s), 1.50-1.36 (1H, m), 1.35-1.19 (1H, m), 1.00 (3H, d, J=6 Hz), 0.95 (3H, d, J=6.5 Hz).

Step D: Preparation of N-(tert-Butoxycarbonyl)-2(S)-benzyl-5(S)-[1(S)-methyl]propyl-2,3,5,6-tetrahydro-4H-1,4-oxazin-3-one A solution of N-(tert-butoxycarbonyl)-5(S)-[1(S)-methyl]propyl-2,3,5,6-tetrahydro-4H-1,4-oxazin-3-one (5.75 g, 22.3 mmol) in DME (100 ml) under argon was cooled to −60° C. The cold solution was transferred via canula to a second flask containing sodium bis(trimethylsilyl)amide (24.58 ml of a 1M solution in THF, 24.58 mmol) at −78° C. under argon. After stirring for 10 minutes, benzyl bromide (2.25 ml, 19.0 mmol) was added over 5 minutes and the resulting mixture was stirred at −78° C. for 3 hours. After this time, the reaction mixture was transferred via cannula to another flask containing sodium bis(trimethylsilyl)amide (24.58 ml of a 1M solution in THF, 24.58 mmol) at −78° C., under argon. After stirring for a further 5 minutes, the reaction was quenched by the addition of saturated aqueous ammonium chloride solution (24.6 ml) and allowed to warm to room temperature. This mixture was diluted with brine (50 ml) and water (20 ml) and then extracted with ethyl acetate (2×100 ml). The organic extracts were washed with brine (50 ml) and evaporated in vacuo to afford an oil. Chromatography of the residue over silica gel (230–400 mesh, 300 g) eluting with 10–20% ethyl acetate in hexanes afforded the title compound as a clear oil. Rf=0.25 EtOAc:Hexanes (20:80);

$^1$H NMR ($CDCl_3$) δ 7.35-7.15 (5H, m), 4.31 (1H, dd, J=6 and 2 Hz), 4.03 (1H, d, J=12 Hz), 3.88 (1H, dd, J=6 and 1 Hz), 3.66 (1H, dd, J=12 and 2 Hz), 3.29 (1H, dd, J=12 and 3 Hz), 1.54 (9H, s), 3.12 (1H, dd, J=12 and 7 Hz), 1.47 (1H, m), 1.25 (1H, m), 1.10 (1H, m), 0.83 (3H, d, J=6 Hz), 0.80 (3H, t, J=6 Hz).

Step E: Preparation of N-(tert-butoxycarbonyl)-2(S)-[2(S)-amino-3(S)-methyl]pentyloxy-3-phenyl-propionic acid To a stirred solution of N-(tert-butoxycarbonyl)-2(S)-benzyl-5(S)-[1(S)-methyl]-propyl-2,3,5,6-tetrahydro-4H-1,4-oxazin-3-one (5.1 g, 14.7 mmol) in THF (150 ml) and water (50 ml) at 0° C. was added hydrogen peroxide (15 ml of a 30% aqueous solution, 132 mmol) and lithium hydroxide (3.0 g, 63.9 mmol). After stirring for 30 minutes, the reaction was quenched with a solution of sodium sulfite (28.25 g, 0.224 mol) in water (70 ml). The THF was evaporated in vacuo and the aqueous phase was acidified to pH 3–4 by addition of 10% citric acid solution and extracted with EtOAc. The organic extracts were dried ($Na_2SO_4$), evaporated in vacuo and the residue purified by chromatography over silica gel eluting with 4% MeOH in $CH_2Cl_2$ to give 2(S)-benzyl-5(S)-[1(S)-methyl]propyl-2,3,5,6-tetrahydro-4H-1,4-oxazin-3-one and then with 20% MeOH in $CH_2Cl_2$ to afford the title compound as a white solid (pet ether, mp 68°–70° C.). Rf=0.4 MeOH:$CH_2Cl_2$ (5:95)+0.3% AcOH;

$^1$H NMR ($d_6$ DMSO) δ 7.35-7.10 (5H, m), 6.68 (1H, br, s), 3.75 (1H, dd, J=7.5 and 2.5 Hz) 3.54 (1H, m), 3.5-3.2 (2H, m) 2.99 (1H, dd, J=12.5 and 2.5 Hz), 2.75 (1H, dd, J=12.5 and 7.5 Hz), 1.50-1.35 (11H, m), 0.98 (1H, sept, J=6 Hz), 0.78 (3H, t, J=6 Hz), 0.65 (3H, d, J=6 Hz); FAB MS 366 ($MH^+$) 266 ($MH_2^+$−$CO_2^tBu$).

Step F: Preparation of N-(tert-Butoxycarbonyl)-2(S)-[2(S)-amino-3(S)-methyl]-pentyloxy-3-phenyl-propionyl-methione sulfone methyl ester The title compound was prepared by EDC coupling of N-(tert-butoxycarbonyl)-2(S)-[2(S)-amino-3(S)-methyl]pentyloxy-3-phenylpropionic acid with methionine sulfone methyl ester.

$^1$H NMR ($CD_3OD$) δ 0.80 (3H, d, J=6 Hz), 0.88 (3H, t, J=6 Hz), 1.12 (1H, m), 1.40–1.55 (1H, m), 1.47 (9H, s), 2.10 (1H, m), 2.32 (1H, m), 2.80–3.10 (4H, m), 2.93 (3H, s), 3.40 (1H, m), 3.5–3.7 (2H, m), 3.74 (3H, s), 4.01 (H, m), 4.60 (H, m), 6.60 (H, d, J=8 Hz), 7.25 (5H, m).

Step G: Preparation of 2(S)-[2(S)-Amino-3(S)-methyl]pentyloxy-3-phenylpropionyl-methionine sulfone methyl ester hydrochloride N-(tert-butoxycarbonyl-2(S)-[2(S)-amino-3(S)-methyl] pentyloxy-3-phenylpropionyl-methionine sulfone methyl ester was treated with HCl gas in ethyl acetate and the solvent was evaporated in vacuo to afford the title compound.

$^1$H NMR (CD$_3$OD) δ 0.85 (3H, d, J=6 Hz), 0.94 (3H, t, J=6 Hz), 1.20 (1H, m), 1.52 (1H, m), 1.72 (1H, m), 2.14 (1H, m), 2.38 (1H, m), 2.98 (3H, s), 2.90–3.20 (4H, m), 3.25 (1H, m), 3.57 (1H, dd, J=12 and 6 Hz), 3.73 (1H, dd, J=12 and 9 Hz), 3.78 (3H, s), 4.15 (1H, m), 4.63 (1H, d, J=8.5 Hz), 7.30 (5H, m).

Step H: Preparation of 2(S)-[N-2(S)-(1-(2-Naphthylmethyl) -1H-imidazol-5-ylacetyl)amino-3(S)-methyl]pentyloxy-3-phenylpropionyl-methionine sulfone methyl ester hydrochloride To a solution of 1-(2-Naphthylmethyl)-1H-imidazol-5-ylacetic acid hydrochloride (prepared in Example 4, 67 mg, 0.21 mmol), 2(S)-[2(S)-amino-3(S)-methyl]pentyloxy-3-phenylpropionyl-methionine sulfone methyl ester hydrochloride (100 mg, 0.209 mmol) and 3-hydroxy-1,2,3-benzotriazin-4(3H)-one (HOOBT, 37.5 mg, 0.209 mmol) in dimethylformamide (4 ml) was added 1-(3-dimethylaminopropyl)-3-ethylcarbodiimide hydrochloride (EDC, 44 mg, 0.21 mmol) and triethylamine (109 ul, 0.78 mmol) and the suspension stirred overnight. After this time, sat. aq. sodium bicarbonate (7 ml) was added and the resulting precipitate filtered. The precipitate was partitioned between water (25 ml) and methylene chloride (50 ml). The organic extract was evaporated in vacuo. The residue was purified by flash chromatography eluting with 2–3% methanol/methylene chloride gradient to provide a gum. The gum was dissolved in methanol (5 ml) and treated with gaseous hydrogen chloride to pH=2 and the solution was evaporated in vacuo. The resulting gum was dissolved in methanol (2 ml) and water (20 ml) and lyophilized to give the title compound as a white foam.

$^1$H NMR (CD$_3$OD, 400 MHz) δ 8.93 (1H, s), 8.35 (1H, d, J=8.7 Hz), 8.14 (1H, d, J=8.7 Hz), 7.94 (1H, d, J=8.6 Hz), 7.92-7.83 (2H, m), 7.77 (1H, s), 7.58-7.49 (3H, m), 7.38 (1H, d, J=8.4 Hz), 7.23-7.10 (5H, m), 5.62 (1H, d, J=15.5 Hz), 5.61 (1H, d, J=15.5 Hz), 4.56 (1H, m), 4.05 (1H, dd, J=4.0 and 7.4 Hz), 3.90 (1H, m), 3.70 (2H, s), 3.66 (3H, s), 3.57 (1H, dd, J=3.5 and 9.9 Hz), 3.47 (1H, dd, J=7.0 and 9.9 Hz), 3.04 (1H, dd, J=4.0 and 14.1 Hz), 2.96 (1H, m), 2.91 (1H, dd, J=7.5 and 14.1 Hz), 2.90 (3H, s), 2.80 (1H, m), 2.27 (1H, m), 2.09 (1H, m), 1.50 (1H, m), 1.43 (1H, m), 1.07 (1H, m), 0.84 (3H, t, J=7.4 Hz) and 0.77 (3H, d, J=6.7 Hz) ppm. Anal. Calcd for C$_{37}$H$_{46}$N$_4$O$_7$S.2.3 HCl: C, 57.36; H, 6.28; N, 7.23. Found: C, 57.40; H, 6.20; N, 7.38. FAB HRMS exact mass calcd for C$_{37}$H$_{47}$N$_4$O$_7$S 691.316547 (MH$^+$), found 691.316460.

EXAMPLE 15

Preparation of 2(S)-[N-2(S)-(1-(2-Naphthylmethyl)-1H-imidazol-5-ylacetyl)amino-3(S)-methyl] pentyloxy-3-phenylpropionyl-methionine Sulfone Trifluoroacetate Following the procedure described in Example 9, Step B, but substituting the methyl ester from Example 14 provided the title compound.

$^1$H NMR (CD$_3$OD, 400 MHz) δ 8.93 (1H, s), 8.27 (1H, d, J=8.3 Hz), 8.10 (1H, d, J=9.3 Hz), 7.94 (1H, d, J=8.6 Hz), 7.92-7.83 (2H, m), 7.75 (1H, s), 7.57-7.52 (2H, m), 7.50 (1H, s), 7.37 (1H, d, J=8.6 Hz), 7.23-7.11 (5H, m), 5.60 (1H, d, J=15 Hz), 6.59 (1H, d, J=15 Hz), 4.54 (1H, m), 4.03 (1H, dd, J=4.1 and 7.9 Hz), 3.91 (1H, m), 3.69 (1H, d, J=16.7 Hz), 3.66 (1H, d, J=16.7 Hz), 3.56 (1H, dd, J=3.4 and 10.3 Hz), 3.45 (1H, dd, J=7.0 and 9.7 Hz), 3.04 (1H, dd, J=4.2 and 15.1 Hz), 3.00 (1H, m), 2.94-2.85 (1H, m), 2.89 (3H, s), 2.80 (1H, m), 2.30 (1H, m), 2.09 (1H, m), 1.50 (1H, m), 1.43 (1H, m), 1.07 (1H, m), 0.83 (3H, t, J=6.4 Hz) and 0.75 (3H, d, J=6.7 Hz) ppm. Anal. Calcd for C$_{36}$H$_{44}$N$_4$O$_7$S.2.10 TFA.0.90 H$_2$O: C, 51.78; H, 5.18; N, 6.01. Found: C, 51.78; H, 5.17; N, 6.42. FAB HRMS exact mass calcd for C$_{36}$H$_{45}$N$_4$O$_7$S 677.300897 (MH$^+$), found 677.299827.

EXAMPLE 16

Preparation of 2(S)-[N-2(S)-(1-(2-Naphthylmethyl)-1H-imidazol-5-ylethyl)amino-3(S)-methyl] pentyloxy-3-phenylpropionyl-methionine Methyl Ester Bis Trifluoroacetate Step A: Preparation of 2(S)-[2(S)-t-butoxycarbonylamino-3(S)-methyl]-pentyloxy-3-phenylpropionyl-methionine methyl ester The title compound was prepared in the same fashion as that described in Example 14, Step F, using methionine methyl ester in place of methionine sulfone methyl ester.

NMR (CD$_3$OD) δ 0.78 (3H, d, J=6 Hz), 0.89 (3H, t, J=6 Hz), 1.11 (1H, m), 1.40–1.60 (2H, m), 1.47 (9H, s), 1.90–2.10 (2H, m), 2.06 (3H, s), 2.20–2.40 (2H, m), 2.90 (1H, dd, J=14.7 and 5.0 Hz), 3.05 (H, dd, J=14.5 and 3.0 Hz), 3.38 (1H, dd, J=8.6 and 7.0 Hz), 3.50–3.60 (2H, m), 3.71 (3H, s), 3.97 (1H, dd, J=7.5 and 4.0 Hz), 4.60 (1H, m), 6.60 (1H, d, J=10 Hz), 7.24 (5H, m).

Step B: Preparation of 2(S)-[2(S)-amino-3(S)-methyl]-pentyloxy-3-phenylpropionyl-methionine methyl ester hydrochloride The product of Step A was converted to the title compound using the method of Example 14, Step G.

$^1$H NMR (CD$_3$OD) δ 0.84 (3H, d, J=6 Hz), 0.93 (3H, t, J=6 Hz), 1.20 (1H, m), 1.45–1.60 (1H, m), 1.70 (1H, m), 1.80–2.20 (2H, m) 2.08 (3H, s), 2.50-2.30 (2H, m), 2.98 (1H, dd, J=14.7 and 5 Hz), 3.11 (1H, dd, J=14.5 and 3.0 Hz), 3.20–3.30 (1H, m), 3.57 (1H, m), 3.70 (1H, m), 3.73 (3H, s), 4.12 (H, dd, J=8.6 and 6.0 Hz), 4.60 (1H, m), 7.30 (5H, m).

Step C: Preparation of 2(S)-[N-2(S)-(1-(2-Naphthylmethyl) -1H-imidazol-5-ylethyl)amino-3(S)-methyl]pentyloxy-3-phenylpropionyl-methionine methyl ester bis trifluoroacetate Following the procedure described in Example 13, Step C, but substituting 1-(2-naphthylmethyl)-1H-imidazol-5-ylacetaldehyde (30) and 2(S)-[2(S)-amino-3(S)-methyl] pentyloxy-3-phenylpropionyl-methionine methyl ester hydrochloride, the title compound was obtained.

$^1$H NMR (CD$_3$OD, 400 MHz) δ 8.95 (1H, s), 7.96 (1H, d, J=8.5 Hz), 7.89 (2H, m), 7.79 (1H, s), 7.55 (2H, m), 7.47 (1H, s), 7.38 (1H, d, 8.4 Hz), 7.21 (4H, m), 7.15 (1H, m), 5.65 (2H, s, 4.63 (1H, dd, J=4.4 and 19.5 Hz), 4.15 (1H, dd, J=4.3 and 18.7 Hz), 3.67 (3H, s), 3.57 (2H, m), 3.43-3.15 (2H, m), 3.11-3.00 (4H, m), 2.88 (1H, dd, J=9 and 14.4 Hz), 2.51 (1H, m), 2.40 (1H, m), 2.10 (1H, m), 2.03 (3H, s), 1.95 (1H, m), 1.68 (1H, m), 1.35 (1H, m), 1.09 (1H, m), 0.86 (3H, t, J=7.2 Hz) and 0.74 (3H, d, J=6.9 Hz) ppm. Anal. Calcd for C$_{37}$H$_{48}$N$_4$O$_4$S.2.45 TFA: C, 54.45; H, 5.50; N, 6.06. Found: C, 54.37; H, 5.51; N, 6.15. FAB HRMS exact mass calcd for C$_{37}$H$_{49}$N$_4$O$_4$S 645.34745 (MH$^+$), found 645.34518.

EXAMPLE 17

Preparation of 2(S)-[N-2(S)-(1-(2-Naphthylmethyl)-1H-imidazol-5-ylethyl)amino-3(S)-methyl] pentyloxy-3-phenylpropionyl-methionine Bis Trifluoroacetate Following the procedure described in Example 2, Step D, but substituting the methyl ester from Example 16 provided the title compound.

¹H NMR (CD₃OD, 400 MHz) δ 8.89 (1H, s), 7.95 (1H, d, J=8.5 Hz), 7.93-7.84 (2H, m), 7.77 (1H, s), 7.58-7.51 (2H, m), 7.45 (1H, s), 7.37 (1H, dd, J=1.7 and 8.3 Hz), 7.26-7.17 (4H, m), 7.15 (1H, m), 5.65 (2H, s), 4.59 (1H, dd, J=4.5 and 9.4 Hz), 4.14 (1H, dd, J=3.8 and 8.9 Hz), 3.56 (2H, d, J=3.8 Hz), 3.37-2.96 (6H, m), 2.88 (1H, dd, J=8.8 and 14.2 Hz), 2.52 (1H, m), 2.41 (1H, m), 2.16 (1H, m), 2.03 (3H, s), 1.97 (1H, m), 1.66 (1H, m), 1.32 (1H, m), 1.08 (1H, m), 0.85 (3H, t, J=7.1 Hz) and 0.74 (3H, d, J=7.1 Hz) ppm. Anal. Calcd for $C_{36}H_{46}N_4O_4S \cdot 2.95$ TFA$\cdot 1.00$ H₂O: C, 51.08; H, 5.21; N, 5.69. Found: C, 51.07; H, 5.22; N, 5.83. FAB MS calcd for $C_{36}H_{47}N_4O_4S$, 631 (MH⁺), found 631.

EXAMPLE 18

Preparation of N-[2(S)-(1-methyl-imidazol-4-yl acetyl)amino-3(S)-methylpentyl]-N-(1-naphthylmethyl)-glycyl-methionine Methyl Ester Trifluoroacetate Salt 1-Methyl-4-imidazole acetic acid (0.070 g, 0.395 mmol), dissolved in DMF (5 mL), was treated with HOBT (0.053 g, 0.040 mmol), EDC (0.075 g, 0.395 mmol), and N-[2(S)-amino-3-methylpentyl]-N-(1-naphthylmethyl)-glycyl-methionine methyl ester hydrochloride (10, 0.175 g, 0.395 mmol). The pH was adjusted to 7.5 with Et₃N (0.055 mL, 0.395 mmol) and the mixture was stirred at ambient temperature for 72 h. The mixture was concentrated and the residue was partitioned between EtOAc (30 mL) and saturated NaHCO₃ solution (25 mL). The aqueous layer was extracted with EtOAc (2×20 mL). The combined organic layer was washed with brine (1×25 mL), dried (Na₂SO₄), and evaporated in vacuo to give a crude product which was purified by chromatography (silica gel, eluting with 99:1 to 97:3 CH₂Cl₂:MeOH) to give the amine. This material was converted to the trifluroracetate salt by dissolving in 0.1% TFA in H₂O and lyophilization to give the title compound. ¹H NMR (CD₃OD) δ 8.72 (1H, s), 8.30-8.20 (1H, m), 8.00-7.90 (2H, m), 7.45-7.70 (4H, m), 7.34 (1H, s), 4.80-4.65 (1H, m), 4.60-4.40 (2H, m ), 4.20-4.10 (1H, m ), 3.86 (3H, s), 3.70 (3H, s), 3.85-3.50 (4H, m), 3.40-3.30 (1H, m), 3.20-3.05 (1H, m), 2.40-2.20 (2H, m), 2.00 (3H, s), 2.00-1.90 (1H, m), 1.82-1.65 (1H, m), 1.65-1.52 (1H, m), 1.50-1.35 (1H, m), 1.25-1.07 (1H, m), 1.00-0.85 (6H, m). Anal. Calcd for $C_{31}H_{43}N_5O_4S \cdot 3$ TFA: C, 48.10; H, 5.02; N, 7.58. Found: C, 48.36; H, 5.30; N, 7.77.

EXAMPLE 19

Preparation of N-[2(S)-(1-methyl-1H-imidazoleacetyl)amino-3(S)-methylpentyl]-N-(1-naphthylmethyl)-glycyl-methionine N-[2(S)-(1-Methyl-4-imidazoleacetyl)amino-3(S)-methylpentyl]-N-(1-naphthylmethyl)-glycyl-methionine methyl ester (prepared in Example 18, 0.081 g, 0.139 mmol) was dissolved in MeOH (5 ml), cooled to 0° C., and 1N NaOH (0.557 ml, 0.557 mmol) was added. The mixture was stirred at ambient temperature for 4 h and evaporated in vacuo. The resulting residue was dissolved in H₂O (5 ml) and neutralized with 1N HCl (0.557 ml, 0.557 mmol). The aqueous layer was washed with EtOAc (3×10 ml). The organic layers were combined, dried (Na₂SO₄), and evaporated in vacuo to give a crude product. Purification by preparative HPLC (Vydac column eluting with acetonitrile/ 0.1% TFA in H₂O gradient) and lyophilization gave the title compound. ¹H NMR (CD₃OD) δ 8.72 (1H, s), 8.31-8.23 (1H, m), 8.02-7.90 (2H, m), 7.70-7.45 (4H, m), 7.35 (1H, s), 4.93-4.74 (1H, m), 4.58 (1H, d, J=13 Hz), 4.45-4.36 (1H, m), 4.20-4.10 (1H, m), 3.89 (3H, s), 3.86-3.52 (4H, m), 3.45-3.30 (1H, m), 3.22-3.09 (1H, m), 2.45-2.20 (2H, m), 2.00 (3H, s), 2.10-1.92 (1H, m), 1.83-1.68 (1H, m), 1.68-1.52 (1H, m), 1.52-1.37 (1H, m), 1.26-1.08 (1H, m), 1.00-0.85 (6H, m). Anal. Calcd for $C_{30}H_{41}N_5O_4S \cdot 2.75$ CF₃CO₂H: C, 48.38; H, 5.00; N, 7.95. Found: C, 48.53; H, 5.05; N, 8.11.

EXAMPLE 20

Preparation of N-[2(S)-1-(2-naphthylmethyl)-1H-imidazol-5-ylacetyl]amino-3(S)-methylpentyl]-N-(cyclopropylmethyl)-glycylmethionine methyl ester bis trifluoroacetate salt Step A: Preparation of N-[2(S)-t-Butoxycarbonylamino)-3-methylpentyl]-N-(cyclopropylmethyl)glycine methyl ester N-[2(S)-t-Butoxycarbonylamino)-3(S)-methylpentyl] glycine methyl ester (6, 287.8 mg, 0.9980 mmol) was dissolved in 1,2-dichloroethane (7.0 ml). 4A Molecular sieves (207 mg), cyclopropane-carboxaldehyde (75 ml, 1.0 mmol), and sodium triacetoxyborohydride (1.075 g, 5.072 mmol) were added. The mixture was stirred under argon at ambient temperature for 16 h and filtered. The filtrate was diluted with EtOAc (50 mL) and washed with saturated aq NaHCO₃ (2×25 ml) and saturated aq NaCl (25 mL). The organic layer was dried (Na₂SO₄) and evaporated in vacuo. The crude product was purified by chromatography (silica gel, 1:19 to 1:9 EtOAc/CH₂Cl₂) to give the title compound. ¹H NMR (CDCl₃, 400 MHz): δ 4.85 (1H, br s), 3.69 (3H, s), 3.64-3.54 (1H, m), 3.70 (1H, d, J=18 Hz), 3.30 (1H, d, J=18 Hz), 2.74 (1H, dd, J=14 and 5 Hz), 2.57-2.42 (3H, m), 1.80-1.68 (1H, m), 1.50-1.36 (1H, m), 1.44 (9H, s), 1.15-1.02 (1H, m), 0.91 (3H, t, J=7 Hz), 0.86 (3H, d, J=7 Hz), 0.86-0.76 (1H, m), 0.54-0.43 (2H, m), 0.09 (2H, d, J=5 Hz).

Step B: Preparation of N-[2(S)-t-Butoxycarbonylamino)-3-methylpentyl]-N-(cyclopropylmethyl)glycine N-[2(S)-t-Butoxycarbonylamino)-3-methylpentyl]-N-(cyclopropylmethyl)glycine methyl ester (268 mg, 0.783 mmol) was dissolved in MeOH (40 ml). After cooling to 0° C. under argon, 1N aq LiOH (1.0 ml, 1.0 mmol) was added. After stirring at ambient temperature for 18 h, additional 1N aq LiOH (1.0 ml, 1.0 mmol) was added. After stirring at ambient temperature for 6 h, additional 1N aq LiOH (1.0 ml, 1.0 mmol) was added. After stirring for 18 h at ambient temperature, 1N aq HCl (4.0 mL, 4 mmol) was added and the reaction was evaporated in vacuo. The resulting residue was dissolved in H₂O (10 ml) and acidified with 1N aq HCl to pH=2. Residual methanol was evaporated in vacuo and the remaining aqueous material lyophilized to give the title compound. ¹H NMR (CD₃OD, 400 MHz): δ 3.86-3.76 (2H, m), 3.62 (1H, d, J=15 Hz), 3.47 (1H, br d), 3.28-3.14 (2H, m), 3.12-3.03 (1H, m), 1.64-1.43 (2H, m), 1.47 (9H, s), 1.26-1.10 (2H, m), 0.98-0.90 (6H, m), 0.80-0.68 (2H, m), 0.51-0.41 (2H, m).

Step C: Preparation of N-[2(S)-t-Butoxycarbonylamino)-3-methylpentyl]-N-(cyclopropylmethyl)glycylmethionine methyl ester The title compound was prepared in the same fashion as that described in Example 1, Step G, but using the compound described in Step B.

¹H NMR (CDCl₃, 400 MHz): δ 8.02 (1H, br d), 4.78-4.68 (1H, m), 4.67 (1H, td, J=9 and 6 Hz), 3.75 (3H, s), 3.70-3.60 (1H, m), 3.31 (1H, d, J=17 Hz), 3.18 (1H, d, J=17 Hz), 2.67 (1H, dd, J=9 and 4 Hz), 2.54 (2H, t, J=8 Hz), 2.54-2.44 (2H, m), 2.43-2.35 (1H, m), 2.30-2.20 (1H, m), 2.16-2.06 (1H, m), 2.10 (3H, s), 1.63-1.52 (1H, m), 1.50-1.40 (1H, m), 1.44 (9H, s), 1.17-1.05 (1H, m), 0.93 (3H, d, J=8 Hz), 0.91 (3H, t, J=8 Hz), 0.90-0.80 (1H, m), 0.56-0.46 (2H, m), 0.15 (2H, d, J=6 Hz).

Step D: Preparation of N-[2(S)-Amino-3-methylpentyl]-N-(cyclopropylmethyl)glycylmethionine methyl ester hydrochloride N-[2(S)-t-Butoxycarbonylamino)-3-methylpentyl]-N-(cyclopropylmethyl)-glycylmethionine methyl ester (22.8 mg, 0.0481 mmol) was dissolved in EtOAc (1.5 mL) and cooled to 0° C. HCl was bubbled through the mixture until saturated. After 30 min, the mixture was evaporated in vacuo to give the title compound.

$^1$H NMR (CD$_3$OD, 400 MHz): δ 4.68 (1H, dd, J=9 and 5 Hz), 4.28-4.00 (2H, m), 3.74 (3H, s), 3.70-3.45 (2H, m), 3.40-3.00 (3H, m), 2.67-2.51 (2H, m), 2.23-1.95 (2H, m), 2.10 (3H, br s), 1.87-1.86 (1H, m), 1.60- 1.49 (1H, m), 1.34-1.21 (1H, m), 1.20-1.10 (1H, m), 1.03 (3H, d, J=7 Hz), 1.01 (3H, t, J=7 Hz), 0.82-0.72 (2H, m), 0.50-0.40 (2H, m).

Step E: Preparation of N-[(2S)-1-(2-naphthylmethyl)-1H-imidazol-5-ylacetyl]amino-(3S)-methylpentyl]-N-cyclopropylmethyl)-glycylmethionine methyl ester bis trifluoroacetate salt The title compound was prepared in the same fashion as that described in Example 1, Step I, but using the compound prepared in Step D.

$^1$H NMR (CD$_3$OD, 400 MHz): δ 8.93 (1H, s), 7.95 (1H, d, J=9 Hz), 7.93-7.85 (2H, m), 7.80 (1H, s), 7.60-7.53 (3H, m), 7.42 (1H, dd, J=9 and 2 Hz), 5.68 (2H, s), 4.69-4.45 (1H, m), 4.30-3.90 (3H, m), 3.90-3.80 (2H, m), 3.69 (3H, s), 3.60-3.45 (1H, m), 3.40-3.14 (3H, m), 2.60-2.40 (2H, m), 2.15-2.05 (1H, m), 2.03 (3H, s), 2.00-1.85 (1H, m), 1.60-1.52 (1H, m), 1.50-1.40 (1H, m), 1.25-1.15 (1H, m), 1.12-1.05 (1H, m), 0.98-0.90 (6H, m), 0.80-0.68 (2H, m), 0.50-0.40 (2H, m). FAB HRMS exact mass calcd for C$_{34}$H$_{48}$N$_5$O$_4$S: 622.342702 (MH$^+$); found 622.343884.

EXAMPLE 21

Preparation of N-[(2S)-1-(2-naphthylmethyl)-1H-imidazol-5-ylacetyl]amino-(3S)-methylpentyl]-N-(cyclopropylmethyl)-glycylmethionine Bis Trifluoroacetate Salt N-[(2S)-N-(2-Napthylmethyl)1H-imidazol-5-ylacetyl]amino-(3S)-methylpentyl]-N-(cyclopropylmethyl)-glycylmethionine methyl ester (19.8 mg, 0.0319 mmol) was dissolved in MeOH (0.60 ml), cooled to 0° C. under argon, and treated with 1.0N aq LiOH (38 ml, 0.038 mmol). After stirring at ambient temperature for 16 h, the reaction was diluted with MeOH (1.5 ml) and purified by preparative HPLC (chromatography method A) to give the title compound as its bis trifluoroacetate salt after lyophilization. $^1$H NMR (CD$_3$OD, 400 MHz): δ 8.95 (1H, s), 7.95 (1H, d, J=9 Hz), 7.94-7.85 (2H, m), 7.82 (1H, s), 7.62-7.52 (3H, m), 7.44 (1H, dd, J=9 and 1 Hz), 5.60 (2H, s), 4.65-4.50 (1H, m), 4.23-4.05 (2H, m), 4.01-3.93 (1H, m), 3.89 (1H, d, J=19 Hz), 3.82 (1H, d, J=19 Hz), 3.52 (1H, d, J=14 Hz), 3.30-3.05 (3H, m), 2.61-2.40 (2H, m), 2.20-2.10 (1H, m), 2.05 (3H, s), 2.00-1.89 (1H, m), 1.62-1.52 (1H, m), 1.50-1.40 (1H, m), 1.25-1.04 (2H, m), 0.97 (3H, d, J=7 Hz), 0.92 (3H, t, J=7 Hz), 0.79-0.65 (2H, m), 0.50-0.40 (2H, m). Anal. Calcd for C$_{33}$H$_{45}$N$_5$O$_4$S.2.70 TFA.0.45 H$_2$O: C, 49.93; H, 5.30; N, 7.58. Found: C, 49.90; H, 5.29; N, 7.92. FAB HRMS exact mass calcd for C$_{33}$H$_{46}$N$_5$O$_4$S: 608.327052 (MH$^+$); found 608.326603.

EXAMPLE 22

Preparation of N-[2(S)-[(5(R,S)-Methylpyroglutamyl)amino]-3(S)-methylpentyl]-N-(1-naphthylmethyl)-glycylmethionine Methyl Ester Trifluoroacetate Salt-diastereomers A (31) and B (32)

N-[2(S)-amino-3-methylpentyl)-N-(1-naphthylmethyl)-glycyl-methionine methyl ester hydrochloride (10, 186.1 mg, 0.349 mmol) was dissolved in methylene chloride (3 mL). DL-2-Methyl-5-pyrrolidone-2-carboxylic acid (K. Pfister III, W. J. Leanza, J. P. Conbere, H. J. Becker, A. R. Matzuk, and E. F. Rogers, *J. Am. Chem. Soc.*, 77:697–700 (1955), 50.2 mg, 0.351 mmol) was added followed by triethylamine (270 mL, 1.94 mmol). The mixture was cooled to 0° C. under argon and treated with bis(2-oxo-3-oxazolidinyl)phosphinic chloride (BOP-Cl, 133.3 mg. 0.5236 mmol). The reaction was stirred for 18 h at ambient temperature, diluted with EtOAc (20 mL), washed with saturated aq NaHCO$_3$ (20 mL), saturated aq NaCl (20 mL), dried (Na$_2$SO$_4$) and evaporated in vacuo to give the crude product as a mixture of diastereomers. Purification by chromatography (silica gel, 1:40 MeOH/CH$_2$Cl$_2$) gave the two diastereomeric products as an inseparable mixture. Separation of the diastereomers was accomplished through prep plate chromatographies (silica gel, 3–5% MeOH/CH$_2$Cl$_2$) to give the high Rf diastereomer (31) and the low Rf diastereomer (32) as colorless residues. Final purification of each diastereomer was accomplished by chromatography method A. Compounds 31 and 32 were obtained as the trifluoroacetate salts by lyophilization of appropriate column fractions. 31:

$^1$H NMR (CD$_3$OD, 400 MHz): δ 8.25-8.17 (1H, m), 7.95-7.82 (2H, m), 7.68-7.40 (4H, m), 5.10-2.80 (6H, m), 4.50-4.30 (1H, m), 4.10-3.95 (1H, m), 3.65 (3H, s), 2.60-0.90 (17H, m), 0.83 (3H, d, J=7 Hz), 0.78 (3H, t, J=8 Hz). Anal. Calcd for C$_{31}$H$_{44}$N$_4$O$_5$S.1.10 TFA.0.10 H$_2$O: C, 56.01; H, 6.41; N, 7.87. Found: C, 56.02; H, 6.29; N, 8.04. FAB HRMS exact mass calcd for C$_{31}$H$_{45}$N$_4$O$_5$S: 585.311068 (MH$^+$); found 585.311153.

32:

$^1$H NMR (CD$_3$OD, 400 MHz): δ 8.25-8.15 (1H, m), 7.95-7.81 (2H, m), 7.65-7.38 (4H, m), 5.00-2.80 (6H, m), 4.42-4.28 (1H, m), 4.05-3.95 (1H, m), 3.63 (3H, s), 2.70-1.00 (17H, m), 0.85 (3H, br d, J=7 Hz), 0.80 (3H, br t, J=7 Hz). Anal. Calcd for C$_{31}$H$_{44}$N$_4$O$_5$S.1.05 TFA.0.20 H$_2$O: C, 56.14; H, 6.47; N, 7.91. Found: C, 56.17; H, 6.47; N, 8.12. FAB HRMS exact mass calcd for C$_{31}$H$_{45}$N$_4$O$_5$S: 585.311068 (MH$^+$); found 585.311694.

EXAMPLE 23

Preparation of N-[2(S)-[(5(R,S)-methyl-pyroglutamyl)amino]-3(S)-methylpentyl]-N-(1-naphthylmethyl)-glycylmethionine Trifluoroacetate Salt N-[2(S)-[(5(R,S)-Methyl-pyroglutamyl)amino]-3(S)-methylpentyl]-N-(1-naphthylmethyl)-glycyl-methionine methyl ester (31, 32.3 mg, 0.0552 mmol) was dissolved in MeOH (1.5 mL) under argon and treated with 1.0N aq LiOH (66 μL, 0.066 mmol). The reaction was stirred at ambient temperature for 18 h, treated with glacial acetic acid (2 drops), and purified by chromatography method A to give, after lyophilization, the title compound as a 2:1 mixture of diastereomers as their trifluoroacetate salts. $^1$H NMR (CD$_3$OD, 400 MHz): δ 8.29 (1H, d, J=8 Hz), 8.00-7.89 (2H, m), 7.78-7.45 (4H, m), 5.00-2.80 (8H, m), 2.60-1.00 (17H, m), 0.96-0.84 (6H, m). Anal. Calcd for C$_{30}$H$_{42}$N$_4$O$_5$S.1.25 TFA.0.20 H$_2$O: C, 54.45; H, 6.14; N, 7.82. Found: C, 54.46; H, 6.14; N, 7.91. FAB HRMS exact mass calcd for C$_{30}$H$_{43}$N$_4$O$_5$S: 571.295418 (MH$^+$); found 571.295373.

EXAMPLE 24

Preparation of N-[2(S)-[(5(R,S)-methylpyroglutamyl)amino]-3(S)-methylpentyl]-N-(1-naphthylmethyl)-glycylmethionine Trifluoroacetate Salt Following the procedure described in Example 23, but substituting the methyl ester 32 from Example 22, the title compound was prepared.

¹H NMR (CD₃OD, 400 MHz): δ 8.36-8.26 (1H, m), 7.97 (2H, br d, J=8 Hz), 7.80-7.44 (4H, m), 5.00-3.00 (8H, m), 2.60-1.10 (17H, m), 0.99-0.84 (6H, m). Anal. Calcd for $C_{30}H_{42}N_4O_5S \cdot 1.40$ TFA$\cdot 0.15$ H₂O: C, 53.74; H, 6.01; N, 7.64. Found: C, 53.73; H, 5.99; N, 7.74. FAB HRMS exact mass calcd for $C_{30}H_{43}N_4O_5S$: 571.295418 (MH⁺); found 571.296351.

EXAMPLE 25

Preparation of N-[2(S)-((N-methylpyroglutamyl) amino)-3(S)-methylpentyl]-N-(1-naphthylmethyl)-glycyl-methionine Methyl Ester Trifluoroacetate Salt N-methylpyroglutamate [E. Hardegger and H. Ott, *Helv. Chim Acta*, 38:312 (1955), 51 mg, 0.35 mmol)], dissolved in DMF (2.5 ml), was treated with HOBT (48 mg, 0.35 mmol), EDC (81 mg, 0.42 mmol), N-[2(S)-amino-3(S)-methylpentyl)-N-(1-naphthylmethyl)glycyl-methionine methyl ester hydrochloride (10, 150 mg, 0.28 mmol), and triethylamine (0.079 ml, 0.56 mmol). The mixture was stirred at room temperature for 24 hours. The mixture was partitioned between ethyl acetate and 10% citric acid solution and the organic phase was washed three times with saturated NaHCO₃, brine, and dried (MgSO₄). The solution was filtered through celite and evaporated in vacuo. The crude product was chromatographed (5% MeOH in EtOAc) and further purified by preparative HPLC (Waters PrepPak C-18 eluting with CH₃CN/0.1% TFA in H₂O) to give, after lyophilization, the title compound.

¹H NMR (CD₃OD) δ 8.35 (1H, d), 8.0 (2H, m), 7.7 (4H, m), 5.1 (1H, m), 4.75 (1H, m), 4.55 (1H, m), 4.05 (4H, m), 3.75 (3H, s), 3.60 (1H, m), 3.20 (1H, m), 2.70 (3H, s), 2.30 (6H, m), 2.00 (4H, m), 1.85 (1H, m), 1.65 (1H, m), 1.45 (1H, m), 1.25 (1H, m), 0.95 (6H, m). FAB MS calcd for $C_{31}H_{45}N_4O_5S$ 585 (MH⁺), found 585. Anal. Calcd for $C_{31}H_{44}N_4O_5S \cdot 1.35$TFA$\cdot 1.60$H₂O: C, 52.73; H, 6.38; N, 7.30. Found: C, 52.75; H, 6.00; N, 7.70

EXAMPLE 26

Preparation of N-[2(S)-((N-methylpyroglutamyl)-amino)-3(S)-methylpentyl]-N-(1-naphthylmethyl)-glycyl-methionine N-[2(S)-((N-Methylpyroglutamyl)-amino)-3(S)-methylpentyl]-N-(1-naphthylmethyl)-glycyl-methionine methyl ester trifluoroacetate salt (prepared in Example 25, 112 mg, 0.19 mmol) was dissolved in methanol (5 ml) and treated with 0.76 ml of 1N LiOH. The mixture was stirred for 4 hours at room temperature, then treated with 0.76 ml of 1N HCl. The solvent was evacuated in vacuo. The crude product was purified by preparative HPLC (Waters PrepPak C-18 eluting with CH₃CN/0.1% TFA in H₂O) to give, after lyophilization, the title compound.

¹H NMR (CD₃OD) δ 8.35 (1H, d), 8.00 (2H, m), 7.65 (4H, m), 5.10 (1H, m), 4.75 (1H, m), 4.50 (1H, m), 4.05 (4H, m), 3.60 (1H, m), 3.25 (1H, m), 2.70 (3H, s), 2.30 (6H, m), 2.05 (3H, s), 1.85 (2H, m), 1.60 (1H, m), 1.45 (1H, m), 1.20 (1H, m), 0.95 (6H, m). FAB MS calcd for $C_{30}H_{43}N_4O_5S$: 571 (MH⁺), found 571. Anal. Calcd for $C_{30}H_{42}N_4O_5S \cdot 1.60$TFA$\cdot 0.55$H₂O: C, 52.25; H, 5.90; N, 7.34. Found: C, 52.27; H, 5.92; N, 7.71.

EXAMPLE 27

Preparation of N-[2(S)-(N-formylprolylamino)-3(S)-methylpentyl]-N-(1-naphthylmethyl)-glycyl-methionine methyl ester trifluoroacetate salt N-formyl-L-proline [T. Sawayama, et al, *Chem. Pharm. Bull.*, 38(2), 529–531 (1990), 44.3 mg, 0.31 mmol], dissolved in DMF (3 ml), was treated with HOBT (46 mg, 0.34 mmol), EDC (81 mg, 0.42 mmol), N-[2(S)-amino-3-methylpentyl)-N-(1-naphthylmethyl)glycyl-methionine methyl ester hydrochloride (10, 150 mg, 0.28 mmol), and triethylamine (0.079 ml, 0.56 mmol). The mixture was stirred at room temperature for 72 h, then partitioned between ethyl acetate and 10% citric acid solution. The organic extract was washed with saturated NaHCO₃ three times, then brine, and dried (MgSO₄). After filtration through celite and evaporation of solvent in vacuo., the crude product was purified by preparative HPLC (Waters PrepPak C-18 eluting with CH₃CN/0.1% TFA in H₂O) to give, after lyophilization, the title compound. ¹H NMR (CD₃OD) 8.35 (1H, m), 8.20 (1H, s), 8.00 (2H, m), 7.65 (4H, m), 5.10 (1H, m), 4.65 (2H, m), 4.10 (4H, m), 3.75 (3H, s), 3.60 (3H, m), 3.10 (1H, m), 2.40 (2H, m), 1.90 (8H, m), 1.55 (3H, m), 1.20 (1H, m), 0.90 (6H, m). FAB MS calcd for $C_{31}H_{45}N_4O_5S$ 585 (MH⁺), found 571. Anal. Calcd for $C_{31}H_{44}N_4O_5S \cdot 1.40$TFA$\cdot 0.20$H₂O: C, 54.28; H, 6.11; N, 7.47. Found: C, 54.25; H, 6.16; N, 7.69.

EXAMPLE 28

Preparation of N-[2(S)-(N-formylprolylamino)-3(S)-methylpentyl]-N-(1-naphthylmethyl)-glycyl-methionine The procedure described in Example 26, substituting the methyl ester prepared in Example 27 was used to obtain the title compound.

FAB MS m/z 571 (M+1). Anal. Calcd for $C_{30}H_{42}N_4O_5S_1 \cdot 1.75$ TFA: C, 52.24; H, 5.72; N, 7.27. Found: C, 52.19; H, 5.82; N, 7.61.

EXAMPLE 29

Preparation of N-[2(S)-(N'-(4-nitrobenzyl)-pyroglutamyl)-amino)-3(S)-methylpentyl]-N-(1-naphthylmethyl)-glycyl-methionine Methyl Ester Hydrochloride Salt( )

Step A: Preparation of (S)-N-(4-nitrobenzyl)pyroglutamic acid methyl ester (S)-Pyroglutamic acid methyl ester (0.200 g, 1.40 mmol) was dissolved in dry THF (5 ml) and NaH (0.061 g, 1.5 mmol) was added. After gas evolution ceased, 4-nitrobenzyl bromide (0.332 g, 1.54 mmol) was added and the mixture stirred for 1 h. The reaction was quenched with saturated NaHCO₃ solution (40 mL) and extracted with EtOAc (2×50 ml). The organic layers were washed with water, brine, dried (MgSO₄), filtered, and concentrated to give the title compound as a solid. ¹H NMR (CDCl₃) δ 8.19 (d, 2H, J=8.6 Hz), 7.40 (d, 2H, J=8.6 Hz), 5.29 (d, 1H, J=15 Hz), 4.19 (d, 1H, J=15 Hz), 4.02 (dd, 1H, J=3,9 Hz), 3.79 (s, 3H), 2.54–2.67 (m, 1H), 2.42–2.51 (m, 1H), 2.27–2.39 (m, 1H), 2.11–2.21 (m, 1H).

Step B: preparation of (S)-N-(4-nitrobenzyl)pyroglutamic acid (S)-N-(4-Nitrobenzyl)pyroglutamic acid methyl ester (0.365 g, 1.31 mmol) was dissolved in 10 ml MeOH, cooled to 0° C., and 1N NaOH (5.2 ml, 5.2 mmol) was added. The reaction was stirred at room temperature for 1 h. Water (50 ml) was added and the aqueous was washed with 2×50 ml EtOAc. The aqueous was acidified with 1N HCl and extracted with 3×40 ml EtOAc. The organic layers were dried (MgSO₄), filtered, and concentrated to give the title compound as a solid.

¹H NMR (d₆-DMSO) δ 8.19 (d, 2H, J=8.7 Hz), 7.51 (d, 2H, J=8.6 Hz), 4.86 (d, 1H, J=16 Hz), 4.19 (d, 1H, J=16 Hz), 4.02–4.10 (m, 1H), 3.30 (br s, 1H), 2.29–2.41 (m, 3H), 1.96–2.05 (m, 1H).

Step C: Preparation of N-[2(S)-((4-Nitrobenzyl) pyroglutamyl)amino)-3(S)-methylpentyl]-N-(1-naphthylmethyl)-glycyl-methionine methyl ester hydrochloride salt (S)-N-(4-Nitrobenzyl)pyroglutamic acid (0.95 g, 0.36 mmol), N-[2(S)-amino-3-methylpentyl]-N-(1-naphthylmethyl)-glycyl-methionine methyl ester hydrochloride (10, 0.160 g, 0.300 mmol) and diisopropylethylamine (0.261 mL, 1.50 mmol) were dissolved in DMF (3 mL). BOP-Cl (0.137 g, 0.539 mmol) was added and the mixture was stirred at ambient temperature for 24 h. The mixture was concentrated and the residue was partitioned between EtOAc (80 mL) and saturated NaHCO$_3$ solution (25 mL). The aqueous layer was extracted with EtOAc (30 mL). The combined organic layer was washed with brine (25 mL), dried (MgSO$_4$), filtered, and concentrated to give a crude product which was purified by chromatography (silica gel, eluting with 98:2 CH$_2$Cl$_2$:MeOH). Further purification by preparative HPLC (Waters C-18 Prep Pak eluting with acetonitrile/0.1% TFA in H$_2$O gradient) gave the amine trifluoroacetate, which was converted to the hydrochloride salt by dissolving in EtOAc, bubbling HCl gas, filtering, and drying under vacuum to give the title compound. $^1$H NMR (CD$_3$OD) δ 8.29–8.41 (m, 1H), 8.17 (d, 2H, J=8 Hz), 7.92–8.08 (m, 2H), 7.64–7.76 (m, 2H), 7.48–7.64 (m, 2H), 7.33–7.48 (m, 2H), 5.03–5.18 (m, 1H), 4.59–4.72 (m, 1H), 4.39–4.52 (m, 1H), 3.81–4.27 (m, 4H), 3.72 (s, 3H), 3.14–3.28 (m, 1H), 2.50–2.73 (m, 1H), 2.19–2.50 (m, 6H), 1.85–2.13 (m, 4H), 2.01 (s, 3H), 1.67–1.85 (m, 1H), 1.41–1.53 (m, 1H), 1.24–1.38 (m, 1H), 1.02–1.19 (m, 1H), 0.72–0.94 (m, 6H). Anal. Calcd for C$_{37}$H$_{46}$N$_5$O$_7$S.1.95 HCl.0.95 H$_2$O: C, 56.04; H, 6.34; N, 8.83. Found: C, 56.07; H, 6.28; N, 8.71.

EXAMPLE 30

Preparation of N-[2(S)-((4-nitrobenzyl) pyroglutamyl)-amino)-3(S)-methylpentyl]-N-(1-naphthylmethyl)-glycyl-methionine Trifluoroacetate Salt N-[2(S)-((4-Nitrobenzyl)pyroglutamyl)amino)-3(S)-methylpentyl]-N-(1-naphthylmethyl)-glycyl-methionine methyl ester (0.050 g, 0.071 mmol) was dissolved in MeOH (1 ml), cooled to 0°, and 1N NaOH (0.283 ml, 0.283 mmol) was added. The mixture was stirred at ambient temperature for 1 h. The mixture was neutralized with 1N HCl (0.283 ml, 0.283 mmol). The aqueous layer was washed with EtOAc (3×10 ml). The organic layers were combined, dried with MgSO$_4$, filtered, and concentrated to give a crude product. Preparative HPLC (Waters C-18 Prep Pak eluting with acetonitrile/0.1% TFA in H$_2$O gradient) gave the pure title compound. $^1$H NMR (CD$_3$OD); δ 8.35 (d, 1H, J=8 Hz), 8.17 (d, 2H, J=8 Hz), 7.94–8.04 (m, 2H), 7.70–7.77 (m, 1H), 7.61 (t, 1H, J=8 Hz), 7.52–7.63 (m, 2H), 7.42 (d, 2H, J=8 Hz), 4.93–5.10 (m, 1H), 4.62–4.75 (m, 1H), 4.43–4.56 (m, 1H), 4.08–4.21 (m, 1H), 3.81–4.21 (m, 4H), 3.45–3.61 (m, 1H), 3.10–3.26 (m, 2H), 2.28–2.53 (m, 6H), 1.95–2.19 (m, 3H), 2.03 (s, 3H) 1.76–1.92 (m, 1H), 1.41–1.54 (m, 1H), 1.24–1.38 (m, 1H), 1.03–1.17 (m, 1H), 0.77–0.94 (m, 6H). Anal. Calcd for C$_{36}$H$_{44}$N$_5$O$_7$S.1.9 TFA.0.85 H$_2$O: C, 51.80; H, 5.20; N, 7.59. Found: C, 51.81; H, 5.36; N, 7.53.

EXAMPLE 31

Preparation of N-[2(S)-((N'-benzylpyroglutamyl) amino)-3(S)-methylpentyl]-N-(1-naphthylmethyl)-glycyl-methionine Methyl Ester Trifluoroacetate Salt Using the method of Example 29, substituting benzyl bromide for the p-nitrobenzyl bromide used therein, the title compound was obtained.

Anal. Calcd for C$_{37}$H$_{48}$N$_4$O$_5$S.1.65 TFA: C, 57.01; H, 5.89; N, 6.60. Found: C, 56.96; H, 5.94; N, 6.91.

EXAMPLE 32

Preparation of N-[2(S)-(N'-benzylpyro-glutamyl) amino)-3(S)-methylpentyl]-N-(1-naphthylmethyl)-glycyl-methionine Trifluoroacetate Salt The product of Example 31 was converted to the title compound as described in Example 30.

FAB MS calcd for C$_{36}$H$_{47}$N$_4$O$_5$S 647 (MH$^+$), found 647 Anal. Calcd for C$_{36}$H$_{46}$N$_4$O$_5$S.1.5 TFA: C, 57.27; H, 5.85; N, 6.85. Found: C, 57.17; H, 5.94; N, 6.79.

EXAMPLE 33

Preparation of N-[2(S)-1-(4-Fluorophenylmethyl)-1H-imidazol-5-ylacetyl)amino-3(S)-methylpentyl]-N-1-naphthylmethyl-glycyl-methionine Step A: Preparation of 1-(4-Fluorophenylmethyl)-1H-imidazol-5-ylacetic acid The title compound was prepared as the hydrogen bromide salt using the procedures described in Example 3 steps B and C replacing 4-nitrobenzyl bromide with 4-fluorobenzyl bromide.

$^1$H NMR (CD$_3$OD, 400 MHz) δ 8.89 (1H, d, J=1.3 Hz), 7.55 (1H, s), 7.50-7.30 (2H, m), 7.17 (2H, t, J=8.8 Hz), 5.43 (2H, s) and 3.82 (2H, s) ppm.

Step B: Preparation of N-[2(S)-1-(4-Fluorophenylmethyl)-1H-imidazol-5-ylacetyl)amino-3(S)-methylpentyl]-N-1-naphthylmethyl-glycyl-methionine methyl ester bis trifluoroacetate The title compound was prepared as the bis trifluoroacetate salt using the procedures described in example 2 step C using 1-(4-Fluorophenylmethyl)-1H-imidazol-5-ylacetic acid.

$^1$H NMR (CD$_3$OD, 400 MHz) δ 8.77 (1H, s), 8.28 (1H, m), 8.00-7.80 (2H, m)), 7.65-7.40 (5H, m), 7.30-7.20 (2H, m), 7.14 (2H, t, J=8.6 Hz), 5.34 (2H, m) 4.39 (2H, m), 4.13 (1H, m), 3.68 (3H, s), 3.65-3.40 (4H, m), 2.95 (1H, m), 2.40-2.15 (2H, m), 1.97 (3H, s), 1.95 (1H, m), 1.70 (1H, m), 1.60 (1H, m), 1.43 (1H, m), 1.07 (1H, m), and 1.00-0.80 (6H, m) ppm. FAB Mass spectrum, m/z=676 (M+1). Anal. calc'd for C$_{37}$H$_{46}$N$_5$O$_4$S 0.45H$_2$O, 1.65TFA; C, 55.50 H, 5.61 N, 8.03. Found: C, 55.50; H, 5.60; N, 8.23.

Step C: Preparation of N-[2(S)-1-(4-Fluorophenylmethyl)-1H-imidazol-5-ylacetyl)amino-3(S)-methylpentyl]-N-1-naphthylmethyl-glycyl-methionine bis trifluoroacetate The title compound was prepared as the bis trifluoroacetate salt using the procedure described in Example 2 step D.

$^1$H NMR (CD$_3$OD, 400 MHz) δ 8.79 (1H, s), 8.30 (1H, m), 8.00-7.80 (2H, m)), 7.65-7.40 (5H, m), 7.30-7.20 (2H, m), 7.13 (2H, t, J=8.7 Hz), 5.35 (2H, m) 4.38 (2H, m), 4.13 (1H, m), 3.80-3.40 (4H, m), 3.10 (1H, m), 2.40-2.15 (2H, m), 1.97 (3H, s), 1.95 (1H, m), 1.70 (1H, m), 1.60 (1H, m), 1.43 (1H, m), 1.07 (1H, m), and 1.00-0.80 (6H, m) ppm. FAB Mass spectrum, m/z=662 (M+1). Anal. calc'd for C$_{36}$H$_{44}$N$_5$O$_4$S 0.60H$_2$O, 2.30TFA; C, 52.16 H, 5.12 N, 7.49. Found: C, 52.18; H, 5.13; N, 7.76.

EXAMPLE 34

Preparation of N-[2(S)-([1-(4-cyanobenzyl)-1H-imidazol-5-yl]acetylamino)-3(S)-methylpentyl]-N-(1-naphthylmethyl)glycyl-methionine Isopropyl Ester Step A: Preparation of 1H-Imidazole-4-acetic acid methyl ester hydrochloride A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid.

$^1$H NMR (CDCl$_3$, 400 MHz) δ 8.85 (1H, s), 7.45 (1H, s), 3.89 (2H, s) and 3.75 (3H, s) ppm.

Step B: Preparation of 1-(Triphenylmethyl)-1H-imidazol-4-ylacetic acid methyl ester To a solution of the product from Step A (24.85 g, 0.141 mol) in dimethyl formamide (DMF) (115 ml) was added triethylamine (57.2 ml, 0.412 mol) and triphenylmethyl bromide (55.3 g, 0.171 mol) and the suspension was stirred for 24 hr. After this time, the reaction mixture was diluted with ethyl acetate (EtOAc) (1 l) and water (350 ml). The organic phase was washed with sat. aq. NaHCO$_3$ (350 ml), dried (Na$_2$SO$_4$) and evaporated in vacuo. The residue was purified by flash chromatography (SiO$_2$, 0–100% ethyl acetate in hexanes; gradient elution) to provide the title compound as a white solid.

$^1$H NMR (CDCl$_3$, 400 MHz) δ 7.35 (1H, s), 7.31 (9H, m), 7.22 (6H, m), 6.76 (1H, s), 3.68 (3H, s) and 3.60 (2H, s) ppm.

Step C: Preparation of [1-(4-cyanobenzyl)-1H-imidazol-5-yl]acetic acid methyl ester To a solution of the product from Step B (8.00 g, 20.9 mmol) in acetonitrile (70 ml) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq NaHCO$_3$ (300 ml) and CH$_2$Cl$_2$ (300 ml) and stirred at room temperature for 2 hr. The organic layer was separated, dried (MgSO$_4$) and evaporated in vacuo to afford the title compound as a white solid:

$^1$H NMR (CDCl$_3$, 400 MHz) δ 7.65 (1H, d, J=8 Hz), 7.53 (1H, s), 7.15 (1H, d, J=8 Hz), 7.04 (1H, s), 5.24 (2H, s), 3.62 (3H, s) and 3.45 (2H, s) ppm.

Step D: Preparation of [1-(4-cyanobenzyl)-1H-imidazol-5-yl]acetic acid

A solution of [1-(4-cyanobenzyl)-1H-imidazol-5-yl]acetic acid methyl ester (4.44 g, 17.4 mmol) in THF (100 ml) and 1M lithium hydroxide (17.4 ml, 17.4 mmol) was stirred at RT for 18 hr. 1M HCl (17.4 ml) was added and the THF was removed by evaporation in vacuo. The aqueous solution was lyophilised to afford the title compound containing lithium chloride as a white solid.

$^1$H NMR (CD$_3$OD, 400 MHz) d 8.22 (1H, s), 7.74 (1H, d, J=8.4 Hz), 7.36 (1H, d, J=8.4 Hz), 7.15 (1H, s), 5.43 (2H, s) and 3.49 (2H, s) ppm.

Step E: Preparation of N-[2(S)-(amino)-3(S)-methylpentyl]-N-(1-naphthylmethyl)glycine methyl ester hydrochloride A solution of N-[2(S)-(t-Butoxycarbonylamino)-3(S)-methylpentyl]N-(1-naphthylmethyl) glycine methyl ester from example 1 step E (5.90 g, 13.8 mmol) in EtOAc (100 ml) was saturated with gaseous hydrogen chloride. The resulting solution was allowed to stand at room temperature for 1 hr. The solvent was evaporated in vacuo to afford the title compound as a white solid.

$^1$H NMR (CD$_3$OD 400 MHz) δ 8.26 (1H, d, J=8.6 Hz), 7.92 (1H, d, J=7.2 Hz), 7.87 (1H, d, J=8.6 Hz), 7.63-7.42 (4H, m), 4.34 (1H, d, J=12.3 Hz), 4.26 (1H, d, J=12.3 Hz), 3.68 (3H, s), 3.13 (1H, d, J=10.3 Hz), 2.67-2.55 (2H, m), 1.46 (1H, m), 1.28 (2H, m), 1.10-0.90 (2H, m), 0.84 (3H, d, J=6.8 Hz) and 0.77 (3H, t, J=6.8 Hz) ppm.

Step F: Preparation of N-[2(S)-([1-(4-cyanobenzyl)-1H-imidazol-5-yl]acetylamino)-3(S)-methylpentyl]-N-(1-naphthylmethyl) glycine methyl ester To a solution of [1-(4-cyanobenzyl)-1H-imidazol-5-yl] acetic acid. (4.09 g, 10.24 mmol), the amine hydrochloride salt from step E (5.07 g, 10.24 mmol), HOOBT (1.67 g, 10.24 mmol), and N-methylmorpholine (2.36 ml, 21.5 mmol) in DMF (50 ml) at 0° C., was added EDC (2.16 g, 11.26 mmol). The reaction was stirred at room temperature for 18 hrs, diluted with EtOAc and the organic layer washed with sat. aq NaHCO$_3$, brine, dried (Na$_2$SO$_4$), and the solvent evaporated in vacuo. The residue was chromatographed (SiO$_2$, 3–4% MeOH in CH$_2$Cl$_2$) to afford the title compound as a white solid.

$^1$H NMR (CD$_3$OD, 400 MHz) δ 8.30 (1H, d, J=8.4 Hz), 7.84 (1H, d, J=8.0 Hz), 7.80 (1H, t, J=4.5 Hz), 7.68-7.38 (3H, m), 7.48-7.32 (4H, m), 7.10 (2H, d, J=8.0 Hz), 6.87 (1H, s), 5.24 (1H, d, J=16.7 Hz), 5.18 (1H, d, J=16.7 Hz), 4.83 (2H, s), 4.27 (1H, d, J=12.8 Hz), 4.10 (1H, d, J=12.8 Hz), 3.97 (1H, m), 3.65 (3H, s), 3.40-3.20 (2H, m), 2.92 (1H, dd, J=13.3 and 4.3 Hz), 2.60 (1H, dd, J=13.3 and 10.0 Hz), 1.48 (1H, m), 1.25 (1H, m), 0.98 (1H, m), 0.78 (3H, d, J=6.8 Hz) and 0.77 (3H, t, J=7.5 Hz) ppm. Anal. calc'd for C$_{33}$H$_{37}$N$_5$O$_3$ 1.05H$_2$O, 2.85 TFA C, 51.90; H, 4.72; N, 7.82. Found: C, 51.90; H, 4.70; N, 8.18. FAB Mass spectrum, m/z=552 (M+1).

Step G: Preparation of N-[2(S)-([1-(4-cyanobenzyl)-1H-imidazol-5-yl]acetylamino)-3(S)-methylpentyl]-N-(1-naphthylmethyl) glycine A solution of the methyl ester from step F (2.32 g, 4.21 mmol) in MeOH (20 ml) and 1M lithium hydroxide (4.70 ml, 4.70 mmol) was stirred at RT for 6 hr. The aqueous solution diluted with water (15 ml) and extracted with EtOAc (100 ml), dried (Mg$_2$SO$_4$), and the solvent evaporated in vacuo. The residue was chromatographed (SiO$_2$, 20% MeOH in CH$_2$Cl$_2$) to afford the title compound as a white solid.

$^1$H NMR (CD$_3$OD, 400 MHz) δ 8.33 (1H, d, J=8.3 Hz), 7.87 (2H, d, J=7.7 Hz), 7.78 (1H, s), 7.63 (2H, d, J=6.6 Hz), 7.57 (1H, d, J=6.4 Hz), 7.50-7.38 (4H, m), 7.17 (1H, d, J=8.3 Hz), 6.96 (1H, s), 5.32 (1H, d, J=16.6 Hz), 5.25 (1H, d, J=16.6 Hz), 4.64 (1H, d, J=13.2 Hz), 4.40 (1H, d, J=13.2 Hz), 3.99 (1H, m), 3.60-3.28 (4H, m), 3.22 (1H, dd, J=13.3 and 3.1 Hz), 2.93 (1H, dd, J=13.3 and 10.3 Hz), 1.52 (1H, m), 1.29 (1H, m), 1.06 (1H, m), 0.86-0.76 (6H, m) ppm. Anal. calc'd for C$_{32}$H$_{35}$N$_5$O$_3$ 1.00H$_2$O, C, 69.17; H, 6.71 N, 12.60. Found: C, 68.95; H, 6.37; N, 12.54. FAB Mass spectrum, m/z=538 (M+1).

Step H: Preparation of N-[2(S)-([1-(4-cyanobenzyl)-1H-imidazol-5-yl]acetylamino)-3(S)-methylpentyl]-N-(1-naphthylmethyl)glycyl-methionine isopropyl ester To a solution of the acid from step G (100 mg, 0.186 mmol) and methionine isopropyl ester hydrochloride (42.4 mg, 0.186 mmol), HOOBT (30.4 mg, 0.186 mmol) and triethylamine (0.077 ml, 0.56 mmol) in DMF (1.0 ml) was added EDC (37.5 mg, 1.96 mmol). The reaction was stirred at room temperature for 18 hrs, diluted with EtOAc and the organic layer washed with sat. aq NaHCO$_3$, brine, dried (Na$_2$SO$_4$), and the solvent evaporated in vacuo. The residue was chromatographed (SiO$_2$, 5% MeOH in CH$_2$Cl$_2$), evaporated to dryness and converted to the hydrochloride salt by treatment with aqueous HCl (0.32 ml of a 1M solution) and acetonitrile and lyophilisation, to afford the title compound as a white powder.

$^1$H NMR (CD$_3$OD, 400 MHz) δ 9.00-8.90 (1H, m), 8.38 (1H, m), 8.10-7.10 (11H, m), 5.80-4.80 (4H, m), 4.60-3.30 (11H, m), 2.60-1.70 (8H, m), 1.60 (1H, m), 1.42 (1H, m), 1.21 (6H, d, J=6.2 Hz), 0.918 (6H, br t, J=7.3 Hz) ppm. FAB HRMS exact mass calc'd for C$_{40}$H$_{51}$N$_6$O$_4$S 711.369251 (MH$^+$), found 711367663. Anal. calc'd for C$_{40}$H$_{50}$N$_6$O$_4$S 0.55H$_2$O and 2.80HCl C, 58.38; H, 6.60 N, 10.21. Found: C, 58.40; H, 6.60; N, 10.36.

EXAMPLE 35

Preparation of N-[2(S)-([1-(4-cyanobenzyl)-1H-imidazol-5-yl]acetylamino)-3(S)-methylpentyl]-N-(1-naphthylmethyl)glycyl-methionine Sulfone Methyl Ester The title compound was prepared as the hydrogen chloride salt using the procedures described in Example 34 Steps H using methionine sulfone methyl ester hydrochloride.

$^1$H NMR (CD$_3$OD, 400 MHz) δ 8.93 (1H, m), 8.39 (1H, m), 8.20-7.15 (11H, m), 5.50 (2H, m), 5.40-3.00 (15H, m), 2.95 (3H, s), 2.30 (1H, m), 2.05 (1H, m), 1.60 (1H, m), 1.45 (1H, m), 1.22 (1H, m), 0.915 (6H, m) ppm. FAB HRMS exact mass calc'd for C$_{38}$H$_{47}$N$_6$O$_6$S 715.327781 (MH$^+$), found 715.327372. Anal. calc'd for C$_{38}$H$_{47}$N$_6$O$_6$S 0.35H$_2$O and 3.25HCl C, 54.36; H, 6.00 N, 10.01. Found: C, 54.36; H, 5.99; N, 10.21.

EXAMPLE 36

Preparation of N-[2(S)-([1-(4-cyanobenzyl)-1H-imidazol-5-yl]acetylamino)-3(S)-methylpentyl]-N-(1-naphthylmethyl)glycyl-methionine Sulfone A stirred solution of the methyl ester from Example 35 (23.7 mg, 0.033 mmol) in THF (0.20 ml) and 1M lithium hydroxide (0.033 ml, 0.033 mmol) was allowed to warm from 0° C. to room temperature over 18 hrs. The reaction was quenched by the addition of trifluoroacetic acid and the solvent evaporated in vacuo. The residue was purified by preparative hplc to afford the title compound after lyophilisation.

$^1$H NMR (CD$_3$OD, 400 MHz) δ 8.89 (1H, m), 8.16 (1H, m), 7.85-7.20 (11H, m), 5.38 (2H, m), 4.31 (1H, m), 4.00 (1H, m), 3.60-3.30 (7H, m), 3.00-2.90 (3H, m), 2.81 (3H, s), 2.14 (1H, m), 1.94 (1H, m), 1.431H, m), 1.29 (1H, m), 1.04 (1H, m), 0.78 (6H, m) ppm. Anal. calc'd for C$_{37}$H$_{44}$N$_6$O$_6$S 0.45H$_2$O, 2.30 TFA C, 51.45; H, 4.90 N, 8.65. Found: C, 51.44 H, 4.89; N, 8.62. FAB HRMS exact mass calc'd for C$_{37}$H$_{45}$N$_6$O$_6$S 701.312130 (MH$^+$), found 701.313179.

EXAMPLE 37

Preparation of N-[2(S)-([1-(4-cyanobenzyl)-1H-imidazol-5-yl]acetylamino)-3(S)-methylpentyl]-N-(1-naphthylmethyl)glycyl-(3-acetylamino)alanine Methyl Ester The title compound was prepared as the hydrochloride salt using the procedures described in Example 34 Step H using (S)-N'-acetyl diaminopropionic acid methylester hydrochloride.

$^1$H NMR (CD$_3$OD, 400 MHz) δ 8.90 (1H, m), 8.38 (1H, m), 8.10-7.20 (11H, m), 5.60 (2H, m), 5.20-3.00 (10H, m), 3.60 (3H, s), 1.92 (3H, s), 1.83 (1H, s), 1.57 (1H, m), 1.43 (1H, m), 1.19 (1H, m), 0.90 (6H, m) ppm. FAB HRMS exact mass calc'd for C$_{38}$H$_{46}$N$_7$O$_5$ 680.356043 (MH$^+$), found 680.356735. Anal. calc'd for C$_{38}$H$_{45}$N$_7$O$_5$ 0.35H$_2$O and 3.05 HCl C, 57.24; H, 6.16 N, 12.30. Found: C, 57.26; H, 6.16; N, 12.40.

EXAMPLE 38

Preparation of N-[2(S)-([1-(4-cyanobenzyl)-1H-imidazol-5-yl]acetylamino)-3(S)-methylpentyl]-N-(1-naphthylmethyl)glycyl-(3-acetylamino)alanine The title compound was prepared as the trifluoroacetate salt using the procedures described in Example 36 and the methyl ester prepared in Example 37.

$^1$H NMR (CD$_3$OD, 400 MHz) δ 8.82 (1H, m), 8.40 (1H, m), 7.70 (2H, m), 7.65 (2H, d, J=8.0 Hz), 7.60-7.30 (5H, m), 7.27 (2H, d, J=8.0 Hz), 5.40 (2H, m), 4.32 (1H, m), 4.00 (1H, m), 3.70-3.10 (10H, m), 1.75 (3H, s), 1.48 (1H, s), 1.33 (1H, m), 1.08 (1H, m), 0.80 (6H, m) ppm. FAB HRMS exact mass calc'd for C$_{37}$H$_{44}$N$_7$O$_5$ 666.340393 (MH$^+$), found 666.340627. Anal. calc'd for C$_{37}$H$_{43}$N$_7$O$_5$ 0.30H$_2$O and 2.35 TFA C, 53.33; H, 4.93 N, 10.44. Found: C, 53.33; H, 4.95; N, 10.22.

EXAMPLE 39

Preparation of N-[2(S)-([1-(4-cyanobenzyl)-1H-imidazol-5-yl]acetylamino)-3(S)-methylpentyl]-N-(1-naphthylmethyl)glycyl-2(RS) amino-3-(2 thienyl) propionic Acid Methyl Ester The title compound was prepared as the trifluoroacetate salt using the procedures described in Example 34 Step H using 2(RS) amino-3-(2 thienyl)propionic acid methyl ester hydrochloride.

$^1$H NMR (CD$_3$OD, 400 MHz) δ 8.81 (1H, m), 8.19 (1H, d, J=9.0 Hz), 8.00-7.80 (2H, m), 7.62 (2H, d, J=8.0 Hz), 7.50-7.30 (5H, m), 7.29 (2H, d, J=8.0 Hz), 7.036 (1H, m), 6.718 (1H, s), 6.61 (1H, m), 5.39 (2H, m), 4.60 (1H, m), 4.40 (1H, m), 3.98 (1H, m), 3.60 (3H, s), 3.60-3.30 (7H, m), 3.20-2.95 (3H, m), 1.47 (1H, m), 1.32 (1H, m), 1.08 (1H, m), 0.85 (6H, m) ppm. FAB HRMS exact mass calc'd for C$_{40}$H$_{45}$N$_6$O$_4$S 705.322301 (MH$^+$), found 705.321444. Anal. calc'd for C$_{40}$H$_{44}$N$_6$O$_4$S 0.35H$_2$O and 2.50TFA C, 54.25; H, 4.78 N, 8.44. Found: C, 54.27; H, 4.77; N, 8.36.

EXAMPLE 40

Preparation of N-[2(S)-([1-(4-cyanobenzyl)-1H-imidazol-5-yl]acetylamino)-3(S)-methylpentyl]-N-(1-naphthylmethyl)glycyl-2(RS)-amino-3-(2 thienyl) propionic Acid The title compound was prepared as the trifluoroacetate salt using the procedures described in Example 36 and the methyl ester prepared in Example 39.

FAB HRMS exact mass calc'd for C$_{39}$H$_{42}$N$_6$O$_4$S 691.306651 (MH$^+$), found 691.306950.

EXAMPLE 41

Preparation of N-[2(S)-([1-(4-cyanobenzyl)-1H-imidazol-5-yl]acetylamino)-3(S)-methylpentyl]-N-(1-naphthylmethyl)glycyl-2(S) amino-4-sulfamyl-butanoic Acid Methyl Ester The title compound was prepared as the trifluoroacetate salt using the procedures described in Example 34 Step H using 2(S) amino-4-sulfamyl-butanoic acid methyl ester hydrochloride.

¹H NMR (CD₃OD, 400 MHz) δ 8.87 (1H, m), 8.33 (1H, m), 8.00-7.80 (2H, m), 7.73 (2H, d, J=8.2 Hz), 7.70-7.40 (5H, m), 7.35 (2H, d, J=8.0 Hz), 5.42 (2H, m), 4.40 (1H, m), 4.10 (1H, m), 3.70 (3H, s), 3.60-3.20 (7H, m), 3.00 (3H, m), 2.30 (1H, m), 2.05 (1H, m), 1.55 (1H, m), 1.40 (1H, m), 1.15 (1H, m), 0.95 (6H, m) ppm. FAB HRMS exact mass calc'd for $C_{37}H_{46}N_7O_6S$ 716.323030 (MH⁺), found 716.323766. Anal. calc'd for $C_{37}H_{45}N_7O_6S$ 1.20H₂O and 3.00TFA C, 47.84; H, 4.71 N, 9.08. Found: C, 47.84; H, 4.58; N, 9.26.

EXAMPLE 42

Preparation of N-[2(S)-([1-(4-cyanobenzyl)-1H-imidazol-5-yl]acetylamino)-3(S)-methylpentyl]-N-(1-naphthylmethyl)glycyl-2(S) amino-4-sulfamyl-butanoic Acid The title compound was prepared as the trifluoroacetate salt using the methyl ester prepared in Example 41.

¹H NMR (CD₃OD, 400 MHz) δ 8.86 (1H, m), 8.26 (1H, m), 8.00-7.80 (2H, m), 7.73 (2H, d, J=8.2 Hz), 7.70-7.40 (5H, m), 7.35 (2H, d, J=8.0 Hz), 5.47 (2H, m), 4.42 (1H, m), 4.08 (1H, m), 3.60-3.20 (7H, m), 3.00 (3H, m), 2.30 (1H, m), 2.05 (1H, m), 1.57 (1H, m), 1.38 (1H, m), 1.15 (1H, m), 0.95 (6H, m) ppm. FAB HRMS exact mass calc'd for $C_{36}H_{44}N_7O_6S$ 702.307379 (MH⁺), found 702.308307. Anal. calc'd for $C_{36}H_{43}N_7O_6S$ 0.40H₂O and 2.65TFA C, 49.06; H, 4.63 N, 9.70. Found: C, 49.03; H, 4.63; N, 9.99.

EXAMPLE 43

Preparation of N-[2(S)-([1-(4-cyanobenzyl)-1H-imidazol-5-yl]acetylamino)-3(S)-methylpentyl]-N-(1-naphthylmethyl)glycyl-N-methyl Methionine Methyl Ester The title compound was prepared as the trifluroacetate salt using the procedures described in Example 34 Step H using N-methyl methionine methyl ester hydrochloride.

¹H NMR (CD₃OD, 400 MHz) δ 8.93 (1H, m), 8.34 (1H, m), 8.04 (1H, d, J=7.7 Hz), 7.98 (1H, m), 7.75 (3H, m), 7.60-7.20 (6H, m), 5.48 (2H, m), 5.06 (1H, m), 4.40 (1H, m), 4.10 (1H, m), 3.66 (3H, s), 3.80-3.20 (9H, m), 2.85 (3H, br s), 2.40-2.00 (1H, m), 2.05 (3H, s), 1.95 (1H, m), 1.57 (1H, m), 1.45 (1H, m), 1.10 (1H, m), 0.95 (6H, m) ppm. FAB HRMS exact mass calc'd for $C_{39}H_{49}N_6O_4S$ 697.353601 (MH⁺), found 697.353335. Anal. calc'd for $C_{39}H_{48}N_6O_4S$ 0.45H₂O and 2.95TFA C, 51.79; H, 5.02 N, 8.07. Found: C, 51.79; H, 4.99; N, 8.15.

EXAMPLE 44

Preparation of N-[2(S)-([1-(4-cyanobenzyl)-1H-imidazol-5-yl]acetylamino)-3(S)-methylpentyl]-N-(1-naphthylmethyl)glycyl-N-methyl Methionine The title compound was prepared as the trifluoroacetate salt using the procedures described in Example 36 and the methyl ester prepared in Example 43.

¹H NMR (CD₃OD, 400 MHz) δ 8.78 (0.7H, m), 8.76 (0.3H, m), 8.24 (1H, m), 8.0-7.00 (11H, m), 5.37 (2H, m), 5.00-3.00 (10H, m), 2.85 (3H, br s), 2.40-2.00 (4H, m), 1.93 (0.9H, s), 1.90 (2.1H, m), 1.50 (1H, m), 1.31 (1H, m), 1.08 (1H, m), 0.80 (6H, m) ppm. FAB HRMS exact mass calc'd for $C_{36}H_{47}N_6O_4S$ 683.337951 (MH⁺), found 683.337329. Anal. calc'd for $C_{36}H_{46}N_6O_4S$ 2.84TFA C, 52.11; H, 4.89 N, 8.35. Found: C, 51.74; H, 5.02; N, 8.74.

EXAMPLE 45

Preparation of N-[2(S)-([1-(4-cyanobenzyl)-1H-imidazol-5-yl]acetylamino)-3(S)-methylpentyl]-N-(1-naphthylmethyl)glycyl-homoserine Lactone The title compound was prepared as the trifluoroacetate salt using the procedures described in Example 34 Step H using homoserine lactone hydrochloride.

¹H NMR (CD₃OD, 400 MHz) δ 8.91 (1H, m), 8.30 (1H, m), 8.05-7.90 (2H, m), 7.74 (2H, d, J=8.4 Hz), 7.70 (1H, d, J=6.2 Hz), 7.60-7.50 (4H, m), 7.53 (2H, d, 8.0 Hz), 5.50 (2H, m), 4.70 (2H, m), 4.39 (1H, dd, J=10.9 and 8.9 Hz), 4.30 (1H, t, J=7.9 Hz), 4.21 (1H, m), 4.05 (2H, m), 4.00-3.40 (5H, m), 2.30 (1H, m), 1.90 (1H, m), 1.57 (1H, m), 1.43 (1H, m), 1.18 (1H, m), 0.98-0.90 (6H, m) ppm. FAB HRMS exact mass calc'd for $C_{36}H_{41}N_6O_4$ 621.318929 (MH⁺), found 621.317455. Anal. calc'd for $C_{39}H_{48}N_6O_4S$ 0.83H₂O and 3.76TFA C, 49.11; H, 4.30 N, 7.90. Found: C, 49.11; H, 4.30; N, 8.35.

EXAMPLE 46

Preparation of N-[2(S)-([1-(4-cyanobenzyl)-1H-imidazol-5-yl]acetylamino)-3(S)-methylpentyl]-N-(1-naphthylmethyl) glycyl-homoserine The title compound was prepared as the lithium salt using the procedures described in Example 36 and the lactone prepared in Example 45.

FAB HRMS exact mass calc'd for $C_{36}H_{43}N_6O_5$ 639.329494 (MH⁺), found 639.328919.

EXAMPLE 47

Preparation of N-[2(S)-([1-(4-cyanobenzyl)-1H-imidazol-5-yl]acetylamino)-3(S)-methylpentyl]-N-(1-naphthylmethyl)glycyl-proline Methyl Ester The title compound was prepared as the trifluoroacetate salt using the procedures described in Example 34 Step H using L-proline methyl ester hydrochloride.

¹H NMR (CD₃OD, 400 MHz) δ 8.80 (1H, s), 8.38-8.28 (1H, m), 8.02 (1H, d, J=8.4 Hz), 7.96 (1H, d, J=8.4 Hz), 7.80-7.65 (3H, m), 7.60-7.30 (6H, m), 5.55-5.40 (2H, m), 5.00 (1H, m), 4.40-4.00 (3H, m), 3.70 (3H, m), 3.70-3.00 (8H, m), 2.25-2.05 (1H, m), 2.00 (2H, m), 1.95-1.50 (2H, m), 1.40 (1H, m), 1.17 (1H, m), 1.00-0.80 (6H, m) ppm. FAB HRMS exact mass calc'd for $C_{38}H_{45}N_6O_4$ 649.350229 (MH⁺), found 649.350481. Anal. calc'd for $C_{38}H_{44}N_6O_4$ 1.75H₂O and 3.00TFA C, 51.69; H, 4.98 N, 8.22. Found: C, 51.69; H, 4.79; N, 8.58.

EXAMPLE 48

Preparation of N-[2(S)-([1-(4-cyanobenzyl)-1H-imidazol-5-yl]acetylamino)-3(S)-methylpentyl]-N-(1-naphthylmethyl)glycyl-proline The title compound was prepared as the trifluoroacetate salt using the procedures described in Example 36 and the methyl ester prepared in Example 47.

¹H NMR (CD₃OD, 400 MHz) δ 8.85 (0.8H, m), 8.80 (0.2H, m), 8.32 (1H, d, J=8.4 Hz), 8.04-7.90 (2H, m), 7.80-7.64 (3H, m), 7.60-7.28 (6H, m), 5.54-5.36 (2H, m), 4.40-4.00 (2H, m), 3.85-3.00 (10H, m), 2.20 (1H, m), 2.10-1.80 (3H, m), 1.57 (1H, m), 1.42 (1H, m), 1.17 (1H, m), 0.98-0.82 (6H, m) ppm. FAB HRMS exact mass calc'd for $C_{37}H_{43}N_6O_4$ 635.334579 (MH⁺), found 635.332994. Anal. calc'd for $C_{37}H_{42}N_6O_4$ 0.80H₂O and 2.80TFA C, 52.83; H, 4.83 N, 8.68. Found: C, 52.81; H, 4.81; N, 8.88.

EXAMPLE 49

Preparation of N-[2(S)-([1-(4-cyanobenzyl)-1H-imidazol-5-yl]acetylamino)-3(S)-methylpentyl]-N-(1-naphthylmethyl)glycyl-D-proline Methyl Ester The title compound was prepared as the trifluoroacetate salt using the procedures described in Example 34 Step H using D-proline methyl ester hydrochloride.

¹H NMR (CD₃OD, 400 MHz) δ 8.92 (0.3H, s), 8.88 (0.7H, s), 8.08-7.90 (2H, m), 7.85-7.30 (10H, m), 5.46 (2H, m), 5.00-4.40 (1H, m), 4.35 (1H, m), 4.10-4.00 (2H, m), 3.60 (3H, s), 3.80-3.20 (8H, m), 2.20 (1H, m), 2.00-1.80 (3H, m), 1.60 (1H, m), 1.45 (1H, m), 1.15 (1H, m), 1.00-0.80 (6H, m) ppm. FAB HRMS exact mass calc'd for $C_{38}H_{45}N_6O_4$ 649.350229 (MH⁺), found 649.351271. Anal. calc'd for $C_{38}H_{44}N_6O_4$ 2.20H₂O and 3.00TFA C, 51.28; H, 5.03 N, 8.16. Found: C, 51.27; H, 4.71 N, 8.39.

EXAMPLE 50

Preparation of N-[2(S)-([1-(4-cyanobenzyl)-1H-imidazol-5-yl]acetylamino)-3(S)-methylpentyl]-N-(1-naphthylmethyl)glycyl-proline The title compound was prepared as the trifluoroacetate salt using the procedures described in Example 36 and the methyl ester prepared in Example 49.

¹H NMR (CD₃OD, 400 MHz) δ 8.80-8.70 (1H, m), 8.30-8.15 (1H, m), 8.00-7.20 (11H, m), 5.40 (0.4H, s), 5.35 (1.6H, m), 5.00-4.60 (1H, m), 4.24 (1H, m), 3.97 (1H, m), 3.70-3.00 (10H, m), 2.20-2.00 (1H, m), 2.00-1.60 (2H, m), 1.50 (1H, m), 1.34 (1H, m), 1.08 (1H, m), 1.90-0.70 (6H, m) ppm. FAB HRMS exact mass calc'd for $C_{37}H_{43}N_6O_4$ 635.334579 (MH⁺), found 635.333794. Anal. calc'd for $C_{37}H_{42}N_6O_4$ 0.50H₂O and 2.55TFA C, 54.11 H, 4.91 N, 8.99. Found: C, 54.11; H, 4.93; N, 8.95.

EXAMPLE 51

Preparation of N-[2(S)-([1-(4-cyanobenzyl)-1H-imidazol-5-yl]acetylamino)-3(S)-methylpentyl]-N-(1-naphthylmethyl)glycyl-L-pipecolinic Acid The title compound was prepared as the trifluroacetate salt using the procedures described in Example 34 Step H using L-pipecolinic acid.

¹H NMR (CD₃OD, 400 MHz) δ 8.96-8.84 (1H, m), 8.36 (1H, m), 8.10-7.20 (11H, m), 5.45 (2H, m), 5.20-4.40 (1H, m), 4.40-4.00 (3H, m), 4.00-3.00 (9H, m), 2.20 (2H, m), 1.80-1.05 (6H, m), 1.00-0.80 (6H, m) ppm. FAB HRMS exact mass calc'd for $C_{38}H_{45}N_6O_4$ 649.350229 (MH⁺), found 649.352801. Anal. calc'd for $C_{38}H_{44}N_6O_4$ 2.75TFA C, 54.29; H, 4.90N, 8.73. Found: C, 54.22; H, 4.88 N, 8.89.

EXAMPLE 52

Preparation of N-[2(S)-([1-(4-carbomethoxybenzyl)-1H-imidazol-5-yl]acetylamino)-3(S)-methylpentyl]-N-(1-naphthylmethyl)glycyl-methionine Methyl Ester The title compound—as the trifluoroacetate salt—was isolated as a minor component of the reaction mixture prepared in Example 9 Step A.

¹H NMR (CD₃OD, 400 MHz) δ 8.93 (1H, s), 8.30 (1H, m), 8.05-7.35 (9H, m), 7.31 (2H, d, J=8.2 Hz), 5.48 (2H, m), 5.00-4.40 (1H, m), 4.39 (1H, s), 4.05 (1H, m), 3.90 (3H, m), 4.00-3.30 (7H, m), 3.67 (3H, m), 3.17 (1H, m), 2.20-2.10 (2H, m), 1.98 (3H, s), 1.75 (1H, m), 1.55 (1H, m), 1.40 (1H, m), 1.18 (1H, m), 1.00-0.80 (6H, m) ppm. Anal. calc'd for $C_{39}H_{49}N_5O_6S$ 0.15H₂O, 2.15TFA C, 53.96; H, 5.38; N, 7.27. Found: C, 53.96; H, 5.39 N, 7.59.

EXAMPLE 53

Preparation of N-[2(S)-([1-(4-carbomethoxybenzyl)-1H-imidazol-5-yl]acetylamino)-3(S)-methylpentyl]-N-(1-naphthylmethyl)glycyl-methionine The title compound was prepared as the trifluoroacetate salt using the procedures described in Example 36 and the methyl ester prepared in Example 52.

¹H NMR (CD₃OD, 400 MHz) δ 8.80 (1H, m), 8.20 (1H, m), 8.00-7.20 (11H, m), 5.40 (2H, m), 5.00-4.60 (1H, m), 4.32 (1H, m), 4.05 (1H, m), 3.80 (3H, s), 3.70-3.00 (7H, m), 2.40-2.00 (3H, m), 1.88 (3H, s), 1.75 (1H, m), 1.55 (1H, m), 1.30 (1H, m), 1.05 (1H, m), 1.00-0.65 (6H, m) ppm. Anal. calc'd for $C_{38}H_{47}N_5O_6S$ 0.15H₂O and 2.85TFA C, 50.98 H, 4.91 N, 6.80. Found: C, 50.98; H, 4.89; N, 7.19.

EXAMPLE 54

Preparation of 1-(2-naphthylmethyl)-1H-imidazol-5-ylacetyl-isoleucinyl-phenylalaninyl-methionine Methyl Ester The title compound was prepared as the trifluoroacetate salt using the procedures described in Example 34 Step H and isoleucinyl-phenylalaninyl-methionine methyl ester hydrochloride.

¹H NMR (CD₃OD, 400 MHz) δ 8.89 (1H, s), 8.39 (1H, d, J=8.0 Hz), 8.19 (2H, m), 8.00-7.90 (3H, m), 7.67 (1H, s), 7.60-7.52 (2H, m), 7.48 (1H, s), 7.36 (1H, d, J=8.0 Hz), 7.30-7.10 (5H, m), 5.56 (1H, d, J=15.0 Hz), 5.49 (1H, dJ=15.0 Hz), 4.69 (1H, m), 4.52 (1H, m), 4.20-4.14 (1H, m), 3.54 (1H, d, J=18.0 Hz), 3.66 (1H, d, J=18.0 Hz), 3.66 (3H, s), 3.14 (1H, dd, J=15.0 and 6.0 Hz), 2.91 (1H, dd, J=15.0 and 9.0 Hz), 2.56-2.16 (2H, m), 2.06 (1H, m), 2.04 (3H, s), 1.89 (1H, m), 1.73 (1H, m), 1.40 (1H, m), 1.08 (1H, m), 0.90-0.80 (6H, m) ppm. FAB HRMS exact mass calc'd for $C_{37}H_{46}N_5O_5S$ 672.321967 (MH⁺), found 672.321794. Anal. calc'd for $C_{37}H_{45}N_5O_5S$ 0.10H₂O and 2.30TFA C, 57.87; H, 5.70 N, 8.52. Found: C, 57.88; H, 5.61 N, 8.49.

EXAMPLE 55

Preparation of 1-(2-naphthylmethyl)-1H-imidazol-5-ylacetyl-isoleucinyl-phenylalaninyl-methionine The title compound was prepared as the trifluoroacetate salt using the procedures described in Example 36 and the methyl ester prepared in Example 54.

¹H NMR (CD₃OD, 400 MHz) δ 8.80 (1H, s), 8.15 (1H, d, J=8.0 Hz), 7.93 (1H, d, J=8.0 Hz), 7.89 (2H, m), 7.74 (1H, m), 7.58-7.52 (2H, m), 7.44 (1H, s), 7.35 (1H, dd, J=10.0 and 3 Hz), 7.30-7.10 (5H, m), 5.54 (1H, d, J=15.0 Hz), 5.47 (1H, d, J=15.0 Hz), 4.70 (1H, m), 4.50 (1H, m), 4.15 (1H, m), 3.51 (1H, d, J=17.0 Hz), 3.66 (1H, d, J=17.0 Hz), 3.18 (1H, dd, J=15.0 and 6.0 Hz), 2.92 (1H, dd, J=15.0 and 9.0 Hz), 2.56-2.40 (2H, m), 2.10 (1H, m), 2.05 (3H, s), 1.92 (1H, m), 1.73 (1H, m), 1.40 (1H, m), 1.08 (1H, m), 0.90-0.80 (6H, m) ppm. FAB HRMS exact mass calc'd for $C_{36}H_{44}N_5O_5S$ 658.305448 (MH⁺), found 658.3063 17.

EXAMPLE 56

In Vitro Inhibition of Ras Farnesyl Transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl₂, 5 mM dithiothreitol (DTT), 100 mM [³H]-farnesyl diphosphate ([³H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol.

Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <10 μM.

EXAMPLE 57

In Vivo Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000× g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 58

In Vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures were seeded and comparisons are made.

What is claimed is:

1. A compound which inhibits Ras farnesyl-transferase having the formula I:

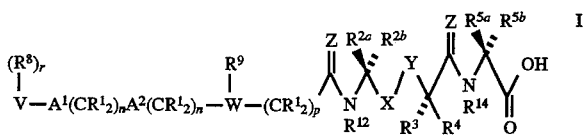

wherein:

R$^1$ is independently selected from:
a) hydrogen,
b) aryl, heterocyclic, cycloalkyl, alkenyl, alkynyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
c) C$_1$–C$_6$ alkyl, and
d) C$_1$–C$_6$ alkyl substituted with a group selected from: aryl, heterocyclic, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{2a}$ and R$^{2b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) a group selected from C$_1$–C$_{20}$ alkyl, C$_2$–C$_{20}$ alkenyl, C$_3$–C$_{10}$ cycloalkyl, aryl or heterocyclic group, the group which is substituted with a substituent selected from F, Cl, Br, NO$_2$, R$^{10}$O—, R$^{11}$S(O)$_m$—, R$^{10}$C(O) NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl,
d) a group selected from C$_1$–C$_{20}$ alkyl, C$_2$–C$_{20}$ alkenyl, C$_3$–C$_{10}$ cycloalkyl, aryl or heterocyclic group, and
e) C$_1$–C$_6$ alkyl substituted with a group selected from:
  i) aryl,
  ii) substituted aryl,
  iii) heterocyclic,
  iv) substituted heterocyclic,
  v) C$_3$–C$_{10}$ cycloalkyl, and
  vi) substituted C$_3$–C$_{10}$ cycloalkyl;

or

R$^{2a}$ and R$^{2b}$ are combined to form —(CH$_2$)$_s$—;

R$^3$ and R$^4$ are independently selected from:
a) a side chain of a naturally occurring amino acid,
b) an oxidized form of a side chain of a naturally occurring amino acid which is:
  i) methionine sulfoxide, or
  ii) methionine sulfone, c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, d) a group selected from $C_1$–$C_{20}$ alkyl, $C_2$–$C_{20}$ alkenyl, $C_3$–$C_{10}$ cycloalkyl, aryl or heterocyclic group, and e) $C_1$–$C_6$ alkyl substituted with a group selected from:
   i) aryl,
   ii) substituted aryl,
   iii) heterocyclic,
   iv) substituted heterocyclic,
   v) $C_3$–$C_{10}$ cycloalkyl, and
   vi) substituted $C_3$–$C_{10}$ cycloalkyl;

or $R^3$ and $R^4$ are combined to form —$(CH_2)_s$—;

$R^{5a}$ and $R^{5b}$ are independently selected from:
   a) a side chain of a naturally occurring amino acid,
   b) an oxidized form of a side chain of a naturally occurring amino acid which is:
      i) methionine sulfoxide, or
      ii) methionine sulfone,
   c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
   d) a group selected from $C_1$–$C_{20}$ alkyl, $C_2$–$C_{20}$ alkenyl, $C_3$–$C_{10}$ cycloalkyl, aryl or heterocyclic group, and
   e) $C_1$–$C_6$ alkyl substituted with a group selected from:
      i) aryl,
      ii) substituted aryl,
      iii) heterocyclic,
      iv) substituted heterocyclic,
      v) $C_3$–$C_{10}$ cycloalkyl, and
      vi) substituted $C_3$–$C_{10}$ cycloalkyl;

or $R^{5a}$ and $R^{5b}$ are combined to form —$(CH_2)_s$— or —$(CH_2)_s$— wherein one of the carbon atoms is replaced by a moiety selected from: O, $S(O)_m$, —NC(O)—, and —N($COR^{10}$)—; or $R^{5a}$ or $R^{5b}$ are combined with $R^{14}$ to form a ring such that

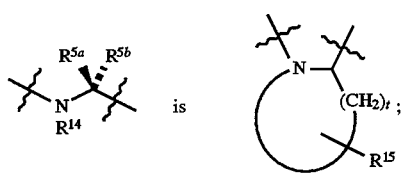

X-Y is a) 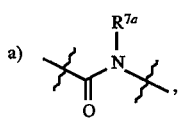

-continued

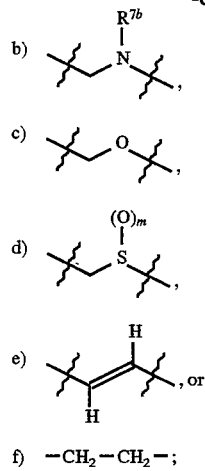

f) —$CH_2$—$CH_2$—;

$R^{7a}$ is selected from
   a) hydrogen,
   b) aryl,
   c) substituted aryl,
   d) heterocyclic,
   e) substituted heterocyclic,
   f) cycloalkyl,
   g) substituted cycloalkyl,
   h) $C_1$–$C_6$ alkyl, and
   i) $C_1$–$C_6$ alkyl substituted with a group selected from aryl, substituted aryl, heterocyclic, substituted heterocyclic, cycloalkyl and substituted cycloalkyl;

$R^{7b}$ is selected from
   a) hydrogen,
   b) aryl,
   c) substituted aryl,
   d) heterocyclic,
   e) substituted heterocyclic,
   f) cycloalkyl,
   g) substituted cycloalkyl,
   h) $C_1$–$C_6$ alkyl,
   i) $C_1$–$C_6$ alkyl substituted with a group selected from aryl, substituted aryl, heterocyclic, substituted heterocyclic, cycloalkyl and substituted cycloalkyl,
   j) a carbonyl group which is bonded to a group selected from aryl, substituted aryl, heterocyclic, substituted heterocyclic, cycloalkyl and substituted cycloalkyl,
   k) a carbonyl group which is bonded to a $C_1$–$C_6$ alkyl substituted with hydrogen or an unsubstituted or substituted group selected from aryl, heterocyclic and cycloalkyl,
   l) a carbonyl group which is bonded to a $C_1$–$C_6$ alkyl substituted with a group selected from aryl, substituted aryl, heterocyclic, substituted heterocyclic, cycloalkyl and substituted cycloalkyl,
   m) a sulfonyl group which is bonded to a group selected from aryl, substituted aryl, heterocyclic, substituted heterocyclic, cycloalkyl and substituted cycloalkyl,
   n) a sulfonyl group which is bonded to a $C_1$–$C_6$ alkyl substituted with hydrogen or an unsubstituted or substituted group selected from aryl, heterocyclic and cycloalkyl, and
   p) a sulfonyl group which is bonded to a $C_1$–$C_6$ alkyl substituted with a group selected from aryl, substituted aryl, heterocyclic, substituted heterocyclic, cycloalkyl and substituted cycloalkyl, $R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted with a group selected from aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted with a group selected from perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen, $C_1$–$C_6$ alkyl and benzyl;

$R^{15}$ is independently selected from hydrogen and $C_1$–$C_6$ alkyl;

$A^1$ and $A^2$ are independently selected from: a bond, —CH=CH—, —C≡C—, O, —$N(R^{10})$—, —C(O)—, —C(O)$NR^{10}$—, —$NR^{10}C(O)$—, —$S(O)_2N(R^{10})$—, —$N(R^{10})S(O)_2$— or $S(O)_m$;

V is selected from:
a) hydrogen,
b) heterocycle,
c) aryl,
d) $C_1$–$C_{20}$ alkyl wherein from 0 to 4 non-terminal carbon atoms are replaced with a heteroatom selected from O, S, and N, and
e) $C_2$–$C_{20}$ alkenyl;
provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5; and t is 3, 4 or 5;

or a pharmaceutically acceptable salt thereof.

2. A compound which inhibits Ras farnesyl-transferase having the formula II:

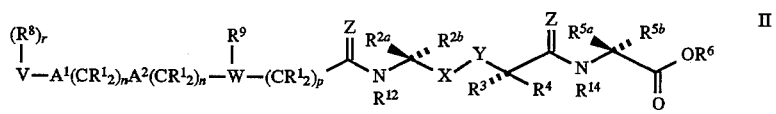

wherein:
$R^1$ is independently selected from:
a) hydrogen,
b) aryl, heterocyclic, cycloalkyl, alkenyl, alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted with a group selected from: aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
a) a side chain of a naturally occurring amino acid,
b) an oxidized form of a side chain of a naturally occurring amino acid which is:
i) methionine sulfoxide, or
ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
i) aryl,
ii) substituted aryl,
iii) heterocyclic,
iv) substituted heterocyclic,
v) $C_3$–$C_{10}$ cycloalkyl, and
vi) substituted $C_3$–$C_{10}$ cycloalkyl;

or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
i) aryl,
ii) substituted aryl, iii) heterocyclic,
iv) substituted heterocyclic,
v) $C_3-C_{10}$ cycloalkyl, and
vi) substituted $C_3-C_{10}$ cycloalkyl;

or $R^3$ and $R^4$ are combined to form —$(CH_2)_s$—;

$R^{5a}$ and $R^{5b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) a group selected from $C_1-C_{20}$ alkyl, $C_2-C_{20}$ alkenyl, $C_3-C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1-C_{20}$ alkyl,
d) a group selected from $C_1-C_{20}$ alkyl, $C_2-C_{20}$ alkenyl, $C_3-C_{10}$ cycloalkyl, aryl or heterocyclic group, and
e) $C_1-C_6$ alkyl substituted with a group selected from:
  i) aryl,
  ii) substituted aryl,
  iii) heterocyclic,
  iv) substituted heterocyclic,
  v) $C_3-C_{10}$ cycloalkyl, and
  vi) substituted $C_3-C_{10}$ cycloalkyl;

or $R^{5a}$ and $R^{5b}$ are combined to form —$(CH_2)_s$— or —$(CH_2)_s$— wherein one of the carbon atoms is replaced by a moiety selected from: O, $S(O)_m$, —NC(O)—, and —$N(COR^{10})$—; or $R^{5a}$ or $R^{5b}$ are combined with $R^{14}$ to form a ring such that

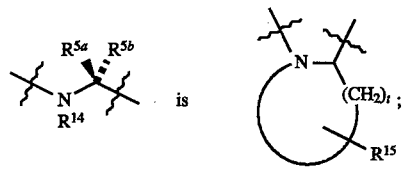

$R^6$ is
a) $C_1-C_8$ alkyl,
b) $C_1-C_8$ alkyl substituted with a group selected from:
  1) aryl,
  2) heterocycle,
  3) —$N(R^{11})_2$,
  4) —$OR^{10}$, or c) 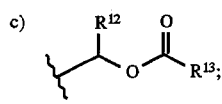

X-Y is a) 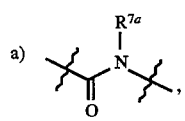

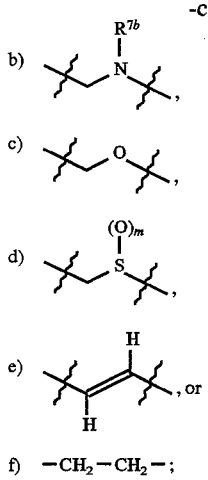

f) —$CH_2$—$CH_2$—;

$R^{7a}$ is selected from
a) hydrogen,
b) aryl,
c) substituted aryl,
d) heterocyclic,
e) substituted heterocyclic,
f) cycloalkyl,
g) substituted cycloalkyl,
h) $C_1-C_6$ alkyl, and
i) $C_1-C_6$ alkyl substituted with a group selected from aryl, substituted aryl, heterocyclic, substituted heterocyclic, cycloalkyl and substituted cycloalkyl;

$R^{7b}$ is selected from
a) hydrogen,
b) aryl,
c) substituted aryl,
d) heterocyclic,
e) substituted heterocyclic,
f) cycloalkyl,
g) substituted cycloalkyl,
h) $C_1-C_6$ alkyl,
i) $C_1-C_6$ alkyl substituted with a group selected from aryl, substituted aryl, heterocyclic, substituted heterocyclic, cycloalkyl and substituted cycloalkyl,
j) a carbonyl group which is bonded to a group selected from aryl, substituted aryl, heterocyclic, substituted heterocyclic, cycloalkyl and substituted cycloalkyl,
k) a carbonyl group which is bonded to a $C_1-C_6$ alkyl substituted with hydrogen or an unsubstituted or substituted group selected from aryl, heterocyclic and cycloalkyl,
l) a carbonyl group which is bonded to a $C_1-C_6$ alkyl substituted with a group selected from aryl, substituted aryl, heterocyclic, substituted heterocyclic, cycloalkyl and substituted cycloalkyl,
m) a sulfonyl group which is bonded to a group selected from aryl, substituted aryl, heterocyclic, substituted heterocyclic, cycloalkyl and substituted cycloalkyl,
n) a sulfonyl group which is bonded to a $C_1-C_6$ alkyl substituted with hydrogen or an unsubstituted or substituted group selected from aryl, heterocyclic and cycloalkyl, and
p) a sulfonyl group which is bonded to a $C_1-C_6$ alkyl substituted with a group selected from aryl, substituted aryl, heterocyclic, substituted heterocyclic, cycloalkyl and substituted cycloalkyl, $R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, NO$_2$, $R^{10}{}_2N$—C(NR$^{10}$)—, $R^{10}C(O)$—, $R^{10}OC(O)$—, N$_3$, —N(R$^{10}$)$_2$, or $R^{11}OC(O)NR^{10}$—,
c) $C_1$–$C_6$ alkyl, and
d) $C_1$–$C_6$ alkyl substituted with a group selected from: aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, H$_2$N—C(NH)—, $R^{10}C(O)$—, $R^{10}OC(O)$—, N$_3$, —N(R$^{10}$)$_2$, or $R^{11}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, NO$_2$, (R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—,
c) $C_1$–$C_6$ alkyl, and
d) $C_1$–$C_6$ alkyl substituted with a group selected from: perfluoroalkyl, F, Cl, Br, $R^{10}O$—, $R^{11}S(O)_m$—, $R^{10}C(O)NR^{10}$—, CN, (R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{13}$ is independently selected from $C_1$–$C_6$ alkyl;

$R^{14}$ is independently selected from hydrogen, $C_1$–$C_6$ alkyl and benzyl;

$R^{15}$ is independently selected from hydrogen and $C_1$–$C_6$ alkyl;

$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
a) hydrogen,
b) heterocycle,
c) aryl,
d) $C_1$–$C_{20}$ alkyl wherein from 0 to 4 non-terminal carbon atoms are replaced with a heteroatom selected from O, S, and N, and
e) $C_2$–$C_{20}$ alkenyl;
provided that V is not hydrogen if $A^1$ is S(O)$_m$ and V is not hydrogen if $A^1$ is a bond, n is 0 and $A^2$ is S(O)$_m$ or a bond;

W is a heterocycle;
Z is independently H$_2$ or O;
m is 0, 1 or 2;
n is 0, 1, 2, 3 or 4;
p is 0, 1, 2, 3 or 4;
r is 0 to 5, provided that r is 0 when V is hydrogen;

s is 4 or 5; and
t is 3, 4 or 5;
or a pharmaceutically acceptable salt thereof.

3. A compound which inhibits Ras farnesyl-transferase having the formula III:

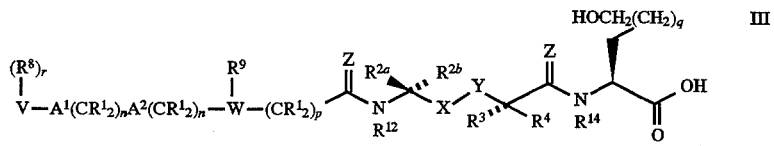

wherein:
$R^1$ is independently selected from:
a) hydrogen,
b) aryl, heterocyclic, cycloalkyl, alkenyl, alkynyl, $R^{10}O$—, $R^{11}S(O)_m$—, $R^{10}C(O)NR^{10}$—, CN, NO$_2$, (R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—,
c) $C_1$–$C_6$ alkyl, and
d) $C_1$–$C_6$ alkyl substituted with a group selected from: aryl, heterocyclic, cycloalkyl, alkenyl, alkynyl, $R^{10}O$—, $R^{11}S(O)_m$—, $R^{10}C(O)NR^{10}$—, CN, (R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—;

$R^{2a}$ and $R^{2b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, NO$_2$, $R^{10}O$—, $R^{11}S(O)_m$—, $R^{10}C(O)NR^{10}$—, CN, (R$^{10}$)$_2$N—C(NR$^{10}$)—, $R^{10}C(O)$—, $R^{10}OC(O)$—, N$_3$, —N(R$^{10}$)$_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;
or
$R^{2a}$ and $R^{2b}$ are combined to form —(CH$_2$)$_s$—;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, NO$_2$, $R^{10}O$—, $R^{11}S(O)_m$—, $R^{10}C(O)NR^{10}$—, CN, (R$^{10}$)$_2$N—C(NR$^{10}$)—, $R^{10}C(O)$—, $R^{10}OC(O)$—, N$_3$, —N(R$^{10}$)$_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:

i) aryl,
ii) substituted aryl,
iii) heterocyclic,
iv) substituted heterocyclic,
v) $C_3$–$C_{10}$ cycloalkyl, and
vi) substituted $C_3$–$C_{10}$ cycloalkyl;

or $R^3$ and $R^4$ are combined to form —$(CH_2)_s$—;

X-Y is

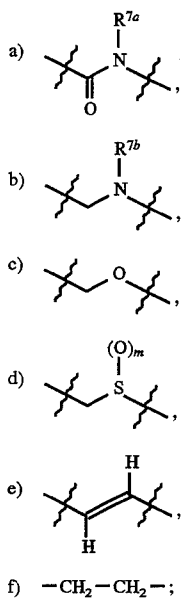

f) —$CH_2$—$CH_2$—;

$R^{7a}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl, and
i) $C_1$–$C_6$ alkyl substituted with a group selected from aryl, substituted aryl, heterocyclic, substituted heterocyclic, cycloalkyl and substituted cycloalkyl;

$R^{7b}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl,
i) $C_1$–$C_6$ alkyl substituted with a group selected from aryl, substituted aryl, heterocyclic, substituted heterocyclic, cycloalkyl and substituted cycloalkyl,
j) a carbonyl group which is bonded to a group selected from aryl, substituted aryl, heterocyclic, substituted heterocyclic, cycloalkyl and substituted cycloalkyl,
k) a carbonyl group which is bonded to a $C_1$–$C_6$ alkyl substituted with hydrogen or an unsubstituted or substituted group selected from aryl, heterocyclic and cycloalkyl,
l) a carbonyl group which is bonded to a $C_1$–$C_6$ alkyl substituted with a group selected from aryl, substituted aryl, heterocyclic, substituted heterocyclic, cycloalkyl and substituted cycloalkyl,
m) a sulfonyl group which is bonded to a group selected from aryl, substituted aryl, heterocyclic, substituted heterocyclic, cycloalkyl and substituted cycloalkyl,
n) a sulfonyl group which is bonded to a $C_1$–$C_6$ alkyl substituted with hydrogen or an unsubstituted or substituted group selected from aryl, heterocyclic and cycloalkyl, and
p) a sulfonyl group which is bonded to a $C_1$–$C_6$ alkyl substituted with a group selected from aryl, substituted aryl, heterocyclic, substituted heterocyclic, cycloalkyl and substituted cycloalkyl, $R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted with a group selected from: aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted with a group selected from: perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen, $C_1$–$C_6$ alkyl and benzyl;

$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
a) hydrogen,
b) heterocycle,
c) aryl,
d) $C_1$–$C_{20}$ alkyl wherein from 0 to 4 non-terminal carbon atoms are replaced with a heteroatom selected from O, S, and N, and
e) $C_2$–$C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen; and
s is 4 or 5;
or a pharmaceutically acceptable salt thereof.

4. A compound which inhibits Ras farnesyl-transferase having the formula IV:

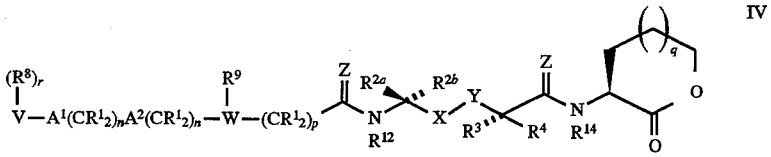

wherein:

$R^1$ is independently selected from:
  a) hydrogen,
  b) aryl, heterocyclic, cycloalkyl, alkenyl, alkynyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$,
  c) $C_1–C_6$ alkyl, and
  d) $C_1–C_6$ alkyl substituted with a group selected from: aryl, heterocyclic, cycloalkyl, alkenyl, alkynyl, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)NR^{10}—$;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) a group selected from $C_1–C_{20}$ alkyl, $C_2–C_{20}$ alkenyl, $C_3–C_{10}$ cycloalkyl, aryl or heterocyclic group, the group which is substituted with a substituent selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1–C_{20}$ alkyl,
  d) a group selected from $C_1–C_{20}$ alkyl, $C_2–C_{20}$ alkenyl, $C_3–C_{10}$ cycloalkyl, aryl or heterocyclic group, and
  e) $C_1–C_6$ alkyl substituted with a group selected from:
    i) aryl,
    ii) substituted aryl,
    iii) heterocyclic,
    iv) substituted heterocyclic,
    v) $C_3–C_{10}$ cycloalkyl, and
    vi) substituted $C_3–C_{10}$ cycloalkyl;
or
$R^{2a}$ and $R^{2b}$ are combined to form $—(CH_2)_s—$;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) a group selected from $C_1–C_{20}$ alkyl, $C_2–C_{20}$ alkenyl, $C_3–C_{10}$ cycloalkyl, aryl or heterocyclic group, the group which is substituted with a substituent selected from F, Cl, Br, $NO_2$, $R^{10}O—$, $R^{11}S(O)_m—$, $R^{10}C(O)$ $NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1–C_{20}$ alkyl,
  d) a group selected from $C_1–C_{20}$ alkyl, $C_2–C_{20}$ alkenyl, $C_3–C_{10}$ cycloalkyl, aryl or heterocyclic group, and
  e) $C_1–C_6$ alkyl substituted with a group selected from:
    i) aryl,
    ii) substituted aryl,
    iii) heterocyclic,
    iv) substituted heterocyclic,
    v) $C_3–C_{10}$ cycloalkyl, and
    vi) substituted $C_3–C_{10}$ cycloalkyl;
or
$R^3$ and $R^4$ are combined to form $—(CH_2)_s—$;

X-Y is

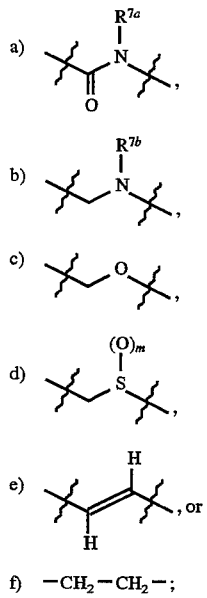

f) $—CH_2—CH_2—$;

$R^{7a}$ is selected from
  a) hydrogen,
  b) aryl,
  c) substituted aryl,
  d) heterocyclic,
  e) substituted heterocyclic,
  f) cycloalkyl,
  g) substituted cycloalkyl,
  h) $C_1–C_6$ alkyl, and
  i) $C_1–C_6$ alkyl substituted with a group selected from aryl, substituted aryl, heterocyclic, substituted heterocyclic, cycloalkyl and substituted cycloalkyl;

$R^{7b}$ is selected from
  a) hydrogen,
  b) aryl,
  c) substituted aryl,
  d) heterocyclic,
  e) substituted heterocyclic,
  f) cycloalkyl,
  g) substituted cycloalkyl,
  h) $C_1–C_6$ alkyl,
  i) $C_1–C_6$ alkyl substituted with a group selected from aryl, substituted aryl, heterocyclic, substituted heterocyclic, cycloalkyl and substituted cycloalkyl, j) a carbonyl group which is bonded to a group selected from aryl, substituted aryl, heterocyclic, substituted heterocyclic, cycloalkyl and substituted cycloalkyl, k) a carbonyl group which is bonded to a $C_1$–$C_6$ alkyl substituted with hydrogen or an unsubstituted or substituted group selected from aryl, heterocyclic and cycloalkyl, l) a carbonyl group which is bonded to a $C_1$–$C_6$ alkyl substituted with a group selected from aryl, substituted aryl, heterocyclic, substituted heterocyclic, cycloalkyl and substituted cycloalkyl, m) a sulfonyl group which is bonded to a group selected from aryl, substituted aryl, heterocyclic, substituted heterocyclic, cycloalkyl and substituted cycloalkyl, n) a sulfonyl group which is bonded to a $C_1$–$C_6$ alkyl substituted with hydrogen or an unsubstituted or substituted group selected from aryl, heterocyclic and cycloalkyl, and p) a sulfonyl group which is bonded to a $C_1$–$C_6$ alkyl substituted with a group selected from aryl, substituted aryl, heterocyclic, substituted heterocyclic, cycloalkyl and substituted cycloalkyl, $R^8$ is independently selected from:
 a) hydrogen,
 b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—,
 c) $C_1$–$C_6$ alkyl, and
 d) $C_1$–$C_6$ alkyl substituted with a group selected from: aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
 a) hydrogen,
 b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
 c) $C_1$–$C_6$ alkyl, and
 d) $C_1$–$C_6$ alkyl substituted with a group selected from: perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen, $C_1$–$C_6$ alkyl and benzyl;

$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
 a) hydrogen,
 b) heterocycle,
 c) aryl,
 d) $C_1$–$C_{20}$ alkyl wherein from 0 to 4 non-terminal carbon atoms are replaced with a heteroatom selected from O, S, and N, and
 e) $C_2$–$C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen; and s is 4 or 5;

or a pharmaceutically acceptable salt thereof.

5. The compound according to claim 1 having the formula I:

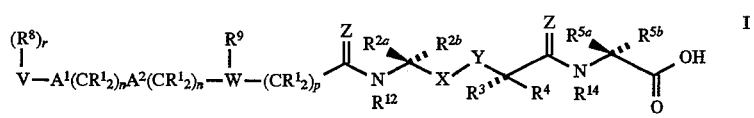

wherein:

$R^1$ is independently selected from:
 a) hydrogen,
 b) aryl, heterocyclic, cycloalkyl, $R^{10}O$—, —$N(R^{10})_2$ or alkenyl,
 c) $C_1$–$C_6$ alkyl, and
 d) $C_1$–$C_6$ alkyl substituted with a group selected from: aryl, heterocyclic, cycloalkyl, alkenyl, $R^{10}O$—, or —$N(R^{10})_2$;

$R^{2a}$ is selected from:
 a) a side chain of a naturally occurring amino acid, wherein the amino acid is selected from alanine, leucine, isoleucine and valine;
 b) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
 c) a group selected from $C_1$–$C_{20}$ alkyl, $C_2$–$C_{20}$ alkenyl, $C_3$–$C_{10}$ cycloalkyl, aryl or heterocyclic group, and
 d) $C_1$–$C_6$ alkyl substituted with a group selected from:
  i) aryl,
  ii) substituted aryl,
  iii) heterocyclic,
  iv) substituted heterocyclic,
  v) $C_3$–$C_{10}$ cycloalkyl, and vi) substituted $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
     i) methionine sulfoxide, or
     ii) methionine sulfone,
  c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
  d) a group selected from $C_1$–$C_{20}$ alkyl, $C_2$–$C_{20}$ alkenyl, $C_3$–$C_{10}$ cycloalkyl, aryl or heterocyclic group, and
  e) $C_1$–$C_6$ alkyl substituted with a group selected from:
     i) aryl,
     ii) substituted aryl,
     iii) heterocyclic,
     iv) substituted heterocyclic,
     v) $C_3$–$C_{10}$ cycloalkyl, and
     vi) substituted $C_3$–$C_{10}$ cycloalkyl;

$R^{5a}$ is selected from:
  a) a side chain of a naturally occurring amino acid, wherein the amino acid is selected from methionine and glutamine,
  b) an oxidized form of a side chain of a naturally occurring amino acid which is:
     i) methionine sulfoxide, or
     ii) methionine sulfone, and
  c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
  d) a group selected from $C_1$–$C_{20}$ alkyl, $C_2$–$C_{20}$ alkenyl, $C_3$–$C_{10}$ cycloalkyl, aryl or heterocyclic group, and
  e) $C_1$–$C_6$ alkyl substituted with a group selected from:
     i) aryl,
     ii) substituted aryl,
     iii) heterocyclic,
     iv) substituted heterocyclic,
     v) $C_3$–$C_{10}$ cycloalkyl, and
     vi) substituted $C_3$–$C_{10}$ cycloalkyl;

$R^{5b}$ is selected from:
  a) hydrogen, and
  b) $C_1$–$C_3$ alkyl; or $R^{5a}$ or $R^{5b}$ are combined with $R^{14}$ to form a ring such that

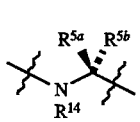 is 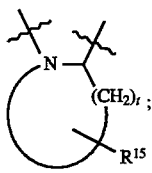

X-Y is

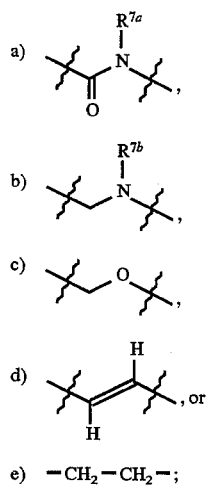

e) —$CH_2$—$CH_2$—;

$R^{7a}$ is selected from
  a) hydrogen,
  b) aryl,
  c) substituted aryl,
  d) heterocyclic,
  e) substituted heterocyclic,
  f) cycloalkyl,
  g) substituted cycloalkyl,
  h) $C_1$–$C_6$ alkyl, and
  i) $C_1$–$C_6$ alkyl substituted with a group selected from aryl, substituted aryl, heterocyclic, substituted heterocyclic, cycloalkyl and substituted cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
  a) hydrogen,
  b) aryl,
  c) substituted aryl,
  d) heterocyclic,
  e) substituted heterocyclic,
  f) cycloalkyl,
  g) substituted cycloalkyl,
  h) $C_1$–$C_6$ alkyl,
  i) $C_1$–$C_6$ alkyl substituted with a group selected from aryl, substituted aryl, heterocyclic, substituted heterocyclic, cycloalkyl and substituted cycloalkyl,
  j) a carbonyl group which is bonded to a group selected from aryl, substituted aryl, heterocyclic, substituted heterocyclic, cycloalkyl and substituted cycloalkyl,
  k) a carbonyl group which is bonded to a $C_1$–$C_6$ alkyl substituted with hydrogen or an unsubstituted or substituted group selected from aryl, heterocyclic and cycloalkyl,
  l) a carbonyl group which is bonded to a $C_1$–$C_6$ alkyl substituted with a group selected from aryl, substituted aryl, heterocyclic, substituted heterocyclic, cycloalkyl and substituted cycloalkyl,
  m) a sulfonyl group which is bonded to a group selected from aryl, substituted aryl, heterocyclic, substituted heterocyclic, cycloalkyl and substituted cycloalkyl,
  n) a sulfonyl group which is bonded to a $C_1$–$C_6$ alkyl substituted with hydrogen or an unsubstituted or substituted group selected from aryl, heterocyclic and cycloalkyl, and
  p) a sulfonyl group which is bonded to a $C_1$–$C_6$ alkyl substituted with a group selected from aryl, substituted aryl, heterocyclic, substituted heterocyclic, cycloalkyl and substituted cycloalkyl, wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted with a group selected from: $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) $C_1$–$C_6$ alkyl, and
d) $C_1$–$C_6$ alkyl substituted with a group selected from: $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen and $C_1$–$C_6$ alkyl;

$R^{15}$ is independently selected from hydrogen and $C_1$–$C_6$ alkyl;

$A^1$ and $A^2$ are independently selected from: a bond, —CH=CH—, —C≡C—, —C(O)—, —C(O)NR^{10}—, O, —N(R^{10})—, —NR^{10}C(O)—, —S(O)_2N(R^{10})—, —N(R^{10})S(O)_2— or $S(O)_m$;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl,
b) aryl,
c) $C_1$–$C_{20}$ alkyl wherein from 0 to 4 non-terminal carbon atoms are replaced with a heteroatom selected from O, S, and N, and
d) $C_2$–$C_{20}$ alkenyl;
provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;
n is 0, 1, 2, 3 or 4;
p is 0, 1, 2, 3 or 4;
r is 0 to 2;
s is 4 or 5; and
t is 3, 4 or 5;

or a pharmaceutically acceptable salt thereof.

6. The compound according to claim 2 having the formula II:

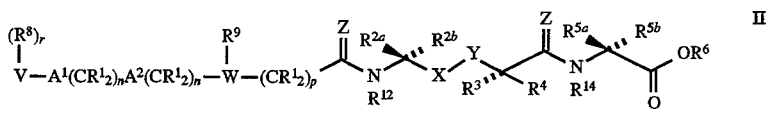

wherein:
$R^1$ is independently selected from:
a) hydrogen,
b) aryl, heterocyclic, cycloalkyl, $R^{10}O$—, —$N(R^{10})_2$ or alkenyl,
c) $C_1$–$C_6$ alkyl, and
d) $C_1$–$C_6$ alkyl substituted with a group selected from: aryl, heterocyclic, cycloalkyl, alkenyl, $R^{10}O$—, or —$N(R^{10})_2$;

$R^{2a}$ is selected from:
a) a side chain of a naturally occurring amino acid, wherein the amino acid is selected from alanine, leucine, isoleucine and valine;
b) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
c) a group selected from $C_1$–$C_{20}$ alkyl, $C_2$–$C_{20}$ alkenyl, $C_3$–$C_{10}$ cycloalkyl, aryl or heterocyclic group, and
d) $C_1$–$C_6$ alkyl substituted with a group selected from:
i) aryl,
ii) substituted aryl,
iii) heterocyclic,
iv) substituted heterocyclic,
v) $C_3$–$C_{10}$ cycloalkyl, and
vi) substituted $C_3$–$C_{10}$ cycloalkyl;

$R^{2b}$ is selected from hydrogen and $C_1$–$C_6$ alkyl; or
$R^{2a}$ and $R^{2b}$ are combined to form —$(CH_2)_s$—;
$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
i) aryl,
ii) substituted aryl, iii) heterocyclic,
iv) substituted heterocyclic,
v) $C_3$–$C_{10}$ cycloalkyl, and
vi) substituted $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
  i) methionine sulfoxide, or
  ii) methionine sulfone, and
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;

$R^{5b}$ is selected from:
a) hydrogen, and
b) $C_1$–$C_3$ alkyl; or $R^{5a}$ or $R^{5b}$ are combined with $R^{14}$ to form a ring such that

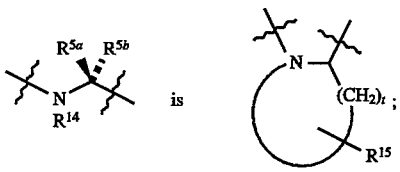

$R^6$ is
a) $C_1$–$C_8$ alkyl,
b) $C_1$–$C_8$ alkyl substituted with a group selected from:
  1) aryl,
  2) heterocycle,
  3) —$N(R^{11})_2$,
  4) —$OR^{10}$, or c) 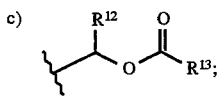

X-Y is a) 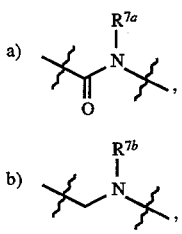

b) 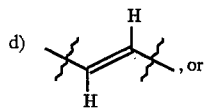

c) 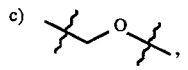

d) 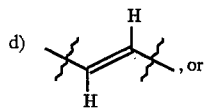, or e) —$CH_2$—$CH_2$—;

$R^{7a}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl, and
i) $C_1$–$C_6$ alkyl substituted with a group selected from aryl, substituted aryl, heterocyclic, substituted heterocyclic, cycloalkyl and substituted cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl,
i) $C_1$–$C_6$ alkyl substituted with a group selected from aryl, substituted aryl, heterocyclic, substituted heterocyclic, cycloalkyl and substituted cycloalkyl,
j) a carbonyl group which is bonded to a group selected from aryl, substituted aryl, heterocyclic, substituted heterocyclic, cycloalkyl and substituted cycloalkyl,
k) a carbonyl group which is bonded to a $C_1$–$C_6$ alkyl substituted with hydrogen or an unsubstituted or substituted group selected from aryl, heterocyclic and cycloalkyl,
l) a carbonyl group which is bonded to a $C_1$–$C_6$ alkyl substituted with a group selected from aryl, substituted aryl, heterocyclic, substituted heterocyclic, cycloalkyl and substituted cycloalkyl,
m) a sulfonyl group which is bonded to a group selected from aryl, substituted aryl, heterocyclic, substituted heterocyclic, cycloalkyl and substituted cycloalkyl,
n) a sulfonyl group which is bonded to a $C_1$–$C_6$ alkyl substituted with hydrogen or an unsubstituted or substituted group selected from aryl, heterocyclic and cycloalkyl, and
p) a sulfonyl group which is bonded to a $C_1$–$C_6$ alkyl substituted with a group selected from aryl, substituted aryl, heterocyclic, substituted heterocyclic, cycloalkyl and substituted cycloalkyl, wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted with a group selected from $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) $C_1$–$C_6$ alkyl, and
d) $C_1$–$C_6$ alkyl substituted with a group selected from $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{13}$ is 1,1-dimethylethyl;

$R^{14}$ is independently selected from hydrogen and $C_1$–$C_6$ alkyl;

$R^{15}$ is independently selected from hydrogen and $C_1$–$C_6$ alkyl;

$A^1$ and $A^2$ are independently selected from: a bond, —CH=CH—, —C≡C—, —C(O)—, —C(O)$NR^{10}$—, O, —$N(R^{10})$—, —$NR^{10}C(O)$—, —$S(O)_2N(R^{10})$—, —$N(R^{10})S(O)_2$— or $S(O)_m$;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl,
b) aryl,
c) $C_1$–$C_{20}$ alkyl wherein from 0 to 4 non-terminal carbon atoms are replaced with a heteroatom selected from O, S, and N, and
d) $C_2$–$C_{20}$ alkenyl;
provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 2;

s is 4 or 5; and t is 3, 4 or 5;

or a pharmaceutically acceptable salt thereof.

7. The compound according to claim 3 having the formula III:

$$V-A^1(CR^1_2)_nA^2(CR^1_2)_n-W-(CR^1_2)_p \overset{Z}{\underset{R^{12}}{C-N}} \overset{R^{2a}}{\underset{X}{C}} \overset{R^{2b}}{\underset{R^3}{Y}} \overset{Z}{\underset{R^4}{C-N}} \overset{HOCH_2(CH_2)_q}{\underset{R^{14}}{C}} OH \quad III$$

with $(R^8)_r$ on V and $R^9$ on W;

wherein:

$R^1$ is independently selected from:
a) hydrogen,
b) aryl, heterocyclic, cycloalkyl, $R^{10}O$—, —$N(R^{10})_2$ or alkenyl,
c) $C_1$–$C_6$ alkyl, and
d) $C_1$–$C_6$ alkyl substituted with a group selected from: aryl, heterocyclic, cycloalkyl, alkenyl, $R^{10}O$—, or —$N(R^{10})_2$;

$R^{2a}$ is selected from:
a) a side chain of a naturally occurring amino acid, wherein the amino acid is selected from alanine, leucine, isoleucine and valine;
b) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
c) a group selected from $C_1$–$C_{20}$ alkyl, $C_2$–$C_{20}$ alkenyl, $C_3$–$C_{10}$ cycloalkyl, aryl or heterocyclic group, and
d) $C_1$–$C_6$ alkyl substituted with a group selected from:
i) aryl,
ii) substituted aryl,
iii) heterocyclic,
iv) substituted heterocyclic,
v) $C_3$–$C_{10}$ cycloalkyl, and
vi) substituted $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
i) aryl,
ii) substituted aryl,
iii) heterocyclic, iv) substituted heterocyclic,
v) $C_3$–$C_{10}$ cycloalkyl, and
vi) substituted $C_3$–$C_{10}$ cycloalkyl;

X-Y is

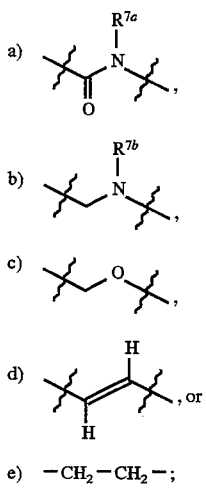

e) —$CH_2$—$CH_2$—;

$R^{7a}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl, and
i) $C_1$–$C_6$ alkyl substituted with a group selected from aryl, substituted aryl, heterocyclic, substituted heterocyclic, cycloalkyl and substituted cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl,
i) $C_1$–$C_6$ alkyl substituted with a group selected from aryl, substituted aryl, heterocyclic, substituted heterocyclic, cycloalkyl and substituted cycloalkyl,
j) a carbonyl group which is bonded to a group selected from aryl, substituted aryl, heterocyclic, substituted heterocyclic, cycloalkyl and substituted cycloalkyl,
k) a carbonyl group which is bonded to a $C_1$–$C_6$ alkyl substituted with hydrogen or an unsubstituted or substituted group selected from aryl, heterocyclic and cycloalkyl,
l) a carbonyl group which is bonded to a $C_1$–$C_6$ alkyl substituted with a group selected from aryl, substituted aryl, heterocyclic, substituted heterocyclic, cycloalkyl and substituted cycloalkyl,
m) a sulfonyl group which is bonded to a group selected from aryl, substituted aryl, heterocyclic, substituted heterocyclic, cycloalkyl and substituted cycloalkyl,
n) a sulfonyl group which is bonded to a $C_1$–$C_6$ alkyl substituted with hydrogen or an unsubstituted or substituted group selected from aryl, heterocyclic and cycloalkyl, and
p) a sulfonyl group which is bonded to a $C_1$–$C_6$ alkyl substituted with a group selected from aryl, substituted aryl, heterocyclic, substituted heterocyclic, cycloalkyl and substituted cycloalkyl,
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted with a group selected from $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) $C_1$–$C_6$ alkyl, and
d) $C_1$–$C_6$ alkyl substituted with a group selected from $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl and aryl;

$R^{11}$ is independently selected from $C_1$–$C_6$ alkyl and aryl;

$R^{12}$ is independently selected from hydrogen and $C_1$–$C_6$ alkyl;

$R^{14}$ is independently selected from hydrogen and $C_1$–$C_6$ alkyl;

$A^1$ and $A^2$ are independently selected from: a bond, —CH=CH—, —C≡C—, —C(O)—, —C(O)NR$^{10}$—, O, —N($R^{10}$)—, —$NR^{10}C(O)$—, —$S(O)_2N(R^{10})$—, —$N(R^{10})S(O)_2$— or $S(O)_m$;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl,
b) aryl,
c) $C_1$–$C_{20}$ alkyl wherein from 0 to 4 non-terminal carbon atoms are replaced with a heteroatom selected from O, S, and N, and
d) $C_2$–$C_{20}$ alkenyl;
provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

q is 0, 1 or 2;

r is 0 to 2; and s is 4 or 5;

or a pharmaceutically acceptable salt thereof.

8. The compound according to claim 4 having the formula IV:

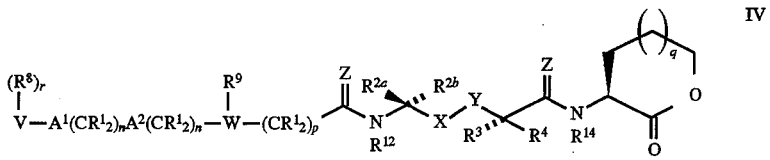

wherein:

$R^1$ is independently selected from:
a) hydrogen,
b) aryl, heterocyclic, cycloalkyl, $R^{10}O$—, —$N(R^{10})_2$ or alkenyl,
c) $C_1$–$C_6$ alkyl, and
d) $C_1$–$C_6$ alkyl substituted with a group selected from: aryl, heterocyclic, cycloalkyl, alkenyl, $R^{10}O$—, or —$N(R^{10})_2$;

$R^{2a}$ is selected from:
a) a side chain of a naturally occurring amino acid, wherein the amino acid is selected from alanine, leucine, isoleucine and valine;
b) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
c) a group selected from $C_1$–$C_{20}$ alkyl, $C_2$–$C_{20}$ alkenyl, $C_3$–$C_{10}$ cycloalkyl, aryl or heterocyclic group, and
d) $C_1$–$C_6$ alkyl substituted with a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;

X-Y is

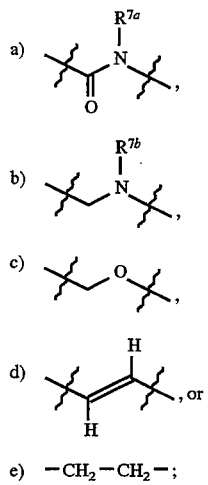

e) —$CH_2$—$CH_2$—;

$R^{7a}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl, and
i) $C_1$–$C_6$ alkyl substituted with a group selected from aryl, substituted aryl, heterocyclic, substituted heterocyclic, cycloalkyl and substituted cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) aryl,
c) substituted aryl,
d) heterocyclic,
e) substituted heterocyclic,
f) cycloalkyl,
g) substituted cycloalkyl,
h) $C_1$–$C_6$ alkyl,
i) $C_1$–$C_6$ alkyl substituted with a group selected from aryl, substituted aryl, heterocyclic, substituted heterocyclic, cycloalkyl and substituted cycloalkyl,
j) a carbonyl group which is bonded to a group selected from aryl, substituted aryl, heterocyclic, substituted heterocyclic, cycloalkyl and substituted cycloalkyl,
k) a carbonyl group which is bonded to a $C_1$–$C_6$ alkyl substituted with hydrogen or an unsubstituted or substituted group selected from aryl, heterocyclic and cycloalkyl, l) a carbonyl group which is bonded to a $C_1-C_6$ alkyl substituted with a group selected from aryl, substituted aryl, heterocyclic, substituted heterocyclic, cycloalkyl and substituted cycloalkyl, m) a sulfonyl group which is bonded to a group selected from aryl, substituted aryl, heterocyclic, substituted heterocyclic, cycloalkyl and substituted cycloalkyl, n) a sulfonyl group which is bonded to a $C_1-C_6$ alkyl substituted with hydrogen or an unsubstituted or substituted group selected from aryl, heterocyclic and cycloalkyl, and p) a sulfonyl group which is bonded to a $C_1-C_6$ alkyl substituted with a group selected from aryl, substituted aryl, heterocyclic, substituted heterocyclic, cycloalkyl and substituted cycloalkyl, wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is selected from:

a) hydrogen, b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and c) $C_1-C_6$ alkyl substituted with a group selected from $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^9$ is selected from:

a) hydrogen, b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, c) $C_1-C_6$ alkyl, and d) $C_1-C_6$ alkyl substituted with a group selected from $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $-N(R^{10})_2$, or $R^{11}OC(O)NR^{10}-$;

$R^{10}$ is independently selected from hydrogen, $C_1-C_6$ alkyl and aryl;

$R^{11}$ is independently selected from $C_1-C_6$ alkyl and aryl;

$R^{12}$ is independently selected from hydrogen and $C_1-C_6$ alkyl;

$R^{14}$ is independently selected from hydrogen and $C_1-C_6$ alkyl;

$A^1$ and $A^2$ are independently selected from: a bond, $-CH=CH-$, $-C\equiv C-$, $-C(O)-$, $-C(O)NR^{10}-$, O, $-N(R^{10})-$, $-NR^{10}C(O)-$, $-S(O)_2N(R^{10})-$, $-N(R^{10})S(O)_2-$ or $S(O)_m$;

V is selected from:

a) heterocycle selected from pyrrolidinyl, imidazolyl, pyridinyl, thiazolyl, pyridonyl, 2-oxopiperidinyl, indolyl, quinolinyl, isoquinolinyl, and thienyl, b) aryl, c) $C_1-C_{20}$ alkyl wherein from 0 to 4 non-terminal carbon atoms are replaced with a heteroatom selected from O, S, and N, and d) $C_2-C_{20}$ alkenyl;

provided that V is not hydrogen if $A^1$ is $S(O)_m$ and V is not hydrogen if $A^1$ is a bond, n is 0 and $A^2$ is $S(O)_m$ or a bond;

W is a heterocycle selected from pyrrolidinyl, imidazolyl, pyridinyl, thiazolyl, pyridonyl, piperidinyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

q is 0, 1 or 2;

r is 0 to 2; and s is 4 or 5;

or a pharmaceutically acceptable salt thereof.

9. A compound which inhibits farnesyl-protein transferase which is:

N-[2(S)-(1-(Phenylmethyl)-1H-imidazol-4-ylacetyl)amino-3(S)-methylpentyl]-N-1-naphthylmethyl-glycyl-methionine N-[2(S)-(1-(Phenylmethyl)-1H-imidazol-4-ylacetyl)amino-3(S)-methylpentyl]-N-1-naphthylmethyl-glycyl-methionine methyl ester N-[2(S)-(1-(Phenylmethyl)-1H-imidazol-5-ylacetyl)amino-3(S)-methylpentyl]-N-1-naphthylmethyl-glycyl-methionine N-[2(S)-(1-(Phenylmethyl)-1H-imidazol-5-ylacetyl)-amino-3(S)-methylpentyl]-N-1-naphthylmethyl-glycyl-methionine methyl ester N-[2(S)-(1-(4-Nitrophenylmethyl)-1H-imidazol-4-ylacetyl)amino-3(S)-methylpentyl]-N-1-naphthylmethyl-glycyl-methionine N-[(2S)-(1-(4-Nitrophenylmethyl)-1H-imidazol-4-ylacetyl)amino-3(S)-methylpentyl]-N-1-naphthylmethyl-glycyl-methionine methyl ester N-[2(S)-(1-(4-Nitrophenylmethyl)-1H-imidazol-5-ylacetyl)amino-3(S)-methylpentyl]-N-1-naphthylmethyl-glycyl-methionine N-[2(S)-(1-(4-Nitrophenyl-methyl)-1H-imidazol-5-ylacetyl)amino-3(S)-methylpentyl]-N-1-naphthylmethyl-glycyl-methionine methyl ester N-[2(S)-(1-(2-Naphthylmethyl)-1H-imidazol-5-ylacetyl)amino-3(S)-methylpentyl]-N-1-naphthylmethyl-glycyl-methionine N-[2(S)-(1-(2-Naphthylmethyl)-1H-imidazol-5-ylacetyl)amino-3(S)-methylpentyl]-N-1-naphthylmethyl-glycyl-methionine methyl ester N-[2(S)-(1-(1-Naphthylmethyl)-1H-imidazol-5-ylacetyl)amino-3(S)-methylpentyl]-N-1-naphthylmethyl-glycyl-methionine N-[2(S)-(1-(1-Naphthylmethyl)-1H-imidazol-5-ylacetyl)amino-3(S)-methylpentyl]-N-1-naphthylmethyl-glycyl-methionine methyl ester N-[2(S)-(1-Farnesyl-1H-imidazol-5-ylacetyl)amino-3(S)-methylpentyl]-N-1-naphthylmethyl-glycyl-methionine N-[2(S)-(1-Farnesyl-1H-imidazol-5-ylacetyl)amino-3(S)-methylpentyl]-N-1-naphthylmethyl-glycyl-methionine methyl ester N-[2(S)-(1-Geranyl-1H-imidazol-5-ylacetyl)amino-3(S)-methylpentyl]-N-1-naphthylmethyl-glycyl-methionine N-[2(S)-(1-Geranyl-1H-imidazol-5-ylacetyl)amino-3(S)-methylpentyl]-N-1-naphthylmethyl-glycyl-methionine methyl ester N-[2(S)-(1-(4-Pyridylmethyl)-1H-imidazol-4-ylacetyl)amino-3(S)-methylpentyl]-N-1-naphthylmethyl-glycyl-methionine N-[2(S)-(1-(4-Pyridylmethyl)-1H-imidazol-4-ylacetyl)amino-3(S)-methylpentyl]-N-1-naphthylmethyl-glycyl-methionine methyl ester N-[2(S)-(1-(4-Pyridylmethyl)-1H-imidazol-5-ylacetyl)amino-(3S)-methylpentyl]-N-1-naphthylmethyl-glycyl-methionine N-[2(S)-(1-(4-Pyridylmethyl)-1H-imidazol-5-ylacetyl) amino-3(S)-methylpentyl]-N-1-naphthylmethyl-glycyl-methionine methyl ester N-[2(S)-(1-(4-Cyanophenylmethyl)-1H-imidazol-5-ylacetyl)amino-3(S)-methylpentyl]-N-1-naphthylmethyl-glycyl-methionine N-[2(S)-(1-(4-Cyanophenylmethyl)-1H-imidazol-5-ylacetyl)amino-3(S)-methylpentyl]-N-1-naphthylmethyl-glycyl-methionine methyl ester N-[2(S)-(1-(4-Methoxyphenylmethyl)-1H-imidazol-5-ylacetyl)amino-3(S)-methylpentyl]-N-1-naphthylmethyl-glycyl-methionine N-[2(S)-(1-(4-Methoxyphenylmethyl)-1H-imidazol-5-ylacetyl)amino-3(S)-methylpentyl]-N-1-naphthylmethyl-glycyl-methionine methyl ester N-[2(S)-(1-(4-Quinolinylmethyl)-1H-imidazol-5-ylacetyl) amino-3(S)-methylpentyl]-N-1-naphthylmethyl-glycyl-methionine N-[2(S)-(1-(4-Quinolinylmethyl)-1H-imidazol-5-ylacetyl) amino-3(S)-methylpentyl]-N-1-naphthylmethyl-glycyl-methionine methyl ester N-[2(S)-(1-(2-Naphthylmethyl)-1H-imidazol-5-ylacetyl) amino-3(S)-methylpentyl]-N-1-phenylmethyl-glycyl-methionine N-[2(S)-(1-(2-Naphthylmethyl)-1H-imidazol-5-ylacetyl) amino-3(S)-methylpentyl]-N-1-phenylmethyl-glycyl-methionine methyl ester N-[2(S)-(1-(2-Naphthylmethyl)-1H-imidazol-5-ylethyl) amino-3(S)-methylpentyl]-N-1-naphthylmethyl-glycyl-methionine N-[2(S)-(1-(2-Naphthylmethyl)-1H-imidazol-5-ylethyl) amino-3(S)-methylpentyl]-N-1-naphthylmethyl-glycyl-methionine methyl ester 2(S)-[N-2(S)-(1-(2-Naphthylmethyl)-1H-imidazol-5-ylacetyl)amino-3(S)-methyl]pentyloxy-3-phenylpropionyl-methionine sulfone methyl ester 2(S)-[N-2(S)-(1-(2-Naphthylmethyl)-1H-imidazol-5-ylacetyl)amino-3(S)-methyl]pentyloxy-3-phenylpropionyl-methionine sulfone 2(S)-[N-2(S)-(1-(2-Naphthylmethyl)-1H-imidazol-5-ylethyl)amino-3(S)-methyl]pentyloxy-3-phenylpropionyl-methionine methyl ester 2(S)-[N-2(S)-(1-(2-Naphthylmethyl)-1H-imidazol-5-ylethyl)amino-3(S)-methyl]pentyloxy-3-phenylpropionyl-methionine N-[2(S)-(1-Methyl-1H-imidazol-4-ylacetyl)-amino-3(S)-methylpentyl]-N-(1-naphthylmethyl)-glycyl-methionine methyl ester N-[2(S)-(1-Methyl-1H-imidazol-4-ylacetyl)-amino -3(S)-methylpentyl]-N-(1-naphthylmethyl)-glycyl-methionine N-[2(S)-N-(2-Naphthylmethyl)-1H-imidazol-5-ylacetyl] amino-(3S)-methylpentyl]-N-(cyclopropylmethyl)-glycylmethionine methyl ester N-[(2S)-N-(2-Naphthylmethyl)-1H-imidazol-5-ylacetyl] amino-(3S)-methylpentyl]-N-(cyclopropylmethyl)-glycylmethionine N-[2(S)-[(5(R,S)-Methylpyroglutamyl)amino]-3(S)-methylpentyl]-N-(1-naphthylmethyl)-glycylmethionine methyl ester N-[2(S)-[(5(R,S)-Methylpyroglutamyl)amino]-3(S)-methylpentyl]-N-(1-naphthylmethyl)-glycylmethionine N-[2(S)-((N-Methylpyroglutamyl)amino)-3(S)-methylpentyl]-N-(1-naphthylmethyl)-glycyl-methionine N-[2(S)-((N-Methylpyroglutamyl)-amino)-3(S)-methylpentyl]-N-(1-naphthylmethyl)-glycyl-methionine methyl ester N-[2(S)-(N-Formylprolylamino)-3(S)-methylpentyl]-N-(1-naphthylmethyl)-glycyl-methionine methyl ester N-[2(S)-(N-Formylprolylamino)-3(S)-methylpentyl]-N-(1-naphthylmethyl)-glycyl-methionine N-[2(S)-(N'-(4-Nitrobenzyl)pyroglutamyl)-amino)-3(S)-methylpentyl]-N-(1-naphthylmethyl)-glycyl-methionine methyl ester N-[2(S)-(N'-(4-Nitrobenzyl)pyroglutamyl)-amino)-3(S)-methylpentyl]-N-(1-naphthylmethyl)-glycyl-methionine N-[2(S)-((N'-Benzylpyroglutamyl)amino)-3(S)-methylpentyl]-N-(1-naphthylmethyl)-glycyl-methionine methyl ester N-[2(S)-(N'-Benzylpyroglutamyl)amino)-3(S)-methylpentyl]-N-(1-naphthylmethyl)-glycyl-methionine N-[2(S)-1-(4-Fluorophenylmethyl)-1H-imidazol-5-ylacetyl) amino-3(S)-methylpentyl]-N-1-naphthylmethyl-glycyl-methionine methyl ester N-[2(S)-1-(4-Fluorophenylmethyl)-1H-imidazol-5-ylacetyl) amino-3(S)-methylpentyl]-N-1-naphthylmethyl-glycyl-methionine N-[2(S)-([1-(4-cyanobenzyl)-1H-imidazol-5-yl] acetylamino)-3(S)-methylpentyl]-N-(1-naphthylmethyl) glycyl-methionine isopropyl ester N-[2(S)-([1-(4-cyanobenzyl)-1H-imidazol-5-yl] acetylamino)-3(S)-methylpentyl]-N-(1-naphthylmethyl) glycyl-methionine sulfone methyl ester N-[2(S)-([1-(4-cyanobenzyl)-1H-imidazol-5-yl] acetylamino)-3(S)-methylpentyl]-N-(1-naphthylmethyl) glycyl-methionine sulfone N-[2(S)-([1-(4-cyanobenzyl)-1H-imidazol-5-yl] acetylamino)-3(S)-methylpentyl]-N-(1-naphthylmethyl) glycyl-(3-acetylamino)alanine methyl ester N-[2(S)-([1-(4-cyanobenzyl)-1H-imidazol-5-yl] acetylamino)-3(S)-methylpentyl]-N-(1-naphthylmethyl) glycyl-(3-acetylamino)alanine N-[2(S)-([1-(4-cyanobenzyl)-1H-imidazol-5-yl] acetylamino)-3(S)-methylpentyl]-N-(1-naphthylmethyl) glycyl-2(RS) amino-3-(2 thienyl)propionic acid methyl ester N-[2(S)-([1-(4-cyanobenzyl)-1H-imidazol-5-yl] acetylamino)-3(S)-methylpentyl]-N-(1-naphthylmethyl) glycyl-2(RS)-amino-3-(2 thienyl)propionic acid N-[2(S)-([1-(4-cyanobenzyl)-1H-imidazol-5-yl] acetylamino)-3(S)-methylpentyl]-N-(1-naphthylmethyl) glycyl-2(S) amino-4-sulfamyl-butanoic acid methyl ester N-[2(S)-([1-(4-cyanobenzyl)-1H-imidazol-5-yl] acetylamino)-3(S)-methylpentyl]-N-(1-naphthylmethyl) glycyl-2(S) amino-4-sulfamyl-butanoic acid N-[2(S)-([1-(4-cyanobenzyl)-1H-imidazol-5-yl] acetylamino)-3(S)-methylpentyl]-N-(1-naphthylmethyl) glycyl-N-methyl methionine methyl ester N-[2(S)-([1-(4-cyanobenzyl)-1H-imidazol-5-yl] acetylamino)-3(S)-methylpentyl]-N-(1-naphthylmethyl) glycyl-N-methyl methionine N-[2(S)-([1-(4-cyanobenzyl)-1H-imidazol-5-yl] acetylamino)-3(S)-methylpentyl]-N-(1-naphthylmethyl) glycyl-homoserine lactone N-[2(S)-([1-(4-cyanobenzyl)-1H-imidazol-5-yl] acetylamino)-3(S)-methylpentyl]-N-(1-naphthylmethyl) glycyl-homoserine N-[2(S)-([1-(4-cyanobenzyl)-1H-imidazol-5-yl] acetylamino)-3(S)-methylpentyl]-N-(1-naphthylmethyl) glycyl-proline methyl ester N-[2(S)-([1-(4-cyanobenzyl)-1H-imidazol-5-yl] acetylamino)-3(S)-methylpentyl]-N-(1-naphthylmethyl) glycyl-proline N-[2(S)-([1-(4-cyanobenzyl)-1H-imidazol-5-yl] acetylamino)-3(S)-methylpentyl]-N-(1-naphthylmethyl) glycyl-D-proline methyl ester N-[2(S)-([1-(4-cyanobenzyl)-1H-imidazol-5-yl]
acetylamino)-3(S)-methylpentyl]-N-(1-naphthylmethyl)
glycyl-D-proline N-[2(S)-([1-(4-cyanobenzyl)-1H-imidazol-5-yl]
acetylamino)-3(S)-methylpentyl]-N-(1-naphthylmethyl)
glycyl-L-pipecolinic acid N-[2(S)-([1-(4-carbomethoxybenzyl)-1H-imidazol-5-yl]
acetylamino)-3(S)-methylpentyl]-N-(1-naphthylmethyl)
glycyl-methionine methyl ester N-[2(S)-([1-(4-carbomethoxybenzyl)-1H-imidazol-5-yl]
acetylamino)-3(S)-methylpentyl]-N-(1-naphthylmethyl)
glycyl-methionine 1-(2-naphthylmethyl)-1H-imidazol-5-ylacetyl-isoleucinyl-
phenylalaninyl-methionine methyl ester 1-(2-naphthylmethyl)-1H-imidazol-5-ylacetyl-isoleucinyl-
phenylalaninyl-methionine or a pharmaceutically acceptable salt thereof.

10. A compound according to claim 9 which inhibits
farnesyl-protein transferase which is:

N-[2(S)-(1-(4-Nitrophenylmethyl)-1H-imidazol-5-ylacetyl)
amino-3(S)-methylpentyl]-N-1-naphthylmethyl-glycyl-
methionine

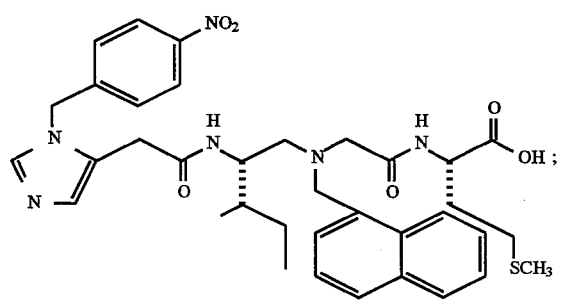

or a pharmaceutically acceptable salt thereof.

11. A compound according to claim 9 which inhibits
farnesyl-protein transferase which is:

N-[2(S)-N'-(1-(4-Nitrophenyl-methyl)-1H-imidazol-5-
ylacetyl)amino-3(S)-methylpentyl]-N-1-naphthylmethyl-
glycyl-methionine methyl ester

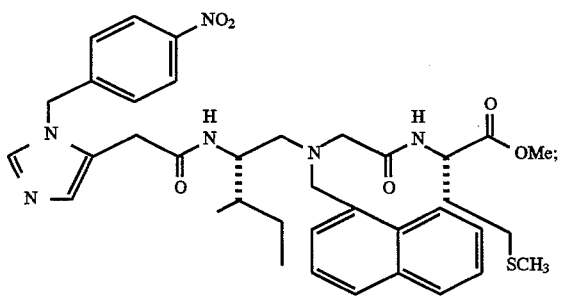

or a pharmaceutically acceptable salt thereof.

12. A compound according to claim 9 which inhibits
farnesyl-protein transferase which is:

N-[2(S)-(1-(4-Cyanophenylmethyl)-1H-imidazol-5-
ylacetyl)amino-3(S)-methylpentyl]-N-1-naphthylmethyl-
glycyl-methionine

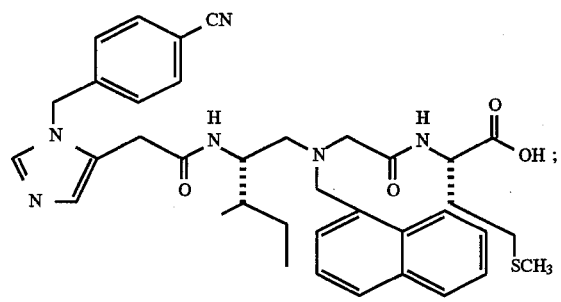

or a pharmaceutically acceptable salt thereof.

13. A compound according to claim 9 which inhibits
farnesyl-protein transferase which is:

N-[2(S)-(1-(4-Cyanophenyl-methyl)-1H-imidazol-5-
ylacetyl)amino-3(S)-methylpentyl]-N-1-naphthylmethyl-
glycyl-methionine methyl ester

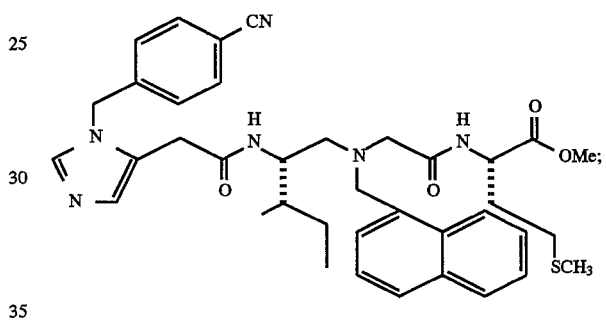

or a pharmaceutically acceptable salt thereof.

14. A compound according to claim 9 which inhibits
farnesyl-protein transferase which is:

N-[2(S)-(1-(4-Cyanophenyl-methyl)-1H-imidazol-5-
ylacetyl)amino-3(S)-methylpentyl]-N-1-naphthylmethyl-
glycyl-methionine isopropyl ester

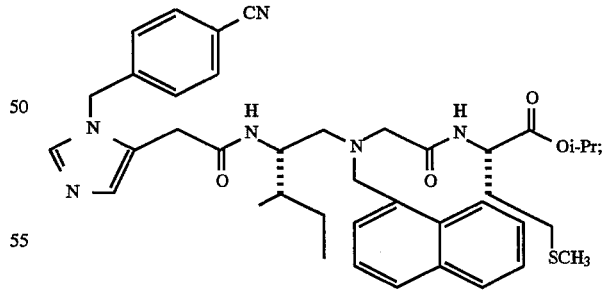

or a pharmaceutically acceptable salt thereof.

15. A compound according to claim 9 which inhibits
farnesyl-protein transferase which is:

N-[2(S)-(1-(4-Methoxyphenylmethyl)-1H-imidazol-5-
ylacetyl)amino-3(S)-methylpentyl]-N-1-naphthylmethyl-
glycyl-methionine

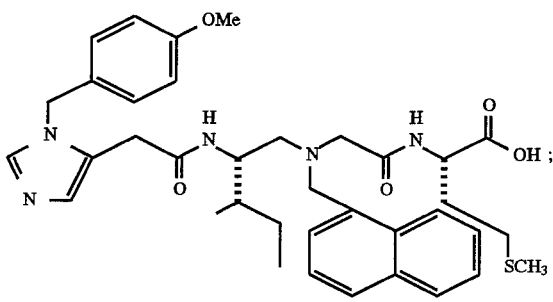

or a pharmaceutically acceptable salt thereof.

16. A compound according to claim 9 which inhibits farnesyl-protein transferase which is:

N-[2(S)-(1-(4-Methoxyphenyl-methyl)-1H-imidazol-5-ylacetyl)amino-3(S)-methylpentyl]-N-1-naphthylmethyl-glycyl-methionine methyl ester

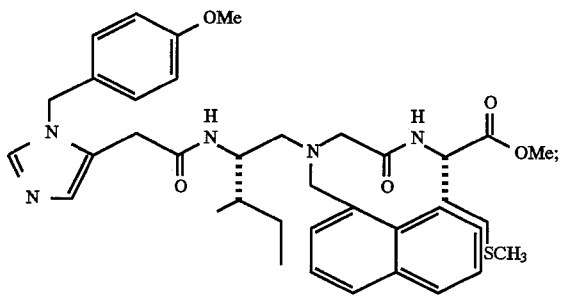

or a pharmaceutically acceptable salt thereof.

17. A compound according to claim 9 which inhibits farnesyl-protein transferase which is:

N-[2(S)-(1-(2-Naphthylmethyl)-1H-imidazol-5-ylacetyl)amino-3(S)-methylpentyl]-N-1-naphthylmethyl-glycyl-methionine

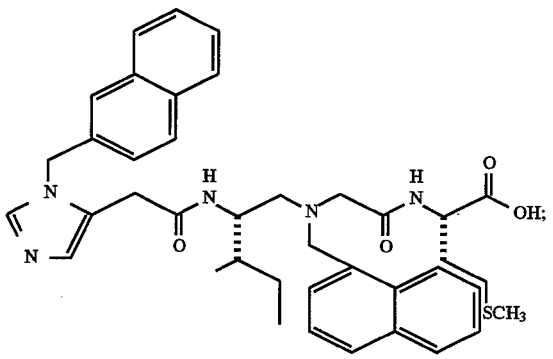

or a pharmaceutically acceptable salt thereof.

18. A compound according to claim 9 which inhibits farnesyl-protein transferase which is:

N-[2(S)-(1-(2-Naphthylphenyl-methyl)-1H-imidazol-5-ylacetyl)amino-3(S)-methylpentyl]-N-1-naphthylmethyl-glycyl-methionine methyl ester

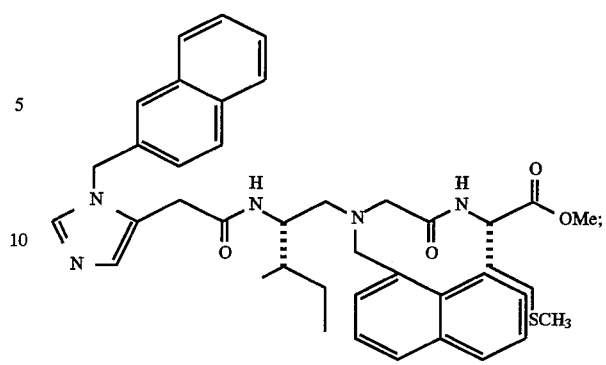

or a pharmaceutically acceptable salt thereof.

19. A compound according to claim 9 which inhibits farnesyl-protein transferase which is:

N-[2(S)-(1-(4-Cyanophenyl-methyl)-1H-imidazol-5-ylacetyl)amino-3(S)-methylpentyl]-N-1-naphthylmethyl-glycyl-methionine sulfone methyl ester

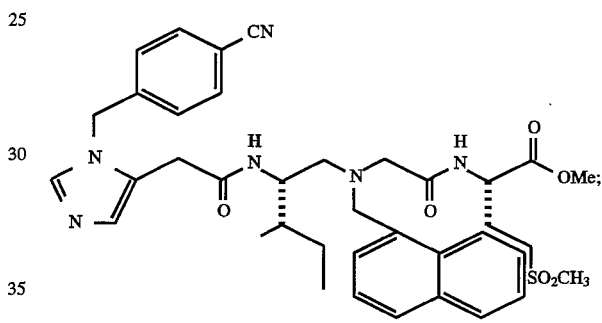

or a pharmaceutically acceptable salt thereof.

20. A compound according to claim 9 which inhibits farnesyl-protein transferase which is:

N-[2(S)-(1-(4-Cyanophenyl-methyl)-1H -imidazol-5-ylacetyl)amino-3(S)-methylpentyl]-N-1-naphthylmethyl-glycyl-methionine sulfone

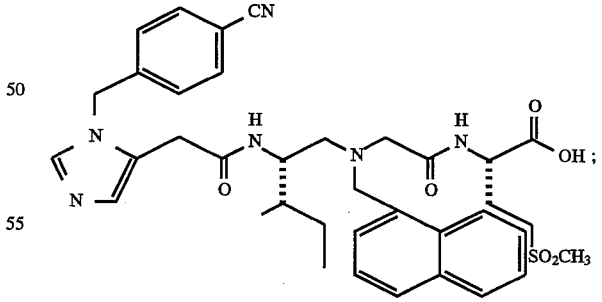

or a pharmaceutically acceptable salt thereof.

21. A compound according to claim 9 which inhibits farnesyl-protein transferase which is:

N-[2(S)-(1-(4-Cyanophenyl-methyl)-1H-imidazol-5-ylacetyl)amino-3(S)-methylpentyl]-N-1-naphthylmethyl-glycyl-(3-acetylamino)alanine methyl ester

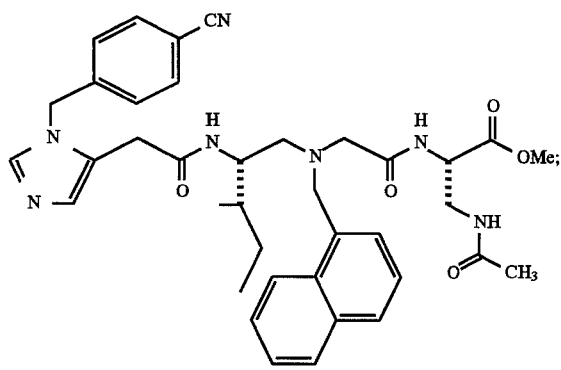

or a pharmaceutically acceptable salt thereof.

22. A compound according to claim 9 which inhibits farnesyl-protein transferase which is:

N-[2(S)-(1-(4-Cyanophenyl-methyl)-1H-imidazol-5-ylacetyl)amino-3(S)-methylpentyl]-N-1-naphthylmethyl-glycyl-(3-acetylamino)alanine methyl ester

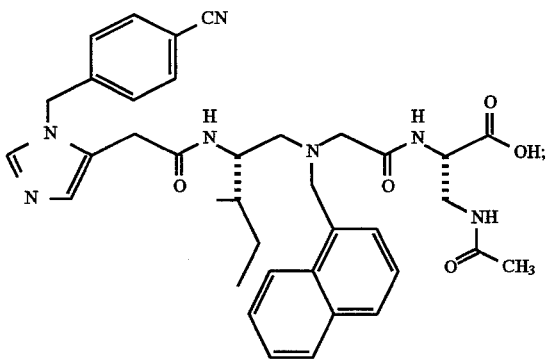

or a pharmaceutically acceptable salt thereof.

23. A compound according to claim 9 which inhibits farnesyl-protein transferase which is:

N-[2(S)-(1-(4-Cyanophenylmethyl)-1H-imidazol-5-ylacetyl)amino-3(S)-methylpentyl]-N-1-naphthylmethyl-glycyl-N-methyl-methionine

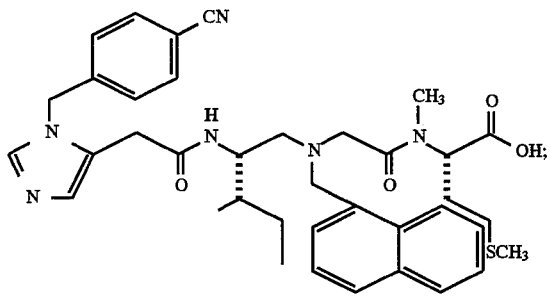

or a pharmaceutically acceptable salt thereof.

24. A compound according to claim 9 which inhibits farnesyl-protein transferase which is:

N-[2(S)-(1-(4-Cyanophenyl-methyl)-1H-imidazol-5-ylacetyl)amino-3(S)-methylpentyl]-N-1-naphthylmethyl-glycyl-N-methyl-methionine methyl ester

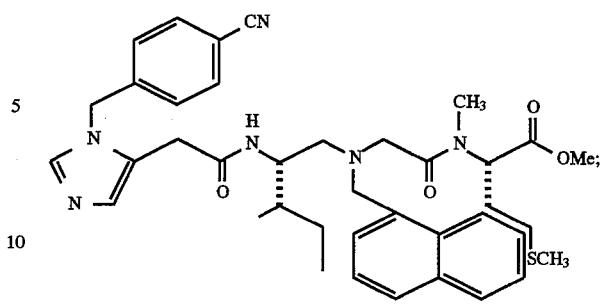

or a pharmaceutically acceptable salt thereof.

25. A pharmaceutical composition comprising a pharmaceutical carrier, and dispersed therein, a therapeutically effective amount of a compound of claim 1.

26. A pharmaceutical composition comprising a pharmaceutical carrier, and dispersed therein, a therapeutically effective amount of a compound of claim 2.

27. A pharmaceutical composition comprising a pharmaceutical carrier, and dispersed therein, a therapeutically effective amount of a compound of claim 3.

28. A pharmaceutical composition comprising a pharmaceutical carrier, and dispersed therein, a therapeutically effective amount of a compound of claim 4.

29. A pharmaceutical composition comprising a pharmaceutical carrier, and dispersed therein, a therapeutically effective amount of a compound of claim 9.

30. A method for inhibiting farnesylation of Ras protein which comprises administering to a mammal in need thereof a therapeutically effective amount of the composition of claim 25.

31. A method for inhibiting farnesylation of Ras protein which comprises administering to a mammal in need thereof a therapeutically effective amount of the composition of claim 26.

32. A method for inhibiting farnesylation of Ras protein which comprises administering to a mammal in need thereof a therapeutically effective amount of the composition of claim 27.

33. A method for inhibiting farnesylation of Ras protein which comprises administering to a mammal in need thereof a therapeutically effective amount of the composition of claim 28.

34. A method for inhibiting farnesylation of Ras protein which comprises administering to a mammal in need thereof a therapeutically effective amount of the composition of claim 29.

35. A method for treating cancer which comprises administering to a mammal in need thereof a therapeutically effective amount of the composition of claim 25.

36. A method for treating cancer which comprises administering to a mammal in need thereof a therapeutically effective amount of the composition of claim 26.

37. A method for treating cancer which comprises administering to a mammal in need thereof a therapeutically effective amount of the composition of claim 27.

38. A method for treating cancer which comprises administering to a mammal in need thereof a therapeutically effective amount of the composition of claim 28.

39. A method for treating cancer which comprises administering to a mammal in need thereof a therapeutically effective amount of the composition of claim 29.

* * * * *